(12) United States Patent
Wang et al.

(10) Patent No.: US 9,761,805 B2
(45) Date of Patent: *Sep. 12, 2017

(54) ORGANIC SEMICONDUCTORS

(75) Inventors: Changsheng Wang, Durham (GB);
Steven Tierney, Southampton (GB);
Mansoor D'Lavari, Bude (GB); Lana Nanason, Southampton (GB)

(73) Assignee: MERCK PATENT GMBH, Darmstadt (DE)

( * ) Notice: Subject to any disclaimer, the term of this patent is extended or adjusted under 35 U.S.C. 154(b) by 394 days.

This patent is subject to a terminal disclaimer.

(21) Appl. No.: 14/234,201

(22) PCT Filed: Jun. 21, 2012

(86) PCT No.: PCT/EP2012/002625
§ 371 (c)(1),
(2), (4) Date: Jan. 22, 2014

(87) PCT Pub. No.: WO2013/010614
PCT Pub. Date: Jan. 24, 2013

(65) Prior Publication Data
US 2014/0158949 A1   Jun. 12, 2014

(30) Foreign Application Priority Data
Jul. 19, 2011  (EP) .................................. 11005901

(51) Int. Cl.
*H01L 51/00* (2006.01)
*C07D 495/22* (2006.01)
*C08G 61/12* (2006.01)
*H01L 51/42* (2006.01)

(52) U.S. Cl.
CPC ........ *H01L 51/0043* (2013.01); *C07D 495/22* (2013.01); *C08G 61/126* (2013.01); *H01L 51/0036* (2013.01); *C08G 2261/124* (2013.01); *C08G 2261/1412* (2013.01); *C08G 2261/19* (2013.01); *C08G 2261/3243* (2013.01); *C08G 2261/411* (2013.01); *C08G 2261/414* (2013.01); *C08G 2261/51* (2013.01); *C08G 2261/91* (2013.01); *C08G 2261/92* (2013.01); *H01L 51/4253* (2013.01); *Y02E 10/549* (2013.01); *Y02P 70/521* (2015.11)

(58) Field of Classification Search
CPC . C07D 495/22; C08G 61/126; H01L 51/0036; H01L 51/0035; H01L 51/0043
USPC .......... 252/511, 500; 549/41; 528/380, 367, 528/377
See application file for complete search history.

(56) References Cited

U.S. PATENT DOCUMENTS

| | | | |
|---|---|---|---|
| 9,153,784 B2 * | 10/2015 | Mitchell | H01L 51/0043 |
| 2011/0087034 A1 | 4/2011 | Miyata et al. | |
| 2011/0226999 A1 | 9/2011 | Tierney et al. | |
| 2012/0184089 A1 | 7/2012 | Zuberi et al. | |
| 2013/0256604 A1 * | 10/2013 | Blouin | C07D 495/04 252/500 |
| 2014/0001411 A1 * | 1/2014 | Blouin | C08G 61/126 252/501.1 |
| 2014/0008583 A1 * | 1/2014 | Wang | H01L 51/0094 252/500 |
| 2015/0076418 A1 * | 3/2015 | Blouin | C08K 3/04 252/511 |
| 2015/0144846 A1 * | 5/2015 | Nanson | H01L 51/0036 252/500 |
| 2015/0155494 A1 * | 6/2015 | Wei Tan | H01L 51/0036 257/40 |
| 2015/0255725 A1 * | 9/2015 | Mitchell | H01L 51/0035 528/380 |
| 2016/0276591 A1 * | 9/2016 | Mitchell | H01L 51/0003 |

FOREIGN PATENT DOCUMENTS

| | | |
|---|---|---|
| CN | 101939325 A | 1/2011 |
| GB | 2472413 A | 2/2011 |
| JP | 2006-248982 A | 9/2006 |
| JP | 2010280623 A | 12/2010 |
| WO | 2010020329 A1 | 2/2010 |
| WO | 2012017184 A1 | 2/2012 |

OTHER PUBLICATIONS

English translation of JP 2010-280623, Dec. 16, 2010.*
English Translation of Office Action for Related Chinese Patent Application No. 201280034825.4 dated Mar. 18, 2015.
International Search Report for PCT/EP2012/002625 dated May 2, 2013.
Chisso Corp., "Compound having highly plane molecular structure and organic transistor obtained using the same," Patent Abstracts of Japan, Publication Date: Dec. 16, 2010; English Abstract of JP-2010280623.
Taiwanese Office Action with English Translation for Application No. 101125910; dated Jan. 27, 2016.
English Translation of JP2006-248982A, Univ. Nagoya; Sep. 21, 2006; Heteroacene Compound and Method for Producing the Same; Thomas Innovation Record View.

* cited by examiner

*Primary Examiner* — Douglas McGinty
(74) *Attorney, Agent, or Firm* — Millen, White, Zelano and Branigan, P.C.

(57) ABSTRACT

The invention relates to novel organic semiconducting oligomers or polymers containing dithieno[2,3-d:2',3'-d']-s-indaceno[1,2-b:5,6-b']dithiophene units, methods for their preparation and educts or intermediates used therein, polymers, blends, mixtures and formulations containing them, the use of the oligomers, polymers, blends, mixtures and formulations as semiconductor in organic electronic (OE) devices, especially in organic photovoltaic (OPV) devices, and to OE and OPV devices comprising these oligomers, polymers, blends, mixtures or formulations.

22 Claims, No Drawings

ORGANIC SEMICONDUCTORS

FIELD OF THE INVENTION

The invention relates to novel organic semiconducting oligomers and polymers containing dithieno[2,3-d:2',3'-d']-s-indaceno[1,2-b:5,6-b']dithiophene units, methods for their preparation and educts or intermediates used therein, blends, mixtures and formulations containing them, the use of the oligomers, polymers, blends, mixtures and formulations as semiconductors in organic electronic (OE) devices, especially in organic photovoltaic (OPV) devices, and to OE and OPV devices comprising these oligomers, polymers, blends, mixtures or formulations.

BACKGROUND OF THE INVENTION

Organic semiconducting (OSC) materials are receiving growing interest mostly due to their rapid development in the recent years and the lucrative commercial prospects of organic electronics.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 8%.

In order to obtain ideal solution-processible OSC molecules two basic features are essential, firstly a rigid π-conjugated core or backbone, and secondly suitable functionality of the aromatic cores in the OSC backbone. The former extends π-π overlaps, defines the primary energy levels of the highest occupied and lowest unoccupied molecular orbitals (HOMO and LUMO), enables both charge injection and transport, and facilitates optical absorption. The latter further fine-tunes the energy levels and enables solubility and hence processability of the materials as well as π-π interactions of the molecular backbones in the solid state.

A high degree of planarity reduces the energetic disorder of OSC backbones and accordingly enhances charge carrier mobilities. In prior art most of the polymeric OSCs with high charge carries mobilities are generally composed of fused ring aromatic systems, and are semicrystalline in their solid states. Such polymers are for example indacenodithiophene-benzothiadiazole copolymers, for which it was reported by Zhang et al., *J. Am. Chem. Soc.*, 2010, 132(33), 11437 that a hole mobility of 1 cm$^2$/V s was achieved.

Nevertheless, the structures of solubilising groups (e.g., the length, the regio-regularity, the spacial orientation of the alkyl chains etc.), have direct effects on the solubility and hence the processibility of the OSC, on the planarity of the polymer backbone, on the inter-chain π-π interactions and on the HOMO-LUMO levels/bandgaps. For many applications, like e.g. OPV devices, optimisation of the electronic properties of the conjugated backbones by fine-tuning the solubilising functional groups can result in dramatic effects on the efficiencies.

The conventional method of introducing solubilising groups into cyclopentadiarene units like indacenodithiophene (Zhang et al., *J. Am. Chem. Soc.*, 2010, 132(33), 11437), is to alkylate the sp$^3$ carbon atoms of the cyclopentadienes contained in these fused ring structures. Due to the tetrahedral configuration of this carbon, the substituents have to take the orientation within a plane that is normal to the aromatic plane of the conjugated backbone, as shown by X-ray single crystal analysis by Hughes et al., *Org. Biomol. Chem.*, 2003, 1, 3069. These out-of-plane alkyl chains increase the inter-planar separation of the π-π backbones, reducing the degree of inter-molecular π-π interactions. However, from a synthetic point of view, multiple alkylation like for example tetraalkylation of the indacenodithiophene leads to difficulties of purification of the expected products due to the very similar polarities of the product and the incompletely alkylated impurities. Partially alkylated fluorene units are prone to form keto defects within the polymer (Scherf et al, *Adv. Mater.*, 2002, 14, 374).

Thus there is still a need for organic semiconducting (OSC) materials that are easy to synthesize, especially by methods suitable for mass production, show good structural organization and film-forming properties, exhibit good electronic properties, especially a high charge carrier mobility, good processibility, especially a high solubility in organic solvents, and high stability in air. Especially for use in OPV cells, there is a need for OSC materials having a low bandgap, which enable improved light harvesting by the photoactive layer and can lead to higher cell efficiencies, compared to the polymers from prior art.

It was an aim of the present invention to provide new oligomers and polymers for use as organic semiconducting materials that do not have the drawbacks of prior art materials as described above, are easy to synthesize, especially by methods suitable for mass production, and do especially show good processibility, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that one or more of the above aims can be achieved by providing oligomers and conjugated polymers, containing dithieno[2,3-d:2',3'-d']-s-indaceno[1,2-b:5,6-b']dithiophene or other heterocyclic derivatives thereof, which are either tetrasubstituted or dialkylidene-substituted at the cyclopentane rings:

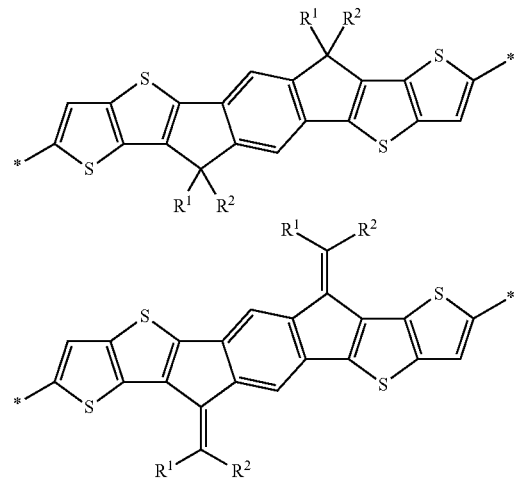

wherein $R^1$ and $R^2$ are e.g. alkyl or fluoroalkyl groups.

Strategically fusing additional aromatic rings along the long axis of the indacenodithiophene core unit creates numerous benefits in developing novel high performance OSC materials. Firstly, fusing additional aromatic rings increases the overall planarity and reduce the number of the potential twists of the conjugated molecular backbone. Elongation of a π-structure or monomer increases the extent of conjugation which facilitates charge transport along the polymer backbone. Secondly, increasing the proportion of sulphur atoms in the molecular backbone through fusing more thiophene rings promotes more intermolecular short contacts, which benefits charge hopping between molecules. Thirdly, the addition of fused-rings means increased proportion of ladder structure in the OSC polymer main chain, which improves the planarity of the molecular backbone. Additionally but not lastly, fusing aromatic rings can more efficiently modify the HOMO and LUMO energy levels and bandgaps of the target monomer structures compared with periphery substitutions.

Moreover, the dialkylidene-substituted dithieno[2,3-d:2',3'-d']-s-indaceno[1,2-b:5,6-b']dithiophenes of the present invention are solubilised using alkylidene groups, of which the carbon atoms connecting to the ring systems are $sp^2$-hybridized instead of $sp^3$-hybridized. The $sp^2$-carbons permit the solubilising alkyl chains to adopt a coplanar conformation relative to the core/polymer backbone, thus further facilitating cofacial aggregation in the solid state. This kind of coplanar orientation of the alkyls has been demonstrated by the crystal structures of compounds as disclosed in the examples of the present invention.

By the incorporation of the electron-donating dithieno[2,3-d:2',3'-d']-s-indaceno[1,2-b:5,6-b']dithiophene unitand an electron-accepting unit into a co-polymer i.e. a "donor-acceptor" polymer, a reduction of the bandgap can be achieved, which enables improved light harvesting properties in bulk heterojunction (BHJ) photovoltaic devices. Also, by varying the substituents at the cyclopentane rings, the solubility and electronic properties of the polymers can be further optimised.

JP 2010-280623 A1 discloses compounds of the following formula

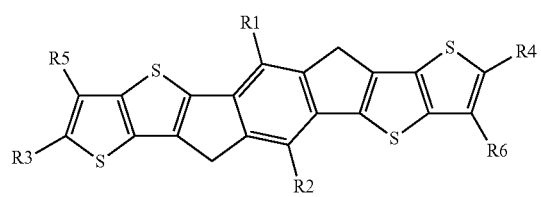

wherein R1-R6 are C1-C30 alkyl. However, these compounds represent a significantly different attempt to solubilise the dithieno[2,3-d:2',3'-d']-s-indaceno[1,2-b:5,6-b']dithiophene core structure, by placing alkyl groups R1-R6 on the terminal thiophene and the central benzene rings.

GB 2472413 A and WO 2012/017184 A1 describe small molecule materials with a general formula as follows

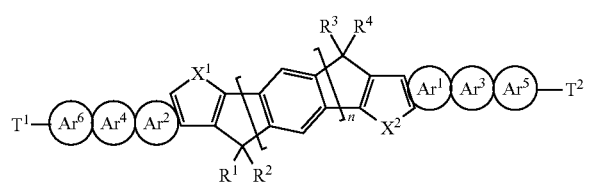

where $Ar^1$ to $Ar^6$ are independently fused heterocycles and $T^1$ and $T^2$ are terminal groups comprising both solubilising chains and reactive functionalities.

However, there is no prior art disclosing oligomeric or polymeric materials containing dithieno[2,3-d:2',3'-d']-s-indaceno[1,2-b:5,6-b']dithiophene as claimed in the present invention.

SUMMARY OF THE INVENTION

The invention relates to oligomers and polymers comprising divalent units of formula I

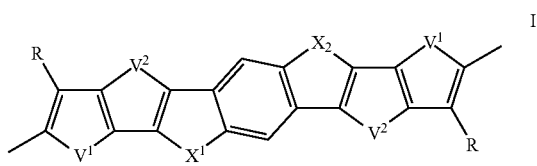

wherein
$V^1$ and $V^2$ are independently of each other O, S, Se or Te,
$X^1$ and $X^2$ are independently of each other $CR^1R^2$, $C=CR^1R^2$, $SiR^1R^2$ or $GeR^1R^2$,
R, $R^1$ and $R^2$ independently of each other, and on each occurrence identically or differently, denote H, F, Cl, Br, CN, straight-chain, branched or cyclic alkyl, with 1 to 30 C atoms, in which one or more non-adjacent C atoms are optionally replaced by —O—, —S—, —C(O)—, —C(O)—O—, —O—C(O)—, —O—C(O)—O—, —C(S)—, —C(S)—O—, —O—C(S)—, —O—C(S)—O—, —C(O)—S—, —S—C(O)—, —O—C(O)—S—, —S—C(O)—O—, —S—C(O)—S—, —S—C(S)—S—, —O—C(S)—S—, —S—C(S)—O—, —C(S)—S—, —S—C(S)—, —NR$^0$—, —SiR$^0$R$^{00}$—, —CY$^1$=CY$^2$— or —C≡C— in such a manner that O and/or S atoms are not linked directly to one another, and in which one or more H atoms are optionally replaced by F, Cl, Br, I or CN, or $R^1$ and $R^2$, independently of each other, and on each occurrence identically or differently, denote aryl, heteroaryl, aryloxy or heteroaryloxy with 4 to 20 ring atoms which is optionally substituted, or $R^1$ and $R^2$ together form an alicyclic group with 1 to 20 C atoms, which is optionally fluorinated or alkylated,
$Y^1$ and $Y^2$ are independently of each other H, F, Cl or CN,
$R^0$ and $R^{00}$ are independently of each other H or optionally substituted $C_{1-40}$ carbyl or hydrocarbyl, and preferably denote H or alkyl with 1 to 12 C-atoms.

The invention further relates to a formulation comprising one or more oligomers or polymers comprising units of formula I and one or more solvents, preferably selected from organic solvents.

The invention further relates to an organic semiconducting formulation comprising one or more oligomers or polymers compounds comprising units of formula I, one or more organic binders, or precursors thereof, preferably having a permittivity ε at 1,000 Hz and 20° C. of 3.3 or less, and optionally one or more solvents.

The invention further relates to the use of units of formula I as electron donor units in semiconducting polymers.

The invention further relates to a conjugated polymer comprising one or more repeating units, wherein said repeating units contain a unit of formula I and/or one or more groups selected from aryl and heteroaryl groups that are optionally substituted, and wherein at least one repeating unit in the polymer contains at least one unit of formula I.

The invention further relates to monomers containing a unit of formula I and further containing one or more reactive groups which can be reacted to form a conjugated polymer as described above and below.

The invention further relates to a semiconducting polymer comprising one or more units of formula I as electron donor units, and preferably further comprising one or more units having electron acceptor properties.

The invention further relates to the use of the oligomers and polymers according to the present invention as electron donor or p-type semiconductor.

The invention further relates to the use of the oligomers and polymers according to the present invention as electron donor component in semiconducting materials, formulations, blends, devices or components of devices.

The invention further relates to a semiconducting material, formulation, blend, device or component of a device comprising an oligomer or a polymer according to the present invention as electron donor component, and preferably further comprising one or more compounds or polymers having electron acceptor properties.

The invention further relates to a mixture or blend comprising one or more oligomers or polymers according to the present invention and one or more additional compounds which are preferably selected from compounds or polymers having one or more of semiconducting, charge transport, hole or electron transport, hole or electron blocking, electrically conducting, photoconducting or light emitting properties.

The invention further relates to a mixture or blend as described above and below, which comprises one or more oligomers or polymers of the present invention and one or more n-type organic semiconductor compounds or polymers, preferably selected from fullerenes or substituted fullerenes.

The invention further relates to a formulation comprising one or more oligomers or polymers, formulations, mixtures or blends according to the present invention and optionally one or more solvents, preferably selected from organic solvents.

The invention further relates to the use of oligomers, polymers, formulations, mixtures and blends of the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more oligomers or polymers, formulations, mixtures or blends of the present invention.

The invention further relates to an optical, electrooptical or electronic component or device comprising one or more oligomers or polymers, formulations, mixtures, blends or components of the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

DETAILED DESCRIPTION OF THE INVENTION

This invention relates to novel oligomers and homo- or co-polymers based upon dithieno[2,3-d:2',3'-d']-s-indaceno[1,2-b:5,6-b']dithiophene units solubilised with four carbyl or hydrocarbyl groups or two alkylidene groups. It also relates to the preparation of these semiconducting oligomers, homopolymers and copolymers through known transition metal catalysed polycondensation reactions.

The oligomers and polymers of the present invention are easy to synthesize and exhibit advantageous properties. The conjugated polymers of the present invention show good processability for the device manufacture process, high solubility in organic solvents, and are especially suitable for large scale production using solution processing methods. At the same time, the co-polymers derived from monomers of the present invention and electron accepting monomers show low bandgaps, high charge carrier mobilities, high external quantum efficiencies in BHJ solar cells, good morphology when used in p/n-type blends e.g. with fullerenes, high oxidative stability, and a long lifetime in electronic devices, and are promising materials for organic electronic OE devices, especially for OPV devices with high power conversion efficiency.

The unit of formula I is especially suitable as (electron) donor unit in p-type semiconducting oligomers, homopolymers and copolymers, in particular copolymers containing both donor and acceptor units, and for the preparation of blends of p-type and n-type semiconductors which are useful for application in bulk heterojunction photovoltaic devices.

In addition, the oligomers and polymers based upon dithieno[2,3-d:2',3'-d']-s-indaceno[1,2-b:5,6-b']dithiophene show the following advantageous properties:
i) Dithieno[2,3-d:2',3'-d']-s-indaceno[1,2-b:5,6-b']dithiophene can be solubilised by two different synthetic protocols, namely tetraalkyl substitution or dialkylidene substitution. The former can be achieved by means of reacting alkyl halides with the unsubstituted core structure under alkaline conditions. Alternatively, this solublised structure can be synthesized by ring-closure of the tetraalkylated diol intermediates (see below) whereas the latter can be obtained using the method of our previous invention through Knoevenagel condensation with a variety of carbonyl compounds.
ii) Dithieno[2,3-d:2',3'-d']-s-indaceno[1,2-b:5,6-b']dithiophene can be easily functionallised at specific positions through e.g., halogenation with N-halosuccinimide, elemental halogen, or through lithiation with alkyllithium and lithium amides then reaction with a halogenation reagent, alkyl borates, trialkylstannyl chlorides or zinc chloride, as well as reacting the halide compounds with magnesium metal or an alkylmagnesium halide. These functionalised indacenodiarenes can be used to prepare a wide range of new semiconducting new oligomers, homopolymers and co-polymers through transition metal catalysed coupling methods such as Yamamoto reaction (Yamamoto et al., *Bull., Chem. Soc. Jpn.*, 1978, 51(7), 2091; Yamamoto et al., *Macromolecules*, 1992, 25(4), 1214), Suzuki-Miyaura reaction (Miyaura et al., *Chem. Rev.*, 1995, 95, 2457) and Stille reaction (Bao et al., *J. Am. Chem., Soc.*, 1995, 117(50), 12426).

iii) The optoelectronic properties of conjugated polymers vary significantly based upon the degree of extended conjugation between the consecutive repeating units and the inherent electron densities within the polymer backbones. By fusing additional aromatic rings along the long axis of s-indacenodithiophene, the π-conjugation of the resultant unit and consequently the polymers can be extended and the number of the inter-repeating unit twists in the backbone can be reduced. This is, in theory, one of the most efficient ways to modify the HOMO-LUMO levels and bandgaps in designing new semiconducting materials.

iv) In this invention, the indacenodiarenothiophene core structures are solubilised by both four alkyl groups and two alkylidene groups. Compared with the tetra-alkyl analogues, the dialkylidene substituted dithieno[2,3-d:2',3'-d']-s-indaceno[1,2-b:5,6-b']dithiophene-based oligomers and polymers are expected to possess a higher degree of planarity. This is due to the $sp^2$ carbon atoms in the alkylidenes allow the alkyl chains to take an in-plane configuration. This configuration reduces the inter-planar separation of the π-π backbones, and improves the degree of inter-molecular π-π interactions.

v) Similar to the known tetra-alkyl-s-indacenodithiophenes, tetra-alkyl and dialkylidene indacenodiarenothiophenes of this invention are also π-donor units. When polymerized with n-accepting monomers, low bandgap conjugated polymers are synthesized as potential donor candidates for use in organic photovoltaic solar cells.

vi) By fine-tuning the LUMO levels of the π-electron accepting units, the donor-acceptor materials synthesized using tetra-alkyl and dialkylidene indacenodiarenothiophenes and suitable acceptor units may exhibit electron charge transport or ambipolar charge transport behavior in field-effect transistors.

The synthesis of the oligomers, homopolymers, and copolymers can be achieved based on methods that are known to the skilled person and described in the literature, as will be further illustrated herein.

Above and below, the term "polymer" generally means a molecule of high relative molecular mass, the structure of which essentially comprises the multiple repetition of units derived, actually or conceptually, from molecules of low relative molecular mass (*Pure Appl. Chem.*, 1996, 68, 2291). The term "oligomer" generally means a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred sense according to the present invention a polymer means a compound having >1, i.e. at least 2 repeating units, preferably ≥5 repeating units, and an oligomer means a compound with >1 and <10, preferably <5, repeating units.

Above and below, in a formula showing a unit or a polymer, like formula I and its subformulae, an asterisk ("*") denotes a linkage to an adjacent unit or group, and in case of a polymer a link to an adjacent repeating unit or to a terminal group in the polymer chain.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291).

The term "small molecule" means a monomeric compound which typically does not contain a reactive group by which it can be reacted to form a polymer, and which is designated to be used in monomeric form. In contrast thereto, the term "monomer" unless stated otherwise means a monomeric compound that carries one or more reactive functional groups by which it can be reacted to form a polymer.

The terms "donor"/"donating" and "acceptor"/"accepting", unless stated otherwise, mean an electron donor or electron acceptor, respectively.

"Electron donor" means a chemical entity that donates electrons to another compound or another group of atoms of a compound. "Electron acceptor" means a chemical entity that accepts electrons transferred to it from another compound or another group of atoms of a compound. (see also U.S. Environmental Protection Agency, 2009, Glossary of technical terms, http://www.epa.gov/oust/cat/TUM-GLOSS.HTM).

The term "leaving group" means an atom or group (charged or uncharged) that becomes detached from an atom in what is considered to be the residual or main part of the molecule taking part in a specified reaction (see also *Pure Appl. Chem.*, 1994, 66, 1134).

The term "conjugated" means a compound containing mainly C atoms with $sp^2$-hybridisation (or optionally also sp-hybridisation), which may also be replaced by hetero atoms. In the simplest case this is for example a compound with alternating C—C single and double (or triple) bonds, but does also include compounds with units like 1,4-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeating units, n, means the number average degree of polymerization given as $n=M_n/M_U$, wherein $M_n$ is the number average molecular weight and $M_U$ is the molecular weight of the single repeating unit, see J. M. G. Cowie, *Polymers: Chemistry & Physics of Modern Materials*, Blackie, Glasgow, 1991.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

The term "hetero atom" means an atom in an organic compound that is not a H- or C-atom, and preferably means N, O, S, P, Si, Se, As, Te or Ge.

A carbyl or hydrocarbyl group comprising a chain of 3 or more C atoms may be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tricyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)NR°R$^{00}$, —C(=O)X°, —C(=O)R°, —NH$_2$, —NR°R$^{00}$, —SH, —SR°, —SO$_3$H, —SO$_2$R°, —OH, —NO$_2$, —CF$_3$, —SF$_5$, P-Sp-, optionally substituted silyl, or carbyl or hydrocarbyl with 1 to 40 C atoms that is optionally substituted and optionally comprises one or more hetero atoms, and is preferably alkyl, alkoxy, thiaalkyl, alkylcarbonyl, alkoxycarbonyl or al koxycarbonyloxy with 1 to 20 C atoms that is optionally fluorinated, and R°, R$^{00}$, X°, P and Sp have the meanings given above and below.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene preferably 2-thiophene, selenophene, preferably 2-selenophene, thieno [3,2-b]thiophene, indole, isoindole, benzofuran, benzothiophene, benzodithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above. Further examples of heteroaryl groups are those selected from the following formulae An alkyl or alkoxy radical, i.e. where the terminal CH$_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more CH$_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one CH$_2$ group is replaced by —O— and one by —C(O)—, these radicals are preferably neighbored. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxycarbonyl) ethyl, 3-(methoxycarbonyl)propyl, 3-(ethoxycarbonyl) propyl, 4-(methoxycarbonyl)-butyl.

An alkyl group wherein two or more CH$_2$ groups are replaced by —O— and/or —C(O)O— can be straight-chain or branched. It is preferably straight-chain and has 3 to 12

C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e. where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, in particular 1,1-difluoroalkyl, all of which are straight-chain or branched.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In another preferred embodiment of the present invention, $R^{1,2}$ are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

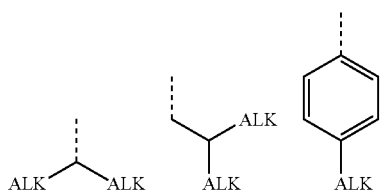

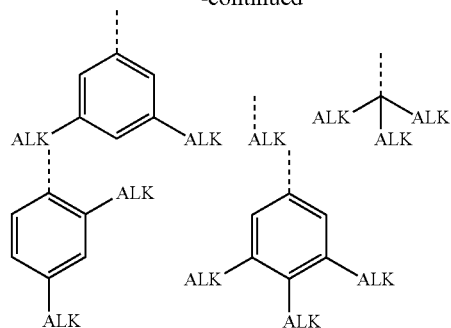

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

—$CY^1$=$CY^2$— is preferably —CH=CH—, —CF=CF— or —CH=C(CN)—.

Halogen is F, Cl, Br or I, preferably F, Cl or Br.

—CO—, —C(C=O)— and —C(O)— denote a carbonyl group, i.e.

The compounds, units and polymers according to the present invention may also be substituted with a polymerisable or crosslinkable reactive group, which is optionally protected during the process of forming the polymer. Particular preferred units polymers of this type are those comprising one or more units of formula I wherein one or more of $R^{1-4}$ denote or contain a group P-Sp-. These units and polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or crosslinkable group P is selected from $CH_2$=$CW^1$—C(O)—O—, $CH_2$=$CW^1$—C(O)—,

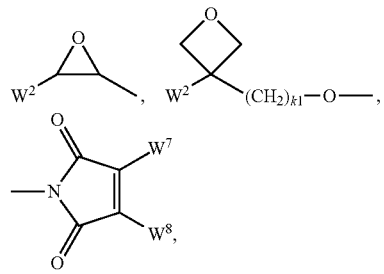

$CH_2$=$CW^2$—(O)$_{k1}$—, $CW^1$=CH—C(O)—(O)$_{k3}$—,
$CW^1$=CH—C(O)—NH—, $CH_2$=$CW^1$—C(O)—NH—,
$CH_3$—CH=CH—O—, ($CH_2$=CH)$_2$CH—OC(O)—, (CH$_2$=CH—CH$_2$)$_2$CH—O—C(O)—, (CH$_2$=CH)$_2$CH—O—, (CH$_2$=CH—CH$_2$)$_2$N—, (CH$_2$=CH—CH$_2$)$_2$N—C(O)—, HO—CW$^2$W$^3$—, HS—CW$^2$W$^3$—, HW$^2$N—, HO—CW$^2$W$^3$—NH—, CH$_2$=CH—(C(O)—O)$_{k1}$-Phe-(O)$_{k2}$—, CH$_2$=CH—(C(O))$_{k1}$-Phe-(O)$_{k2}$—, Phe-CH=CH—, HOOC—, OCN—, and W$^4$W$^5$W$^6$Si—, with W$^1$ being H, F, Cl, CN, CF$_3$, phenyl or alkyl with 1 to 5 C-atoms, in particular H, Cl or CH$_3$, W$^2$ and W$^3$ being independently of each other H or alkyl with 1 to 5 C-atoms, in particular H, methyl, ethyl or n-propyl, W$^4$, W$^5$ and W$^6$ being independently of each other Cl, oxaalkyl or oxacarbonylalkyl with 1 to 5 C-atoms, W$^7$ and W$^8$ being independently of each other H, Cl or alkyl with 1 to 5 C-atoms, Phe being 1,4-phenylene that is optionally substituted by one or more groups L as defined above, k$_1$, k$_2$ and k$_3$ being independently of each other 0 or 1, k$_3$ preferably being 1, and k$_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are CH$_2$=CH—C(O)—O—, CH$_2$=C(CH$_3$)—C(O)—O—, CH$_2$=CF—C(O)—O—, CH$_2$=CH—O—, (CH$_2$=CH)$_2$CH—O—C(O)—, (CH$_2$=CH)$_2$CH—O—,

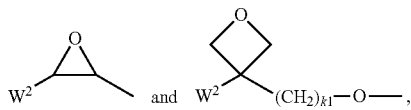

or protected derivatives thereof. Further preferred groups P are selected from the group consisting of vinyloxy, acrylate, methacrylate, fluoroacrylate, chloroacrylate, oxetan and epoxy groups, very preferably from an acrylate or methacrylate group.

Polymerisation of group P can be carried out according to methods that are known to the ordinary expert and described in the literature, for example in D. J. Broer; G. Challa; G. N. Mol, *Macromol. Chem.*, 1991, 192, 59.

The term "spacer group" is known in prior art and suitable spacer groups Sp are known to the ordinary expert (see e.g. *Pure Appl. Chem.*, 2011, 73(5), 888. The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —C(O)—, —C(O)O—, —OC(O)—, —OC(O)—O—, —S—C(O)—, —C(O)—S—, —CH=CH— or —C≡C— in such a manner that O and/or S atoms are not linked directly to one another, X' is —O—, —S—, —C(O)—, —C(O)O—, —OC(O)—, —O—C(O)O—, —C(O)—NR$^0$—, —NR$^0$—C(O)—, —NR$^0$—C(O)—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—C(O)O—, —OC(O)—CH=CH— or a single bond, R$^0$ and R$^{00}$ are independently of each other H or alkyl with 1 to 12 C-atoms, and Y$^1$ and Y$^2$ are independently of each other H, F, Cl or CN.

X' is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C— or a single bond, in particular —O—, —S—, —C≡C—, —CY$^1$=CY$^2$— or a single bond. In another preferred embodiment X' is a group that is able to form a conjugated system, such as —C≡C— or —CY$^1$=CY$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

If R$^1$ and/or R$^2$ in formula I denote substituted aryl or heteroaryl, it is preferably substituted by one or more groups L, wherein L is selected from P-Sp-, F, Cl, Br, I, —OH, —CN, —NO$_2$, —NCO, —NCS, —OCN, —SCN, —C(=O)NR$^0$R$^{00}$, —C(=O)X$^0$, —C(=O)R$^0$, —NR$^0$R$^{00}$, C(=O)OH, optionally substituted aryl or heteroaryl having 4 to 20 ring atoms, or straight chain, branched or cyclic alkyl with 1 to 20, preferably 1 to 12 C atoms wherein one or more non-adjacent CH$_2$ groups are optionally replaced, in each case independently from one another, by —O—, —S—, —NR$^0$—, —SiR$^0$R$^{00}$—, —C(=O)—, —C(=O)O—, —CY$^1$=CY$^2$— or —C≡C— in such a manner that O and/or S atoms are not linked directly to one another and which is unsubstituted or substituted with one or more F or Cl atoms or OH groups, and X$^0$ is halogen, preferably F, Cl or Br, and Y$^1$, Y$^2$, R$^0$ and R$^{00}$ have the meanings given above and below.

Preferably R$^1$ and R$^2$ denote straight-chain, branched or cyclic alkyl with 1 to 30 C atoms which is unsubstituted or substituted by one or more F atoms.

Further preferably R$^1$ and R$^2$ together with the sp$^2$-hybridised C atom of the alkylidene group form a cyclic group with 1 to 20 C atoms, preferably 1 to 10 C atoms, which is unsubstituted or substituted by one or more F atoms or by one or more C$_1$-C$_{10}$ alkyl groups.

Further preferably one of R$^1$ and R$^2$ is H and the other is different from H, and is preferably straight-chain, branched or cyclic alkyl with 1 to 30 C atoms which is unsubstituted or substituted by one or more F atoms.

Further preferably R$^1$ and/or R$^2$ are independently of each other selected from the group consisting of aryl and heteroaryl, each of which is optionally fluorinated, alkylated or alkoxylated and has 4 to 30 ring atoms.

In one preferred embodiment of the present invention R denotes H. In another preferred embodiment of the present invention R is different from H and has one of the preferred meanings of R$^1$ as given above, very preferably straight-chain, branched or cyclic alkyl with 1 to 30 C atoms which is unsubstituted or substituted by one or more F atoms.

The compounds according to the present invention include monomers, oligomers and polymers.

Oligomers and polymers according to the present invention preferably comprise one or more units of formula I as defined above and below.

Preferred polymers according to the present invention comprise one or more repeating units of formula II:

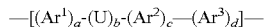   II wherein
U is a unit of formula I,
$Ar^1$, $Ar^2$, $Ar^3$ are, on each occurrence identically or differently, and independently of each other, aryl or heteroaryl that is different from U, preferably has 5 to 30 ring atoms, and is optionally substituted, preferably by one or more groups $R^S$,
$R^S$ is on each occurrence identically or differently F, Br, Cl, —CN, —NC, —NCO, —NCS, —OCN, —SCN, —C(O)$NR^0R^{00}$, —C(O)$X^0$, —C(O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, carbyl or hydrocarbyl with 1 to 40 C atoms that is optionally substituted and optionally comprises one or more hetero atoms, or P-Sp-,
$R^0$ and $R^{00}$ are independently of each other H or optionally substituted $C_{1-40}$ carbyl or hydrocarbyl, and preferably H or alkyl with 1 to 12 C-atoms,
P is a polymerisable or crosslinkable group,
Sp is a spacer group or a single bond,
$X^0$ is halogen, preferably F, Cl or Br,
a, b and c are on each occurrence identically or differently 0, 1 or 2,
d is on each occurrence identically or differently 0 or an integer from 1 to 10, wherein the polymer comprises at least one repeating unit of formula II wherein b is at least 1.

Further preferred polymers according to the present invention comprise, in addition to the units of formula I or II, one or more repeating units selected from monocyclic or polycyclic aryl or heteroaryl groups that are optionally substituted.

These additional repeating units are preferably selected of formula III

   III wherein $Ar^1$, $Ar^2$, $Ar^3$, a, b, c and d are as defined in formula II, and $A^1$ is an aryl or heteroaryl group that is different from U and $Ar^{1-3}$, preferably has 5 to 30 ring atoms, is optionally substituted by one or more groups $R^S$ as defined above and below, and is preferably selected from aryl or heteroaryl groups having electron acceptor properties, wherein the polymer comprises at least one repeating unit of formula III wherein b is at least 1.

$R^S$ preferably has one of the meanings given for $R^1$.

The conjugated polymers according to the present invention are preferably selected of formula IV:

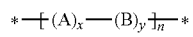   IV wherein
A is a unit of formula I,
B is a unit that is different from A and comprises one or more aryl or heteroaryl groups that are optionally substituted, and is preferably selected of formula III,
x is >0 and ≤1,
y is ≥0 and <1,
x+y is 1 and
n is an integer >1.

Preferred polymers of formula IV are selected of the following formulae

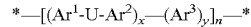   IVa

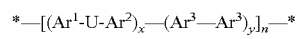   IVb

   IVc

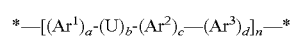   IVd

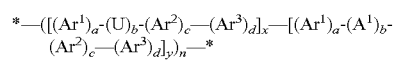   IVe wherein U, $Ar^1$, $Ar^2$, $Ar^3$, a, b, c and d have in each occurrence identically or differently one of the meanings given in formula II, $A^1$ has on each occurrence identically or differently one of the meanings given in formula III, and x, y and n are as defined in formula IV, wherein these polymers can be alternating or random copolymers, and wherein in formula IVd and IVe in at least one of the repeating units $[(Ar^1)_a\text{-}(U)_b\text{-}(Ar^2)_c\text{—}(Ar^3)_d]$ and in at least one of the repeating units $[(Ar^1)_a\text{-}(A^1)_b\text{-}(Ar^2)_c\text{—}(Ar^3)_d]$ b is at least 1.

In the polymers according to the present invention, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The polymers of the present invention include homopolymers and copolymers, like statistical or random copolymers, alternating copolymers and block copolymers, as well as combinations thereof.

Especially preferred are polymers selected from the following groups:
  Group A consisting of homopolymers of the unit U or ($Ar^1$-U) or ($Ar^1$-U-$Ar^2$) or ($Ar^1$-U-$Ar^3$) or (U-$Ar^2$—$Ar^3$) or ($Ar^1$-U-$Ar^2$—$Ar^3$), i.e. where all repeating units are identical,
  Group B consisting of random or alternating copolymers formed by identical units ($Ar^1$-U-$Ar^2$) and identical units ($Ar^3$),
  Group C consisting of random or alternating copolymers formed by identical units ($Ar^1$-U-$Ar^2$) and identical units ($A^1$),
  Group D consisting of random or alternating copolymers formed by identical units ($Ar^1$-U-$Ar^2$) and identical units ($Ar^1$-$A^1$-$Ar^2$),
wherein in all these groups U, $D^1$, $Ar^1$, $Ar^2$ and $Ar^3$ are as defined above and below, in groups A, B and C $Ar^1$, $Ar^2$ and $Ar^3$ are different from a single bond, and in group D one of $Ar^1$ and $Ar^2$ may also denote a single bond.

Further preferred are copolymers selected from the group consisting of the following subformulae IV1
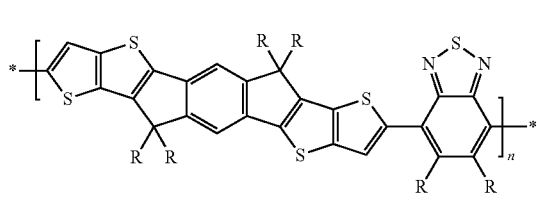
IV2
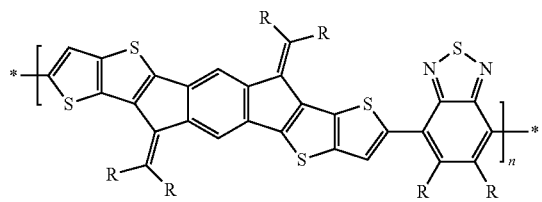
IV3
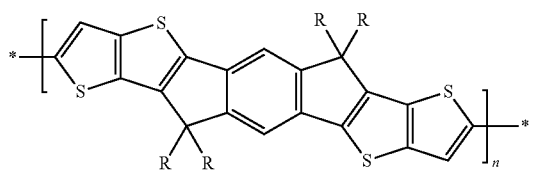
IV4
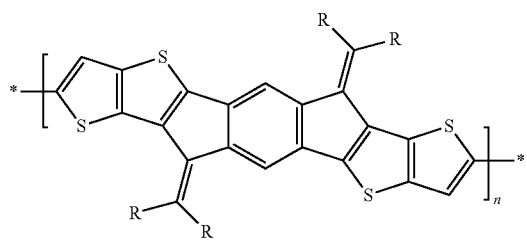
IV5
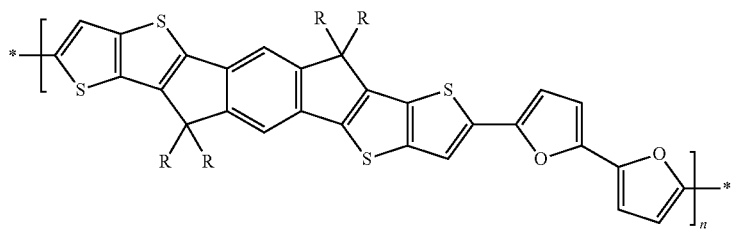
IV6
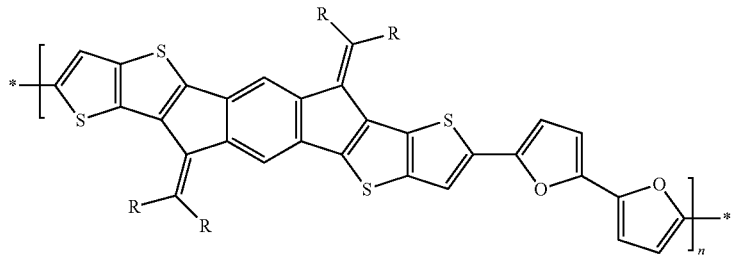
IV7
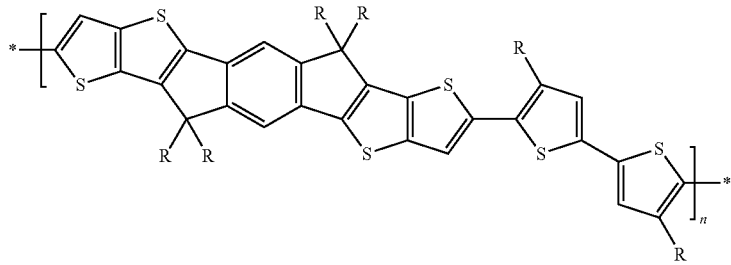
IV8
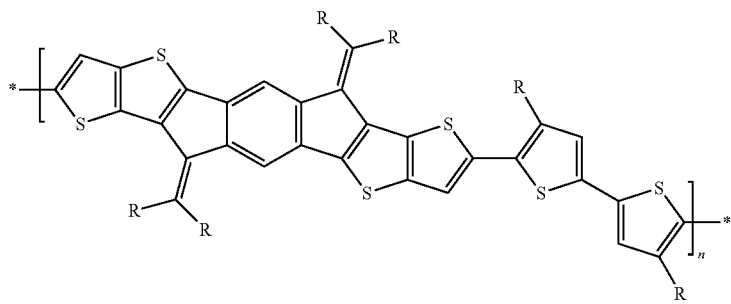

-continued
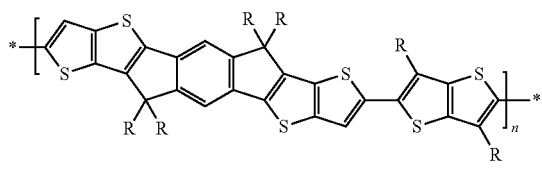
IV9
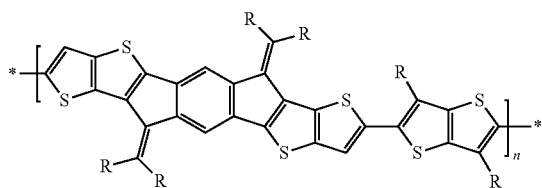
IV10
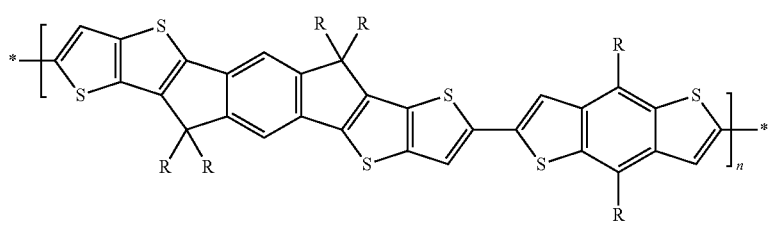
IV11
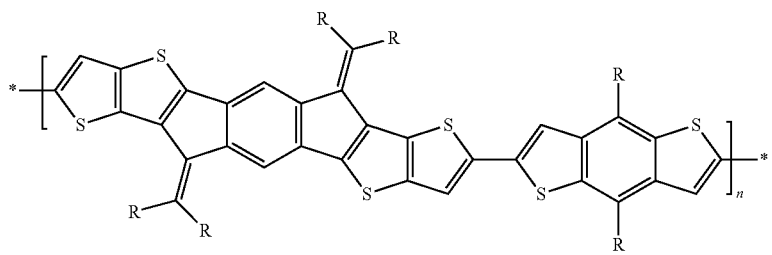
IV12
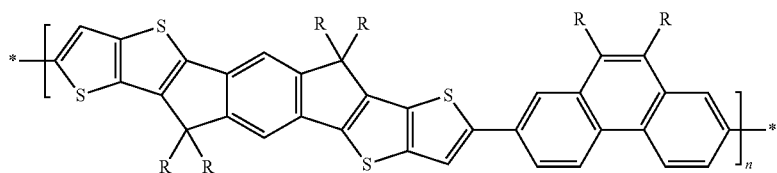
IV13
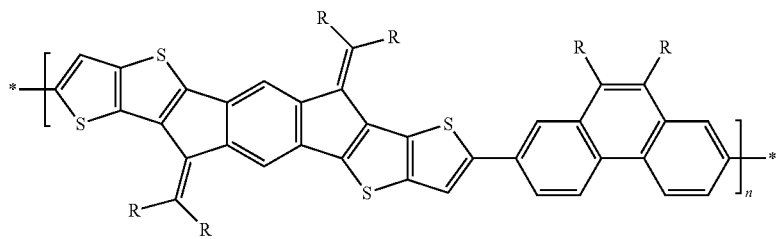
IV14 wherein R has on each occurrence identically or differently one of the meanings of $R^1$ as given in formula I.

Preferred polymers of formulae IV, IVa-IVe and IV1-IV14 are selected of formula V $$R^5\text{-chain-}R^6 \qquad\qquad V$$

wherein "chain" denotes a polymer chain of formulae IV, IVa-IVe or IV1-IV14, and $R^5$ and $R^6$ have independently of each other one of the meanings of $R^1$ as defined above, and preferably denote, independently of each other F, Br, Cl, H, —CH$_2$Cl, —CHO, —CH=CH$_2$, —SiR'R"R"', —SnR'R"R"', —BR'R", —B(OR')(OR"), —B(OH)$_2$, —ZnCl, —MgCl, —MgBr or P-Sp-, wherein P and Sp are as defined above, and R', R" and R"' have independently of each other one of the meanings of $R^0$ as defined above, and two of R', R" and R"' may also form a ring together with the hetero atom to which they are attached.

In the polymers represented by formulae IV, IVa-IVe, IV1-IV14 and V, x denotes the mole fraction of units A, y denotes the mole fraction of units B, and n denotes the degree of polymerisation or total number of units A and B. These formulae includes block copolymers, random or statistical copolymers and alternating copolymers of A and B, as well as homopolymers of A for the case when x is >0 and y is 0.

Monomers according to the present invention preferably comprise a unit of formula I as defined above and below, and one or more reactive functional groups which are attached to the unit of formula I and which can be reacted to form a polymer.

Preferably the monomers are selected of formula VI $$R^9\text{—Ar}^1\text{-U-Ar}^2\text{—}R^{10} \qquad\qquad VI$$

wherein U, $Ar^1$ and $Ar^2$ have the meanings of formula II and V, or one of the preferred meanings as described above and below, and $R^9$ and $R^{10}$ independently of each other denote F, Br, Cl, —CH$_2$Cl, —CHO, —CH=CH$_2$, —SiR'R"R"', —SnR'R"R"', —BR'R", —B(OR')(OR"), —B(OH)$_2$, —ZnCl, —MgCl, or —MgBr, wherein R', R" and R"' have independently of each other one of the meanings of $R^0$ as defined above, and two of R', R" and R"' may also form a ring together with the hetero atom to which they are attached.

Especially preferred are monomers of formula VI wherein $R^9$ and $R^{10}$ are, preferably independently of each other, selected from the group consisting of Cl, Br, I, O-tosylate, O-triflate, O-mesylate, O-nonaflate, —SiMe$_2$F, —SiMeF$_2$, —O—SO$_2Z^1$, —B(OZ$^2$)$_2$—CZ$^3$=C(Z$^3$)$_2$, —C≡CH, —C≡CSi(Z$^1$)$_3$, —ZnX and —Sn(Z$^4$)$_3$, wherein $Z^{1-4}$ are selected from the group consisting of alkyl and aryl, each being optionally substituted, and two groups $Z^2$ may also form a cyclic group, and X is a halogen atom.

Oligomeric compounds according to the present invention are preferably selected of formula VII

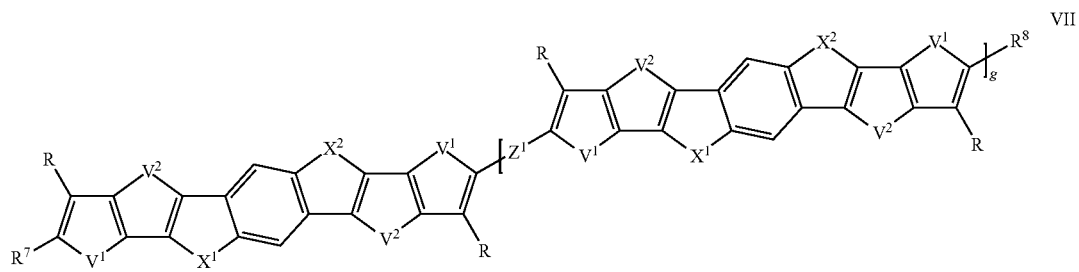

wherein R, $V^1$, $V^2$, $X^1$, $X^2$, $Y^1$ and $Y^2$ are as defined in formula I, $Z^1$ denotes a single bond, (CY$^1$=CY$^2$)$_h$, (C≡C)$_h$, wherein h=1 or 2, or $Ar^5$, wherein $Ar^5$ has one of the meanings of $Ar^1$ or $Ar^3$ as given in formula II or one of the preferred meanings of $Ar^1$ or $Ar^3$ as given above and below, $R^7$ and $R^8$ independently of each other denote H, F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —O—C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, P-Sp-, or optionally substituted silyl, carbyl or hydrocarbyl with 1 to 40 C atoms that is optionally substituted and optionally comprises one or more hetero atoms, and wherein one or more C atoms are optionally replaced by a hetero atom, and $R^0$, $R^{00}$ and $X^0$ are as defined in formula II, and g is 1, 2 or 3.

Especially preferred oligomeric compounds of formula VII are selected from the following formulae:

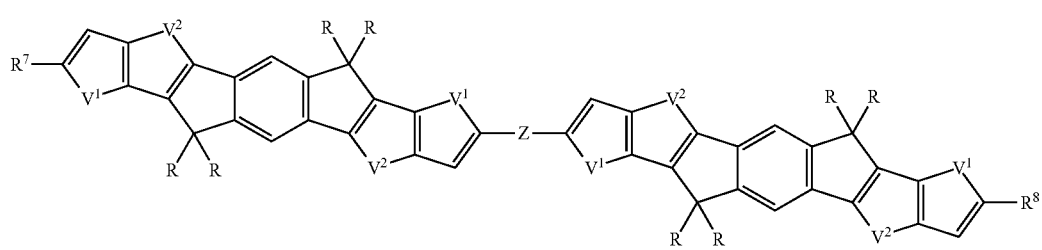

VIIb

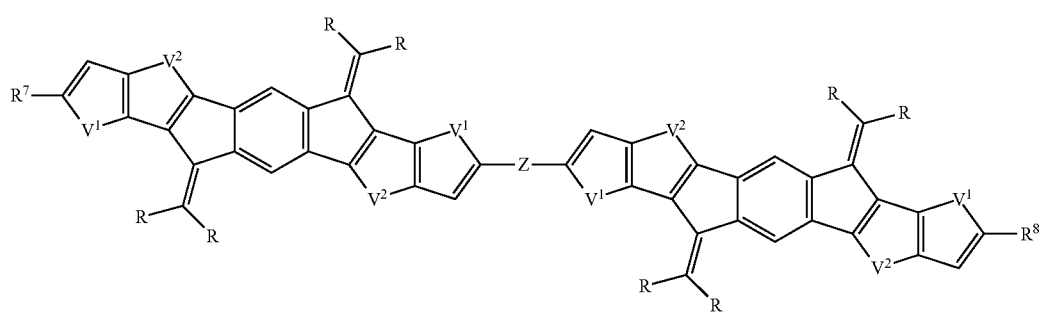

wherein R, $V^1$, $V^2$, $R^7$ and $R^8$ are as defined in formula VII, and Z has one of the meanings of $Z^1$ as given in formula VII.

Especially preferred are repeating units, monomers, oligomers and polymers of formulae I, II, Ill, IV, IVa-IVe, V, VI, VII and their subformulae, wherein one or more of $Ar^1$, $Ar^2$ and $Ar^3$ denote aryl or heteroaryl, preferably having electron donor properties, selected from the group consisting of the following formulae (D1)
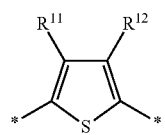

(D2)
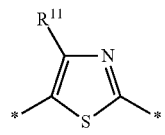

(D3)
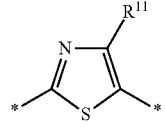

(D4)
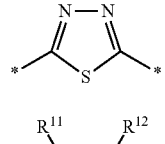

(D5)
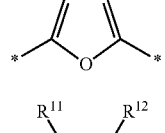

(D6)
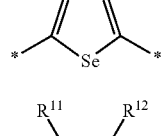

(D7)
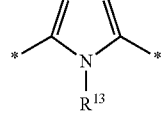

(D8)
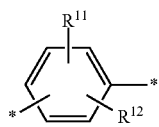

(D9)
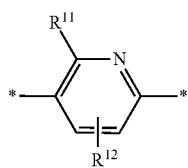

(D10)
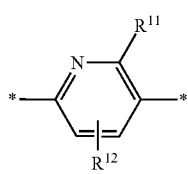

(D11)
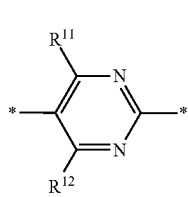

(D12)
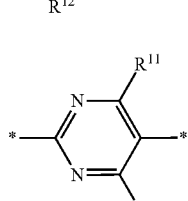

(D13)
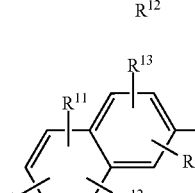

(D14)
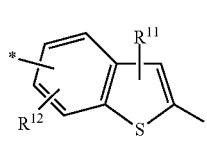

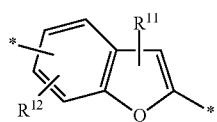 (D15)
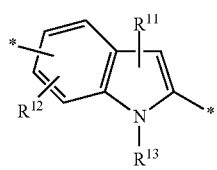 (D16)
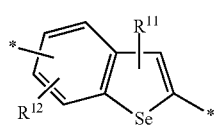 (D17)
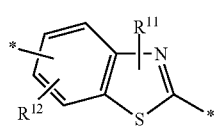 (D18)
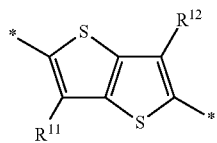 (D19)
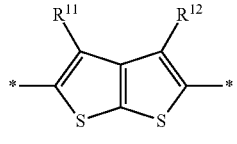 (D20)
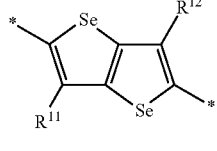 (D21)
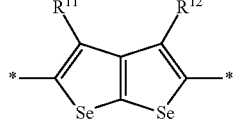 (D22)
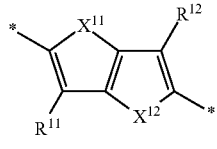 (D23)
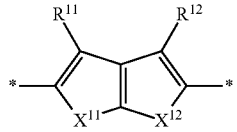 (D24)
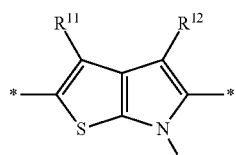 (D25)
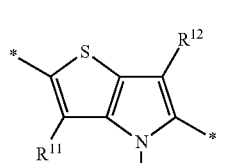 (D26)
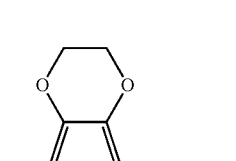 (D27)
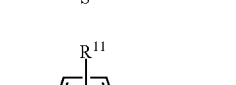 (D28)
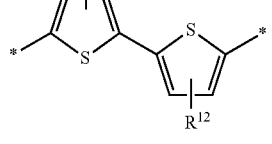 (D29)
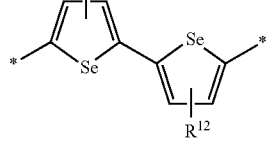 (D30)
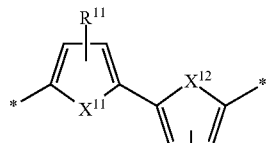 (D31)
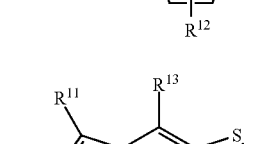 (D32)

(D33) 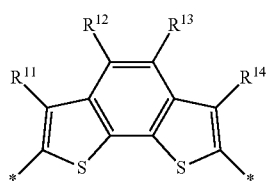
(D34) 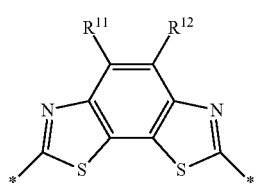
(D35) 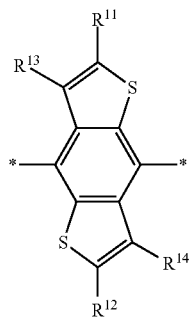
(D36) 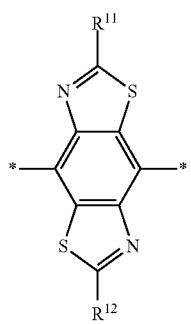
(D37) 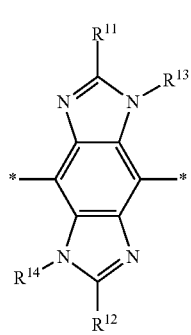
(D38) 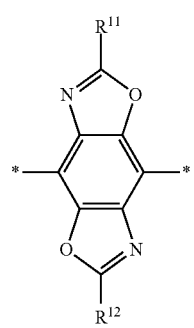
(D39) 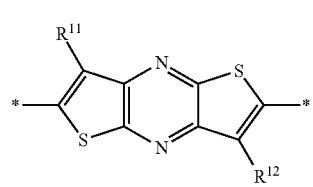
(D40) 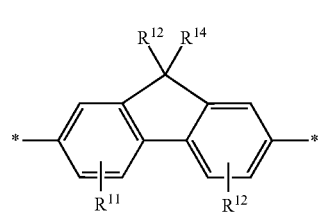
(D41) 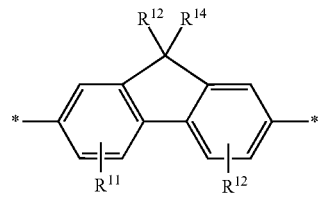
(D42) 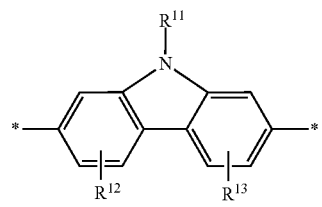
(D43) 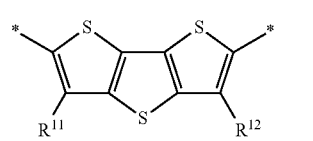
(D44) 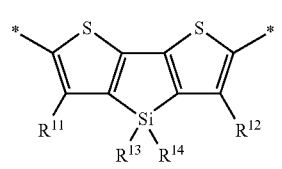
(D45)

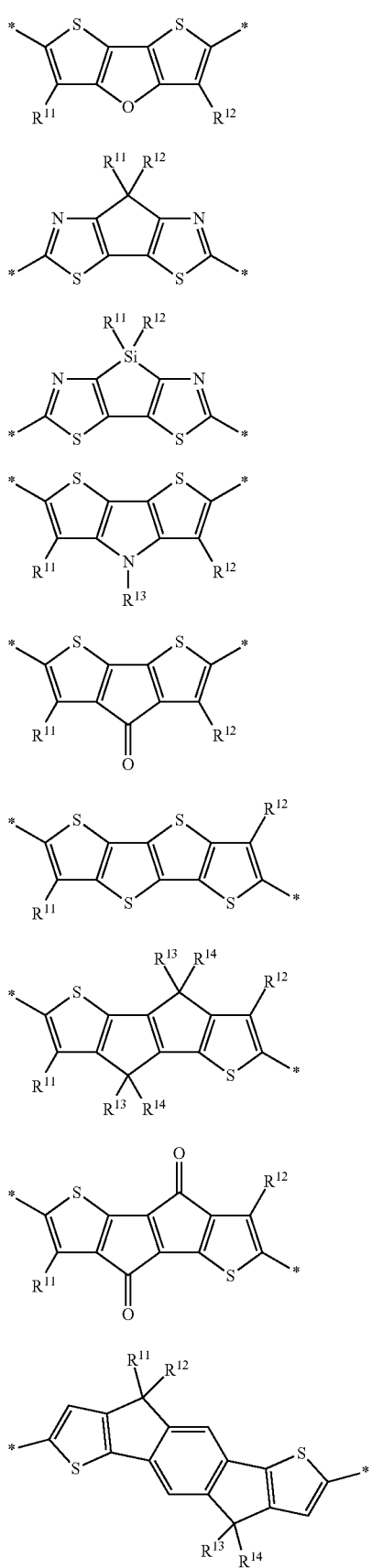
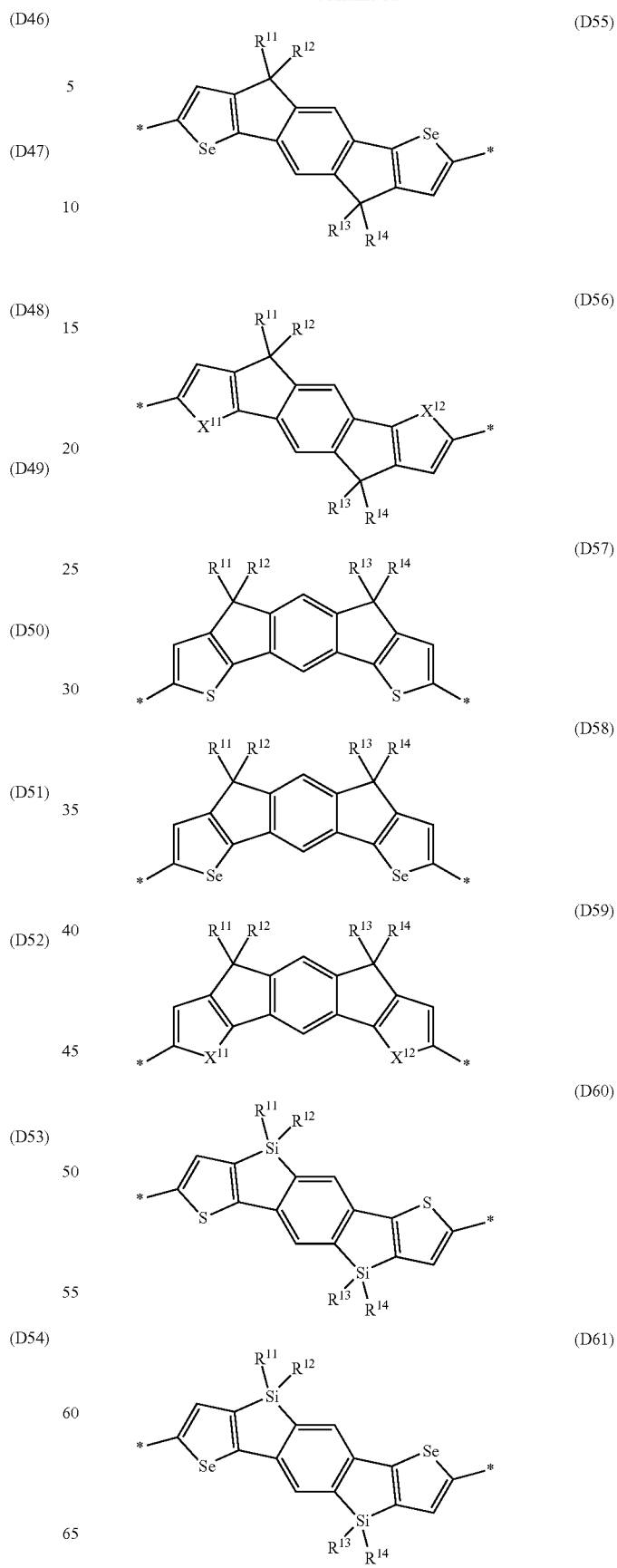

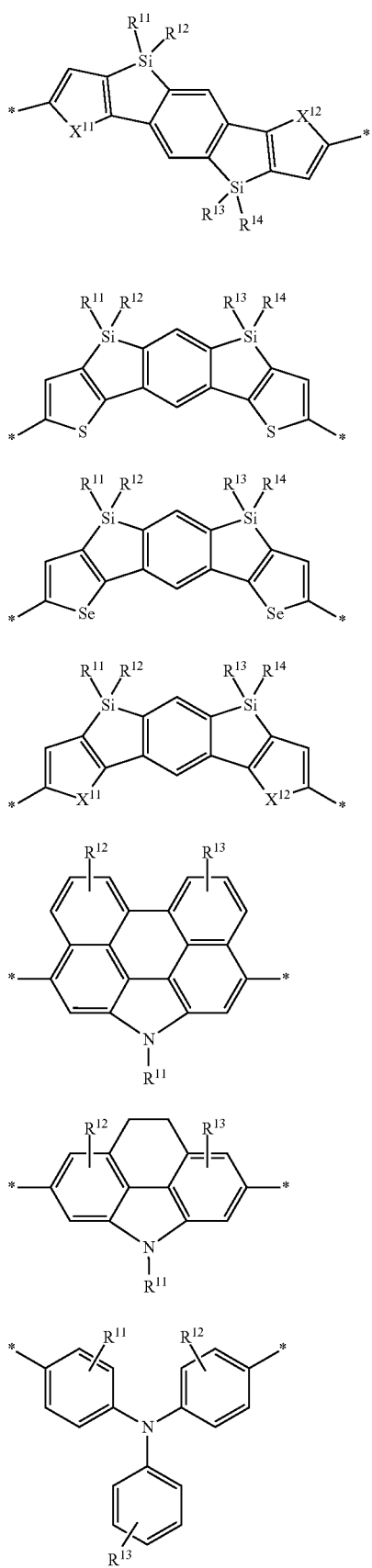
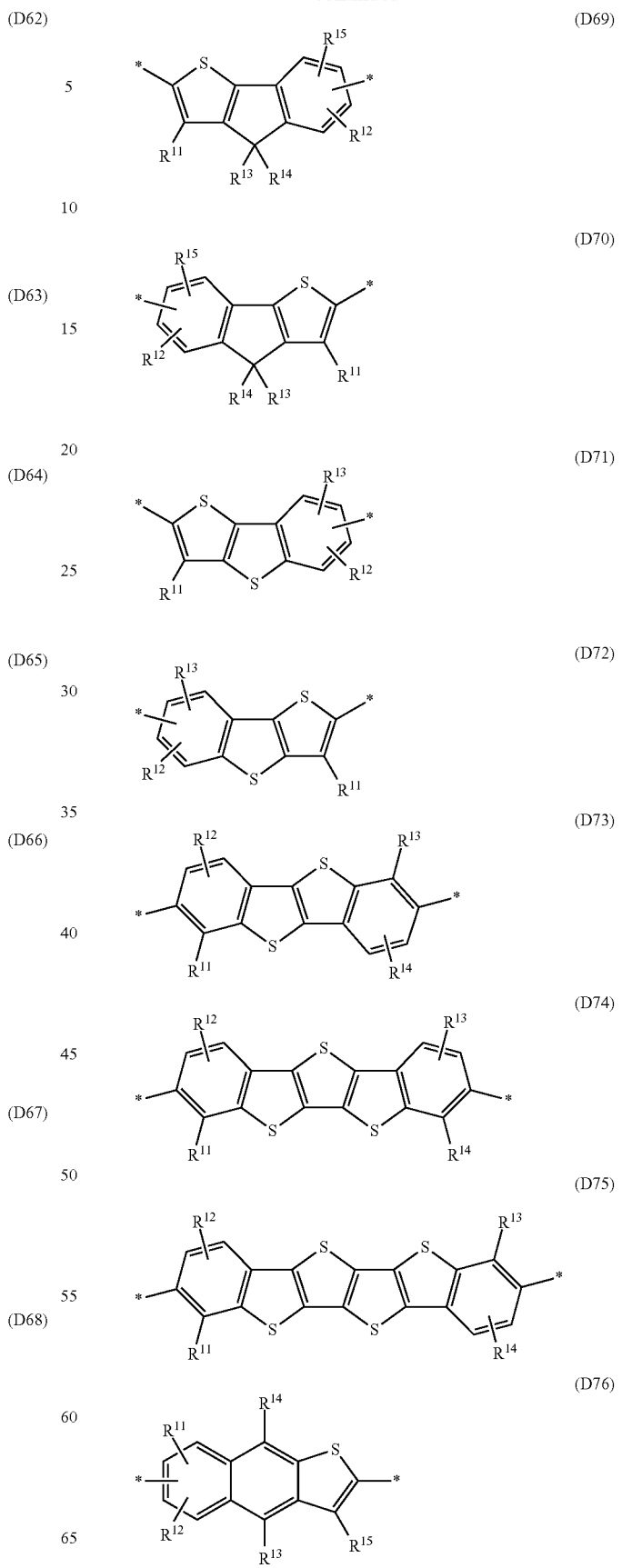

-continued (D77) 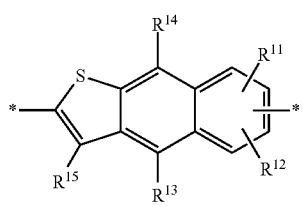

(D78) 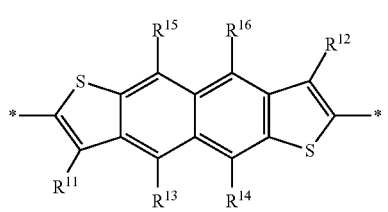

(D79) 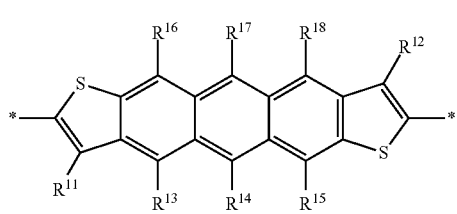

(D80) 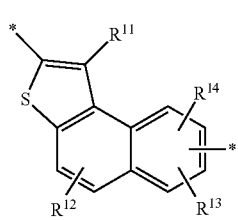

(D81) 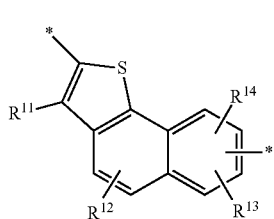

(D82) 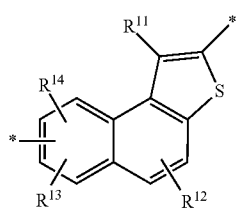

(D83) 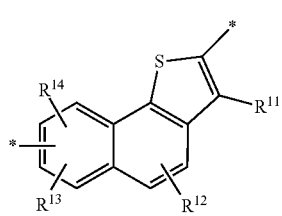

-continued (D84) 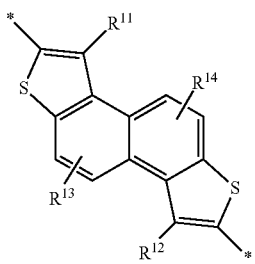

(D85) 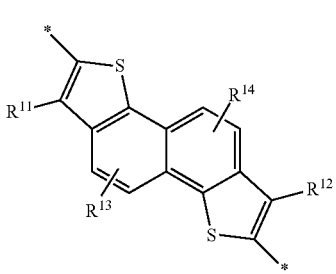

(D86) 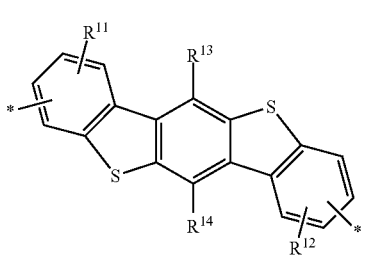

(D87) 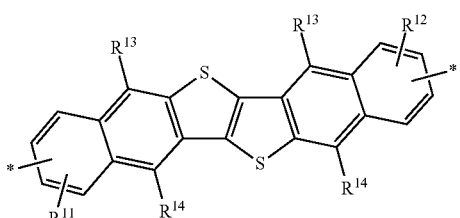

(D88) 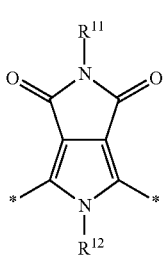

wherein one of $X^{11}$ and $X^{12}$ is S and the other is Se, and $R^{11}$, $R^{12}$, $R^{13}$, $R^{14}$, $R^{15}$, $R^{16}$, $R^{17}$ and $R^{18}$ independently of each other denote H or have one of the meanings of R as defined above and below.

Especially preferred are repeating units, monomers, oligomers and polymers of formulae I, II, III, IV, IVa-IVe, V, VI, VII and their subformulae, wherein one or more of $Ar^3$ and $A^1$ denote aryl or heteroaryl, preferably having electron acceptor properties, selected from the group consisting of the following formulae (A1) 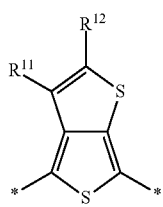
(A2) 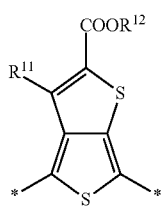
(A3) 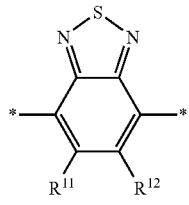
(A4) 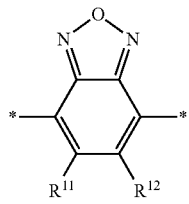
(A5) 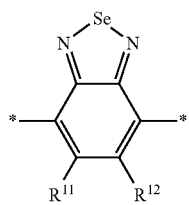
(A6) 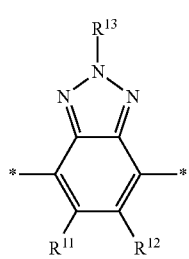
(A7) 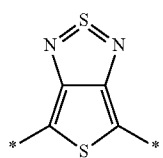
(A8) 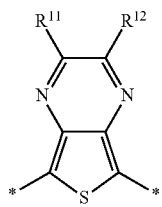
(A9) 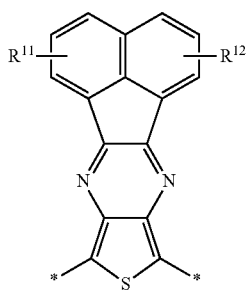
(A10) 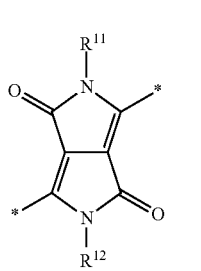
(A11) 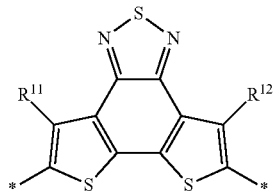
(A12) 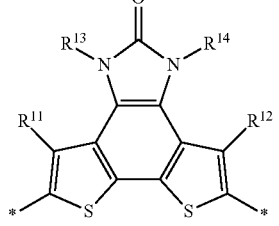
(A13) 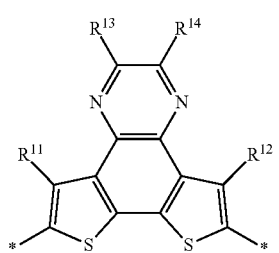

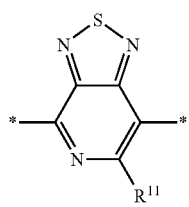
(A14)
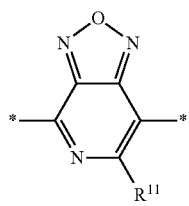
(A15)
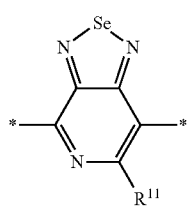
(A16)
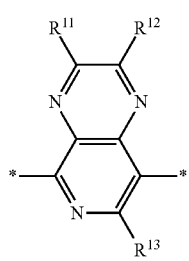
(A17)
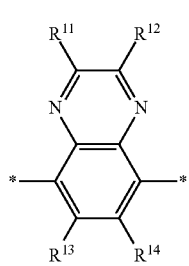
(A18)
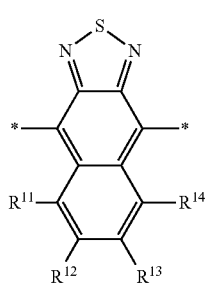
(A19)
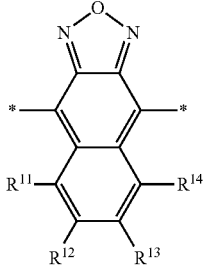
(A20)
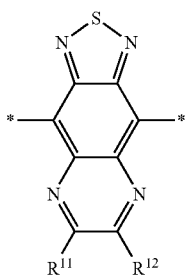
(A21)
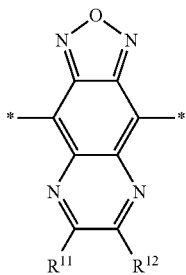
(A22)
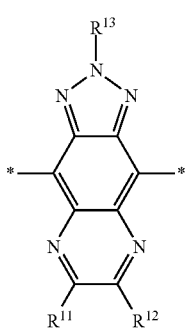
(A23)
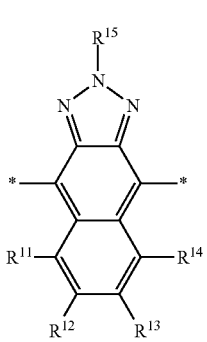
(A24)

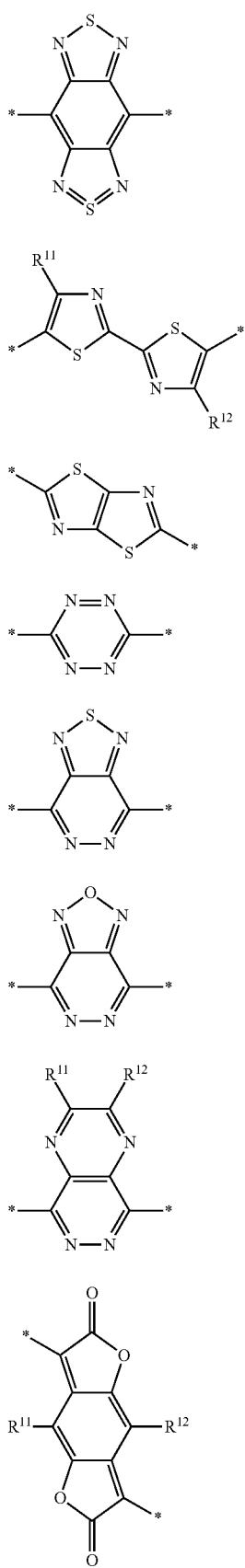
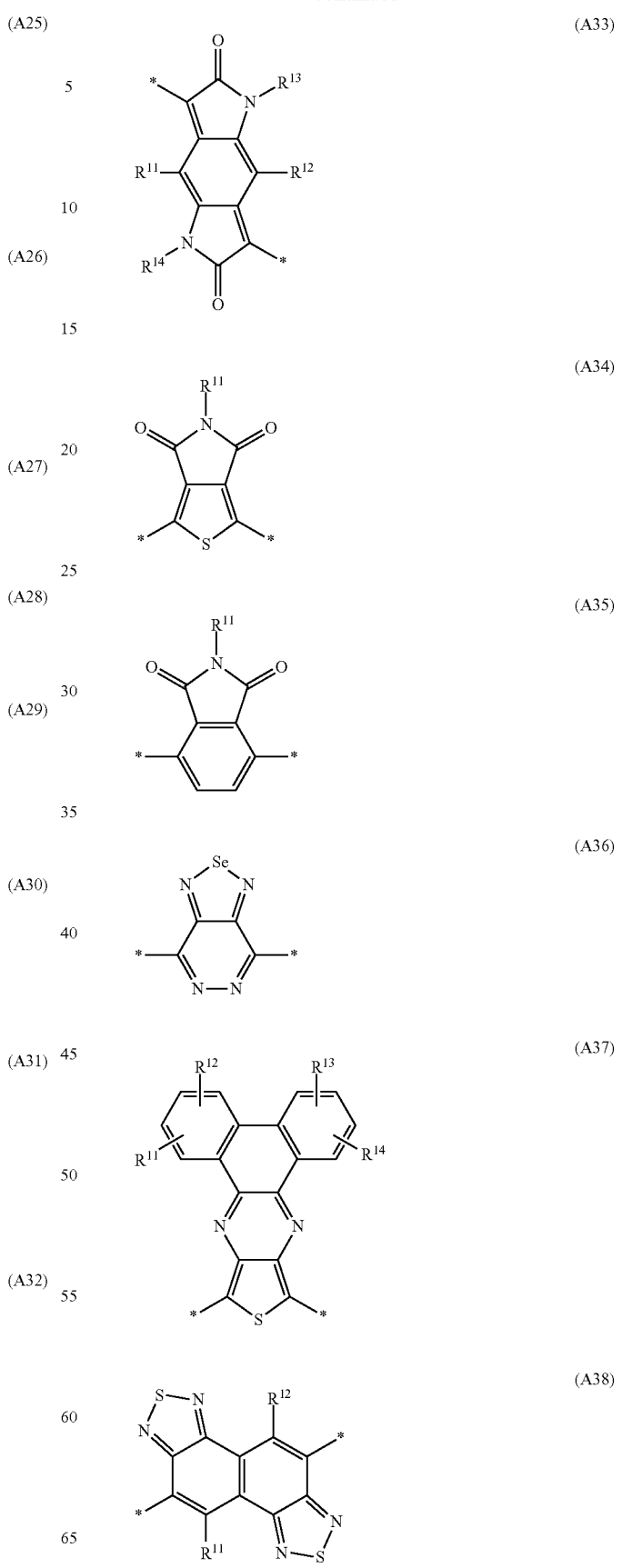

(A39)
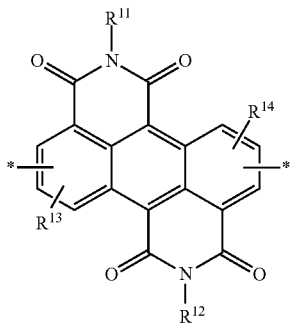

(A40)
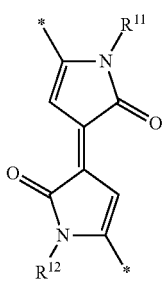

(A41)
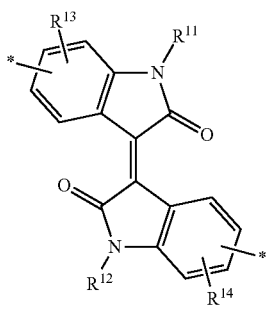

(A42)
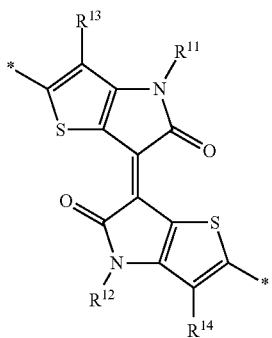

wherein one of $X^{11}$ and $X^{12}$ is S and the other is Se, and $R^{11}$, $R^{12}$, $R^{13}$, $R^{14}$ and $R^{15}$ independently of each other denote H or have one of the meanings of R as defined above and below.

Very preferred are repeating units, monomers, oligomers, and polymers of formulae I, IA, II, Ill, IV, IVa-IVe, IV1-IV14, V, VI, VII and their subformulae selected from the following list of preferred embodiments:

y is ≥0 and ≤1,
b=d=1 and a=c=0, preferably in all repeating units,
a=b=c=d=1, preferably in all repeating units,
a=b=d=1 and c=0, preferably in all repeating units,
a=b=c=1 and d=0, preferably in all repeating units,
a=c=2, b=1 and d=0, preferably in all repeating units,
a=c=2 and b=d=1, preferably in all repeating units, n is at least 5, preferably at least 10, very preferably at least 50, and up to 2,000, preferably up to 500.
$M_w$ is at least 5,000, preferably at least 8,000, very preferably at least 10,000, and preferably up to 300,000, very preferably up to 100,000,
$V^1$ and $V^2$ are S,
$V^1$ and $V^2$ are Se,
$V^1$ and $V^2$ are O,
$V^1$ and $V^2$ are Te,
$V^1$ and $V^2$ are $NR^z$,
$X^1$ and $X^2$ are $CR^1R^2$,
$X^1$ and $X^2$ are $C=CR^1R^2$,
$V^1$ and $V^2$ are S, and $X^1$ and $X^2$ are $CR^1R^2$ or $C=CR^1R^2$,
one of $R^1$ and $R^2$ is H and the other is different from H,
$R^1$ and $R^2$ are different from H,
$R^1$ and $R^2$ are CN,
$R^1$ and/or $R^2$ are independently of each other selected from the group consisting of primary alkyl with 1 to 30 C atoms, secondary alkyl with 3 to 30 C atoms, and tertiary alkyl with 4 to 30 C atoms, wherein in all these groups one or more H atoms are optionally replaced by F,
$R^1$ and $R^2$ together with the alkylidene C atom form a cyclic group with 1 to 20, preferably 1 to 10 C atoms, which is unsubsituted or substituted by one or more F atoms or by one or more $C_1$-$C_{10}$ alkyl groups,
$R^1$ and/or $R^2$ are independently of each other selected from the group consisting of aryl and heteroaryl, each of which is optionally fluorinated, alkylated or alkoxylated and has 4 to 30 ring atoms,
$R^1$ and/or $R^2$ are independently of each other selected from the group consisting of primary alkoxy or sulfanylalkyl with 1 to 30 C atoms, secondary alkoxy or sulfanylalkyl with 3 to 30 C atoms, and tertiary alkoxy or sulfanylalkyl with 4 to 30 C atoms, wherein in all these groups one or more H atoms are optionally replaced by F,
$R^1$ and/or $R^2$ are independently of each other selected from the group consisting of aryloxy, heteroaryloxy, each of which is optionally alkylated or alkoxylated and has 4 to 30 ring atoms,
$R^1$ and/or $R^2$ are independently of each other selected from the group consisting of alkylcarbonyl, alkoxycarbonyl and alkylcarbonyloxy, all of which are straight-chain or branched, are optionally fluorinated, and have from 1 to 30 C atoms,
$R^o$ and $R^{oo}$ are selected from H or $C_1$-$C_{10}$-alkyl,
$R^5$ and $R^6$ are selected from H, halogen, —$CH_2Cl$, —CHO, —CH=$CH_2$—SiR'R"R"', —SnR'R"R"', —BR'R", —B(OR')(OR"), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl,
$R^9$ and $R^{10}$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^4$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group, very preferably from Br,
$R^7$ and $R^8$ denote H,
$R^7$ and/or $R^8$ denote F,
e and f are 0.

The polymers of the present invention can be synthesized according to or in analogy to methods that are known to the skilled person and are described in the literature. Other synthesis methods can be taken from the examples. For example, the polymers can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred.

The monomers which are polymerised to form the repeat units of the polymers, can be prepared according to methods which are known to the person skilled in the art.

Preferably the polymers are prepared from monomers of formula VI or its preferred embodiments as described above and below.

Another aspect of the invention is a process for preparing a polymer by coupling one or more identical or different monomeric units of formula I or monomers of formula VI with each other and/or with one or more comonomers in a polymerisation reaction, preferably in an aryl-aryl coupling reaction.

Suitable and preferred comonomers are selected from the following formulae $$R^9—Ar^3—R^{10} \quad \quad C1$$

$$R^9-A^1-R^{10} \quad \quad C2$$

wherein $Ar^3$ has one of the meanings of formula II or one of the preferred meanings given above and below, $A^1$ has one of the meanings of formula III or one of the preferred meanings given above and below, and $R^9$ and $R^{10}$ have one of the meanings of formula V different from H, and preferably denote reactive functional groups like for example halogen, stannyl and boronate groups as defined in formula V.

Preferred methods for polymerisation are those leading to C—C-coupling or C—N-coupling, like Suzuki polymerisation, as described for example in WO 00/53656, Yamamoto polymerisation, as described in for example in T. Yamamoto et al., *Prog. Polym. Sci.*, 1993, 17, 1153-1205 or in WO 2004/022626 A1, and Stille coupling. For example, when synthesizing a linear polymer by Yamamoto polymerisation, monomers as described above having two reactive halide groups $R^9$ and $R^{10}$ is preferably used. When synthesizing a linear polymer by Suzuki polymerisation, preferably a monomer as described above is used wherein at least one reactive group $R^9$ or $R^{10}$ is a boronic acid or boronic acid derivative group.

Suzuki polymerisation may be used to prepare homopolymers as well as statistical, alternating and block random copolymers. Statistical or block copolymers can be prepared for example from the above monomers of formula V wherein one of the reactive groups $R^9$ and $R^{10}$ is halogen and the other reactive group is a boronic acid or boronic acid derivative group. The synthesis of statistical, alternating and block copolymers is described in detail for example in WO 03/048225 A2 or WO 2005/014688 A2.

Suzuki polymerisation employs a Pd(0) complex or a Pd(II) salt. Preferred Pd(0) complexes are those bearing at least one phosphine ligand such as $Pd(Ph_3P)_4$. Another preferred phosphine ligand is tris(ortho-tolyl)phosphine, i.e. $Pd(o-Tol)_3$. Preferred Pd(II) salts include palladium acetate, i.e. $Pd(OAc)_2$. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl) nickel(0).

As alternatives to halogens as described above, leaving groups of formula —O—$SO_2Z^1$ can be used wherein $Z^1$ is as described above. Particular examples of such leaving groups are tosylate, mesylate and triflate.

Especially suitable and preferred synthesis methods of the repeating units, monomers, and polymers of formula I, II, III, IV, V and VI are illustrated in the synthesis schemes shown hereinafter, wherein $R^1$, $R^2$, $R^3$, $R^4$ and n are as defined in formula I, II, IV and IV5, and R is an aryl or alkyl group.

There are two preferred synthetic routes leading to dithieno[2,3-d:2',3'-d']-s-indaceno[1,2-b:5,6-b']dithiophene unit of the present invention. Both routes go through a common intermediate 3 which was synthesised via the cross-coupling of 2-functionallised thieno[3,2-b]thiophene with diethyl 2,5-dibromoterephthalate (2), as shown in Scheme 1. In Route A, terephthalate 3 is treated with alkylaryllithium or alkylarylmagnesium halide to yield the diol 5, which is subsequently double ring-closed upon treating with an acid, to yield directly the tetrasubstituted derivative.

Scheme 1

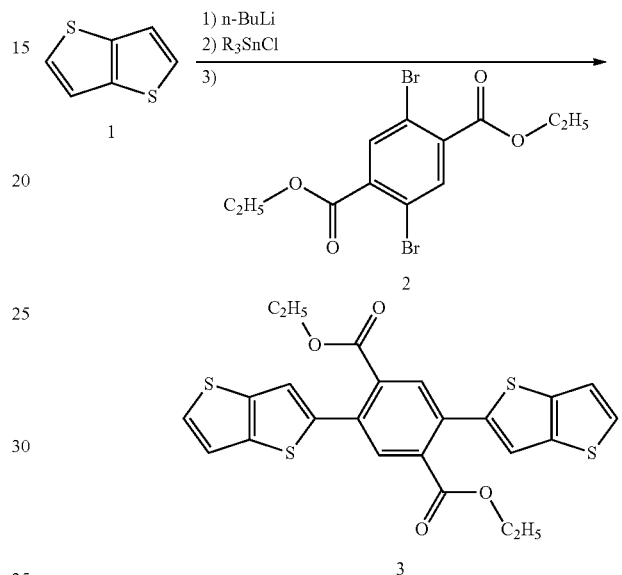

Route A

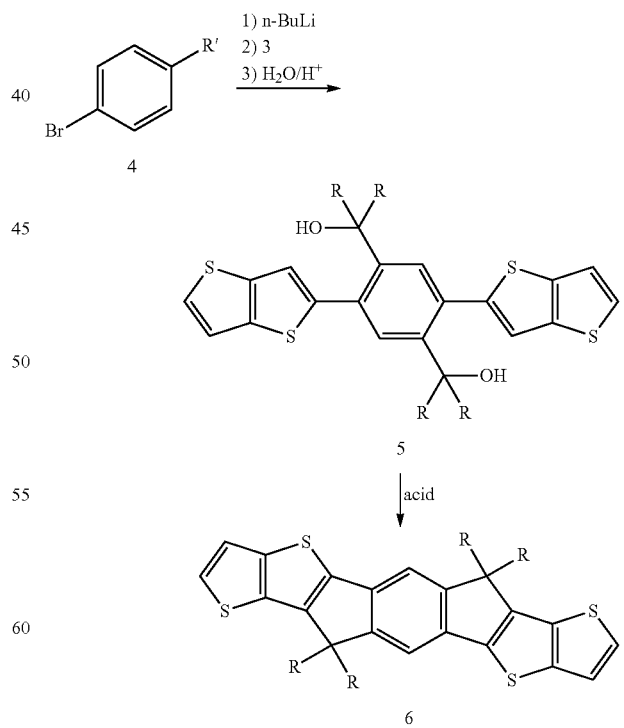

R = alkyl substituted aryls (e.g. 4-alkylphenyl)

In the second approach, Route B (as shown in Scheme 2), diester 3 is hydrolysed to terephthalic acid (7), which is converted to the corresponding terephthaloyl dichloride by reacting with oxalyl chloride or thionyl chloride. Terephthaloyl dichloride is then double-ring-closed to the quinone form 8, which is then reduced to the unsubstituted core structure 9.

Dithieno[2,3-d:2',3'-d']-s-indaceno[1,2-b:5,6-b']dithiophene 9 can be tetra-alkylated with alkyl halides under basic conditions. It can also be solubilised using alkylidene groups by reacting 9 with an aldehyde or a ketone.

The preferred functionallisation of the tetra-alkyl and dialkylidene derivatives 10 and 11 leads to two types of monomers, as shown in Scheme 3. These functionallisation

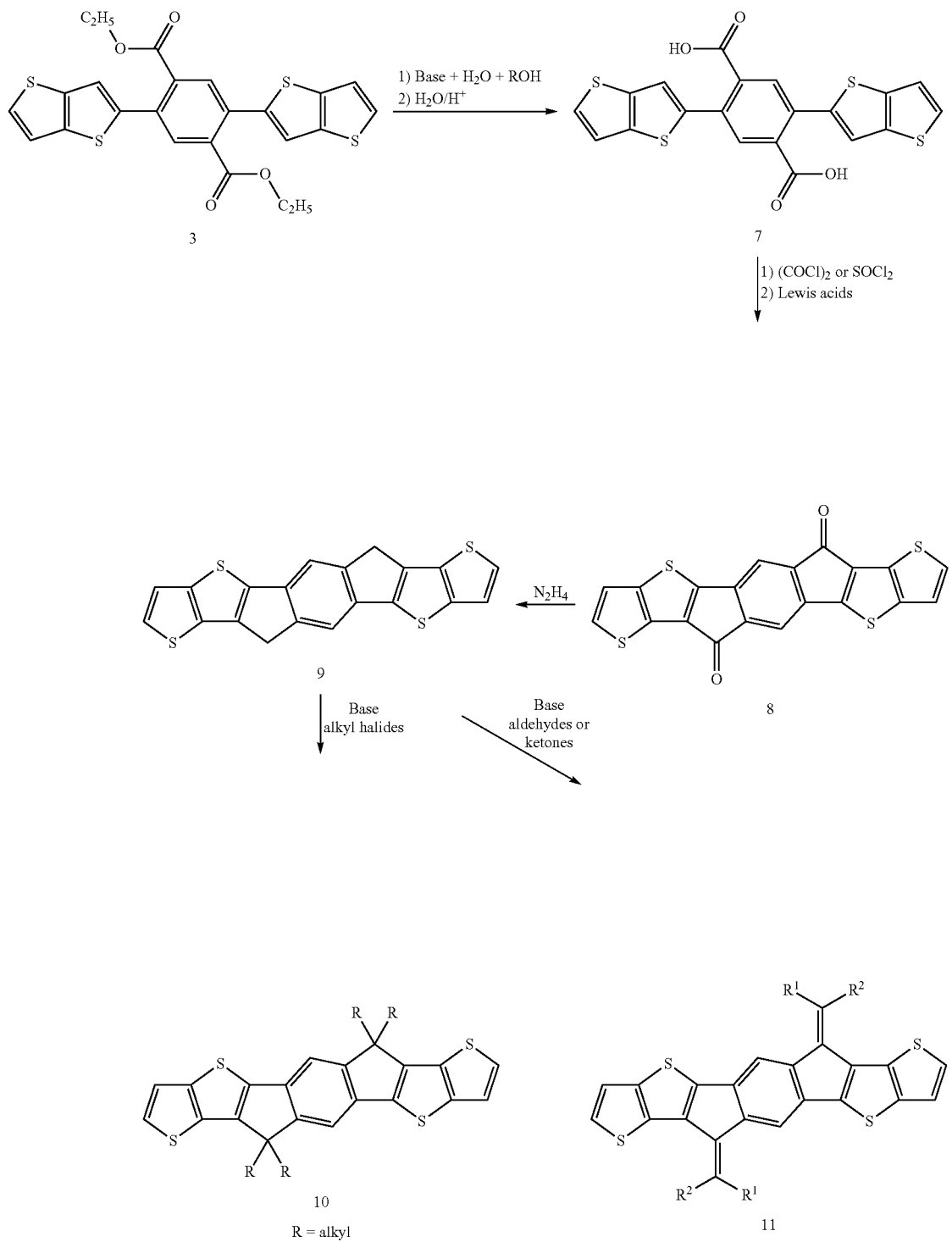

reactions generally mean but not limited to, e.g., bromination with N-bromosuccinimide or elemental bromine, or lithiation with organolithium reagents then reacting with alkyl boronic esters to yield the diboronic acids and esters, or with trialkylstannyl chlorides to yield the distannanes.

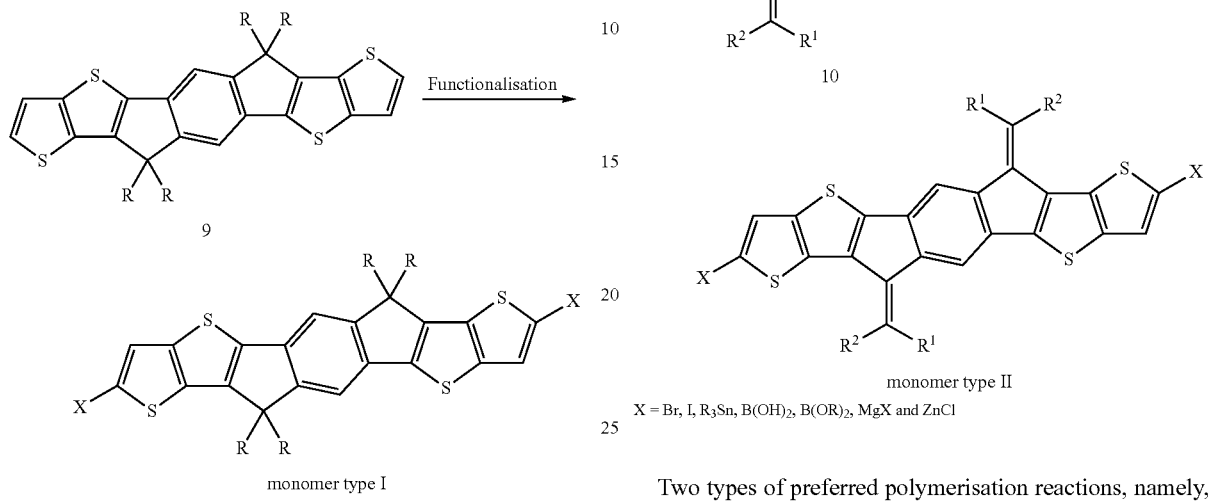

monomer type II

X = Br, I, $R_3Sn$, $B(OH)_2$, $B(OR)_2$, MgX and ZnCl

Two types of preferred polymerisation reactions, namely, Suzuki and Stille polycondensations are shown in Scheme 4.

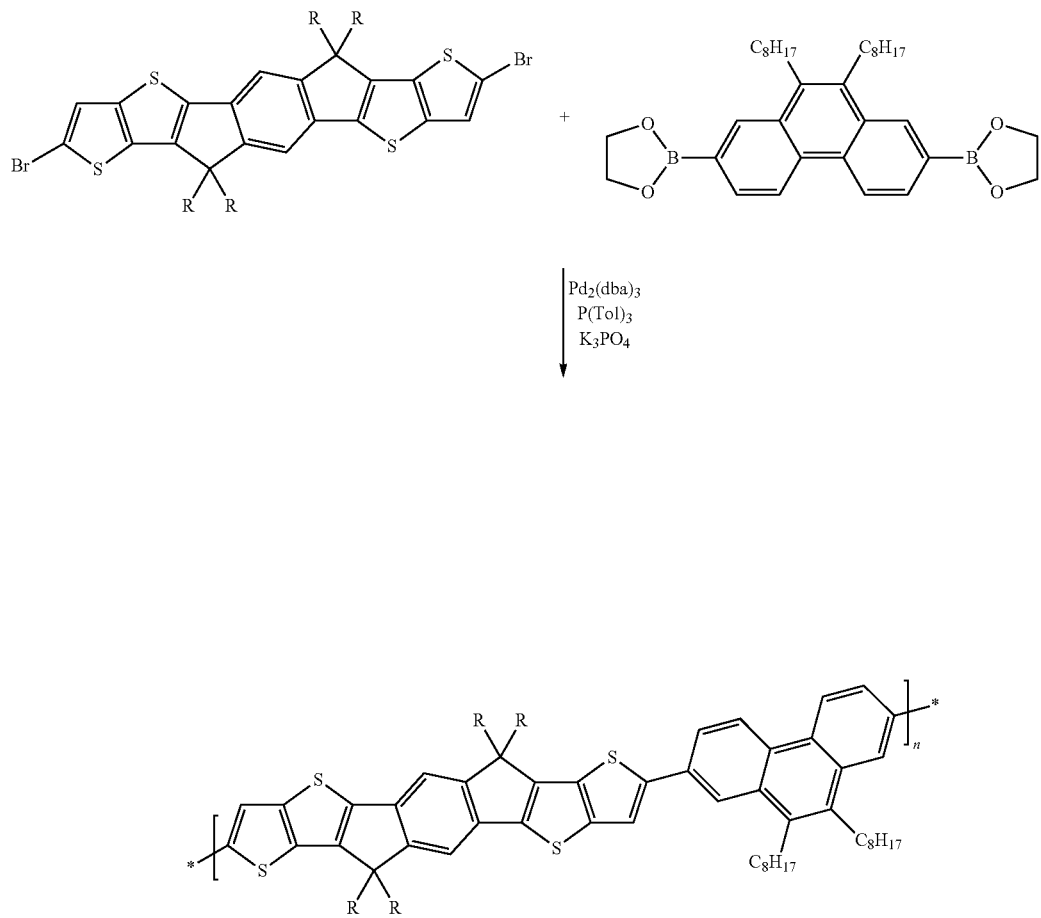

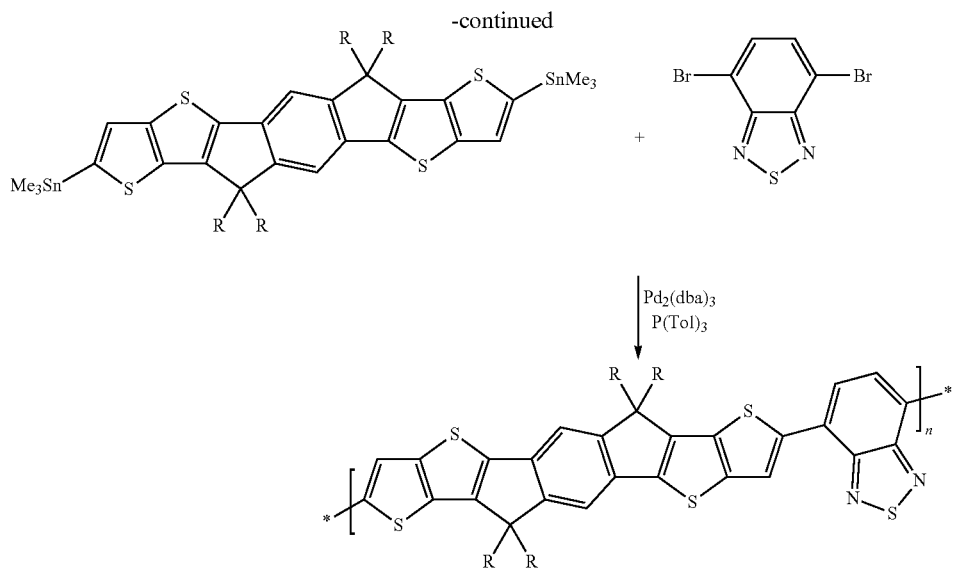

The novel methods of preparing monomers and polymers as described above and below are another aspect of the invention.

The oligomers and polymers according to the present invention can also be used in mixtures or polymer blends, for example together with monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising oligomers, polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxy-benzene, 1-methylnaphthalene, N-methylpyrrolidinone, 3-fluorobenzotrifluoride, benzotrifluoride, benzotrifluoride, diosane, trifluoromethoxy-benzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the oligomers or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "*Solvents*, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The oligomers and polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing.

Ink-jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a oligomer or polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the oligomer or polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymer blends and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The oligomers and polymers to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting oligomers, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising an oligomer, polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising an oligomer, polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the oligomer or polymer according to the present invention is preferably used as photoactive layer. This implies the use in a formulation that comprises or contains, more preferably consists essentially of, very preferably exclusively of, a p-type (electron donor) semiconductor and an n-type (electron acceptor) semiconductor. The p-type semiconductor is constituted by a compound, preferably a polymer according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, *Science*, 1995, 270, 1789 and having the structure shown below, or an structural analogous compound with e.g. a $C_{70}$ fullerene group ($C_{70}$PCBM), or a polymer (see for example Coakley, K. M. and McGehee, M. D. *Chem. Mater.*, 2004, 16, 4533).

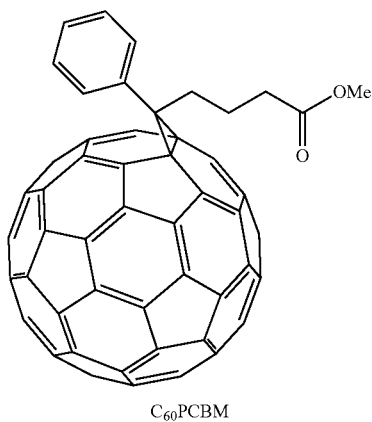 [SMILES: COC(=O)CCCC1(c2ccccc2)C23C=C4Cc5cc6cc7c8c9c(cc%10cc%11c%12c(c%13c%14c%15c(c4c5c4c6c8c(c%154)c4c9c%10c%12c%144)C%1321)C(=C3)C%11)C7]

$C_{60}$PCBM

A blend or mixture of a polymer according to the present invention with a $C_{60}$ or $C_{70}$ fullerene or modified fullerene like $C_{60}$PCBM or $C_{70}$PCBM is the preferred material combination to be used in formulations for OPV devices. Preferably the ratio polymer:fullerene is from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the oligomers, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a $C_{60}$ or $C_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
optionally a substrate,
a high work function electrode, preferably comprising a metal oxide, like for example ITO, serving as anode,
an optional conducting polymer layer or hole transport layer, preferably comprising an organic poymer or polymer blend, for example of PEDOT:PSS (poly(3,4-ethylenedioxythiophene):poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
optionally a layer having electron transport properties, for example comprising LiF,
a low work function electrode, preferably comprising a metal like for example aluminum, serving as cathode,
wherein at least one of the electrodes, preferably the anode, is transparent to visible light, and
wherein the p-type semiconductor is a polymer according to the present invention.

A second preferred OPV device according to the invention is an inverted OPV device and comprises the following layers (in the sequence from bottom to top):
optionally a substrate,
a high work function metal or metal oxide electrode, comprising for example ITO, serving as cathode,
a layer having hole blocking properties, preferably comprising a metal oxide like $TiO_x$ or $Zn_x$,
an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic poymer or polymer blend, for example of PEDOT:PSS or TBD or NBD,
an electrode comprising a high work function metal like for example silver, serving as anode,
wherein at least one of the electrodes, preferably the cathode, is transparent to visible light, and
wherein the p-type semiconductor is a polymer according to the present invention.

In the OPV devices of the present invent invention the p-type and n-type semiconductor materials are preferably selected from the materials, like the polymer/fullerene systems, as described above When the active layer is deposited on the substrate, it forms a BHJ that phase separate at nanoscale level. For discussion on nanoscale phase separation see Dennler et al, *Proceedings of the IEEE*, 2005, 93 (8), 1429 or Hoppe et al, *Adv. Func. Mater*, 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. J. *Am. Chem. Soc.*, 2010, 132, 7595-7597.

The oligomers, polymers, formulations and layers of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises an oligomer, polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
 a source electrode,
 a drain electrode,
 a gate electrode,
 a semiconducting layer,
 one or more gate insulator layers,
 optionally a substrate.
wherein the semiconductor layer preferably comprises an oligomer, polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals*, 2000, 111-112, 31-34, Alcala, *J. Appl. Phys.*, 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science*, 1998, 279, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the oligomer and polymers of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The oligomer and polymers and formulations according to the present invention may also be suitable for use in organic plasmon-emitting diodes (OPEDs), as described for example in Koller et al., *Nat. Photonics*, 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913 A1.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci U.S.A.*, 1999, 96, 12287; D. Wang, X. Gong, P. S. Heeger, F. Rininsland, G. C. Bazan and A. J. Heeger, *Proc. Natl. Acad. Sci U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

Above and below, unless stated otherwise percentages are percent by weight and temperatures are given in degrees Celsius (° C.).

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention will now be described in more detail by reference to the following examples, which are illustrative only and do not limit the scope of the invention.

EXAMPLE 1

Diethyl 2,5-di(thieno[3,2-b]thiophen-2-yl)terephthalate

To the solution of thieno[3,2-b]thiophene (17.529 g; 125.00 mmol) in THF anhydrous (150 cm³) was added at −78° C. n-BuLi (50.0 cm³; 125.00 mmol) over 20 minutes. The mixture was stirred with cooling for 1 hour to yield a milky white suspension. The flask was lifted out of the cooling bath and was stirred without cooling for 30 min then cooled back to −78° C. again. Tributyltin chloride (35.3 cm³; 125.00 mmol) was syringed into the solution in one portion and the mixture was stirred with the cooling bath for 16 hours then at 22° C. for 1 hour to yield a white suspension.

The solid of diethyl 2,5-dibromo-terephthalate (19.00 g; 50.00 mmol), $Pd(PPh_3)_2Cl_2$ (1.0 g; 1.42 mmol; 2.84 mol %) and DMF anhydrous (50.0 cm³) were added sequentially and the mixture was heated to boiling for 0.5 hour. A distillation head was installed on the flask and 100 cm³ of the solvents were removed by distillation. The residue was then stirred at reflux for an additional 20 hours. The mixture was evaporated under vacuum to remove the low boiling solvents until a solid started crashing out. Methanol (200 cm³) was added to the residue and the precipitate was suction filtered off to yield a green-yellow crystalline solid. The solid was dissolved in hot chloroform (250 cm³) then filtered through a short silica plug (15 cm) which was washed with chloroform. The filtrate was concentrated to almost dryness and the solid was triturated with methanol followed by a suction filtration to yield the product as bright yellow crystals (19.40 g, 78%). ¹H-NMR ($CDCl_3$, 300 MHz): δ=1.13 (t, J=7.2 Hz, 3H), 4.25 (q, J=7.2 Hz, 2H), 7.28 (dd, J1=5.2 Hz, J2=0.6 Hz, 1H), 7.30 (d, J=0.6 Hz, 1H), 7.40 (d, J=5.2 Hz, 1H), 7.89 (s, 1H). $^{13}$C-NMR (CDCl$_3$, 75 MHz): δ=13.8, 61.8, 119.3, 119.4, 127.4, 132.0, 133.8, 134.1, 139.3, 139.9, 142.0, 167.4.

5,5,11,11-Tetrakis(4-octylphenyl)-dithieno[2,3-d:2', 3'-d']-s-indaceno[1,2-b:5,6-b']dithiophene To the solution of 1-bromo-4-octylbenzene (3.733 g; 12.48 mmol;) in dry THF (20.0 cm$^3$) at −78° C. was added n-BuLi (5.0 cm$^3$; 12.5 mmol). The mixture was stirred at −78° C. for 2 hours to yield a pale-yellow clear solution. The solid of diethyl 2,5-di(thieno[3,2-b]thiophen-2-yl)terephthalate (3) (1.30 g; 2.60 mmol) was added in one portion and the mixture (a yellow suspension) was stirred at −78° C. for 20 minutes. The cooling bath was removed and the mixture was stirred at 22° C. for 50 hours to yield a deep yellow clear solution. Saturated ammonium chloride solution (50 cm$^3$) was added and the mixture was stirred for 15 minutes. The orange oil was taken into diethyl ether (2×50 cm$^3$). The solvent was concentrated till a yellow solid started crashing out. Methanol (50 cm$^3$) was added to the residue and the precipitate was collected by suction filtration and washed with methanol.

The solid was dissolved in dry DCM (50 cm$^3$) and BF$_3$ etherate (1.0 cm$^3$; 8.10 mmol) was added. The blue clear solution was stirred at 22° C. for 1 hour followed by the addition of methanol (150 cm$^3$). The yellow precipitate was suction filtered off and washed with methanol. The solid was further purified by flash column chromatography on silica (9:1 petroleum ether 40-60-chloroform) to yield the producta as a bright-yellow solid (1.06 g, 36%). $^1$H-NMR (CDCl$_3$, 300 MHz): δ=0.86 (t, J=6.7 Hz, 6H), 1.25 (m, 20H), 1.58 (m, 4H), 2.54 (t, J=7.8 Hz, 4H), 7.07 (d, J=8.3 Hz, 4H), 7.18 (d, J=8.3 Hz, 4H), 7.25 (d, J=5.2 Hz, 1H), 7.27 (d, J=7.2 Hz, 1H), 7.50 (s, 1H).

3,9-Dibromo-5,5,11,11-tetrakis(4-octylphenyl)-dithieno[2,3-d:2',3'-d']-s-indaceno[1,2-b:5,6-b']dithiophene (Monomer 1)

To the clear yellow solution of 5,5,11,11-tetrakis(4-octylphenyl)-dithieno[2,3-d:2',3'-d']-s-indaceno[1,2-b:5,6-b']dithiophene (1.055 g; 0.93 mmol) in chloroform (30 cm$^3$) was added acetic acid (10 cm$^3$) followed by the addition of NBS (0.369 g; 2.05 mmol) in one portion. The mixture was stirred at 22° C. for 2 hours to yield a deep yellow suspension. Methanol (50 cm$^3$) was added and the yellow solid was suction filtered off and washed with methanol. The solid was dissolved in warm 9:1 cyclohexane-chloroform and the solution was flash columned on silica eluted with the same solvent to yield the product as a bright yellow solid (0.79 g, 66%). The solid was further purified by recrystallisation from chloroform-ethanol. $^1$H-NMR (CDCl$_3$, 300 MHz): δ=0.87 (t, J=6.7 Hz, 6H), 1.25 (m, 20H), 1.58 (m, 4H), 2.55 (t, J=7.8 Hz, 4H), 7.09 (d, J=8.4 Hz, 4H), 7.14 (d, J=8.3 Hz, 4H), 7.27 (s, 1H), 7.48 (s, 1H).

EXAMPLE 2

5,5,11,11-Tetrakis(4-dodecylphenyl)-dithieno[2,3-d: 2',3'-d']-s-indaceno[1,2-b:5,6-b']dithiophene In a similar manner to the synthesis of the 4-octylphenyl analogue, the titled compound was obtained as a pale-yellow solid in 41% yield. The compound was purified by flash chromatography on silica using warm cyclohexane as the eluent. $^1$H-NMR (CDCl$_3$, 300 MHz): δ=0.87 (t, J=6.7 Hz, 6H), 1.24 (m, 36H), 1.57 (m, 4H), 2.54 (t, J=7.8 Hz, 4H), 7.07 (d, J=8.4 Hz, 4H), 7.18 (d, J=8.3 Hz, 4H), 7.25 (d, J=5.2 Hz, 1H), 7.27 (d, J=7.2 Hz, 1H), 7.50 (s, 1H).

3,9-Dibromo-5,5,11,11-tetrakis(4-dodecylphenyl)-dithieno[2,3-d:2',3'-d']-s-indaceno[1,2-b:5,6-b']dithiophene (Monomer 2)

In analogy to the synthesis of monomer 1,5,5,11,11-tetrakis(4-dodecylphenyl)-dithieno[2,3-d:2',3'-d']-s-indaceno[1,2-b:5,6-b']dithiophene was brominated with NBS to yield monomer 2 as a bright yellow solid in 83% yield. The purification of this monomer included a flash chromatography on silica using warm cyclohexane containing 5% chloroform as eluent, followed by a recrystallisation from cyclohexane. $^1$H-NMR (CDCl$_3$, 300 MHz): δ=0.87 (t, J=6.7 Hz, 6H), 1.24 (m, 36H), 1.58 (m, 4H), 2.55 (t, J=7.8 Hz, 4H), 7.08 (d, J=8.4 Hz, 4H), 7.13 (d, J=8.3 Hz, 4H), 7.27 (s, 1H), 7.47 (s, 1H).

EXAMPLE 3

Polymer P1

A Schlenk tube was charged with 9,10-dioctyl-2,7-phenanthrylene-bis(1,3,2-dioxaborolane) (271.183 mg; 0.50 mmol), 3,9-dibromo-5,5,11,11-tetrakis(4-octylphenyl)-dithieno[2,3-d:2',3'-d']-s-indaceno[1,2-b:5,6-b']dithiophene (monomer 1) (644.792 mg; 0.50 mmol) and potassium phosphate monohydrate (0.518 g; 2.25 mmol). To this sealed tube were also added toluene (5.0 cm$^3$), 1,4-dioxane (5.0 cm$^3$) and HPLC-water (5.0 cm$^3$). The thick suspension was then degassed (stirred, bubbling N$_2$) for 1 hour. Meanwhile, a stock solution of catalyst was prepared by dissolving Pd$_2$(dba)$_3$ (14.2 mg; 0.025 mmol), tri-o-tolyl-phosphane (30.4 mg; 0.1 mmol) in anhydrous 1,4-dioxane (2.5 cm$^3$), degassed for 60 minutes.

The degassed catalyst solution (1.0 cm$^3$) was added via a plastic syringe into the first Schlenk tube. The reaction mixture was then place in an oil-bath, heated to 110° C. and stirred vigorously for 2 hours, at 120° C. for 1 hour and at 140° C. for an additional hour. The reaction mixture was cooled naturally then poured into methanol (150 cm$^3$) and the yellow solid was filtered off, washed with water and methanol. The yellow polymer solid was then purified by Soxhlet extraction with acetone, petroleum ether 40-60 and chloroform sequentially and finally dissolved in chlorobenzene. The acetone and petroleum extracts were discarded. The chloroform extract was concentrated to a smaller volume and then reprecipitated from methanol to yield the first batch of polymer P1 as a yellow solid (0.398 g) after drying under high vacuum. The molecular weights were determined by GPC (1,2,4-trichlorobenzene, 140° C.): M$_n$=48,500, g/mol, Pd: =2.69. The chlorobenzene extract, after reprecipitation from methanol, yielded the second batch of polymer P1 as a yellow solid (0.354 g). The molecular weights of this batch were determined by GPC (1,2,4-trichlorobenzene, 140° C.) as: M$_n$=135,500 g/mol, Pd=2.22. The combined yield of these two batches of solid was 98%.

Additional examples of synthesized monomers and polymers are summarized in Table 1 below.

TABLE 1

P1-P18

Structures and OFET hole mobilities of the polymer examples

| Polymer | No. | Monomer R | Co-monomer | $M_n/M_w$ (kg/mol) | $\mu$ (cm$^2$/Vs) |
|---|---|---|---|---|---|
| P1 | 1 | —C$_6$H$_4$—C$_8$H$_{17}$ | 9,10-di(C$_8$H$_{17}$)phenanthrene-2,7-diyl | 135.0/301.1$^a$ | 0.12 |
| P2 | 3 | —C$_6$H$_4$—C$_{16}$H$_{33}$ | benzothiadiazole-4,7-diyl | 68.6/116.6$^a$ | 0.45 |
| P3 | 2 | —C$_6$H$_4$—C$_{12}$H$_{25}$ | 9,10-di(C$_8$H$_{17}$)phenanthrene-2,7-diyl | 57.0/143.0$^a$ | 0.40 |
| P4 | 3 | —C$_6$H$_4$—C$_{16}$H$_{33}$ | 9,10-di(C$_8$H$_{17}$)phenanthrene-2,7-diyl | 492.0/138.0$^a$ | 0.30 |
| P5 | 3 | —C$_6$H$_4$—C$_{16}$H$_{33}$ | 2,2'-bithiophene-5,5'-diyl | 128.8/322.1$^a$ | 0.4 |
| P6 | 2 | —C$_6$H$_4$—C$_{12}$H$_{25}$ | thieno[3,2-b]thiophene-2,5-diyl | 62.8/163.9$^b$ | 0.25 |
| P7 | 2 | —C$_6$H$_4$—C$_{12}$H$_{25}$ | 2,2'-bithiophene-5,5'-diyl | 35.6/74.1$^b$ | 0.16 |
| P8 | 3 | —C$_6$H$_4$—C$_{16}$H$_{33}$ | thieno[3,2-b]thiophene-2,5-diyl | 71.6/187.6$^b$ | 0.75 |
| P9 | 4 | —C$_6$H$_4$—C$_{12}$H$_{25}$ | 2 | 30.7/68.8$^b$ | 0.10 |

TABLE 1-continued

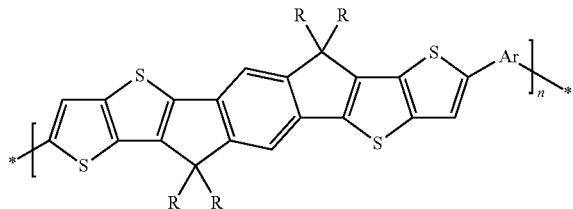

Structures and OFET hole mobilities of the polymer examples

| Polymer | No. | Monomer R | Co-monomer | $M_n/M_w$ (kg/mol) | $\mu$ (cm$^2$/Vs) |
|---|---|---|---|---|---|
| P10 | 4 | —C$_6$H$_4$—C$_{12}$H$_{25}$ | EH-DPP-bis(5-methylthiophene) | 22.5/44.8[b] | 0.05 |
| P11 | 2 | —C$_6$H$_4$—C$_{12}$H$_{25}$ | 9,10-di(C$_{12}$H$_{25}$)phenanthrene | 76.5/371.6[b] | 0.04 |
| P12 | 5 | 5-C$_{16}$H$_{33}$-thiophen-2-yl | 9,10-di(C$_8$H$_{17}$)phenanthrene | 69.9/264.7[a] | 0.03 |
| P13 | 6 | —C$_6$H$_4$—OC$_8$H$_{17}$ | 9,10-di(C$_8$H$_{17}$)phenanthrene | 70.8/200.7[a] | 0.03 |
| P14 | 2 | —C$_6$H$_4$—C$_{12}$H$_{25}$ | benzothiadiazole | 20.8/95.2[a] | 0.005 |
| P15 | 1 | —C$_6$H$_4$—C$_8$H$_{17}$ | 4,8-di(C$_{12}$H$_{25}$)benzodithiophene | 13.2/27.3[a] | 0.0014 |

TABLE 1-continued

P1-P18

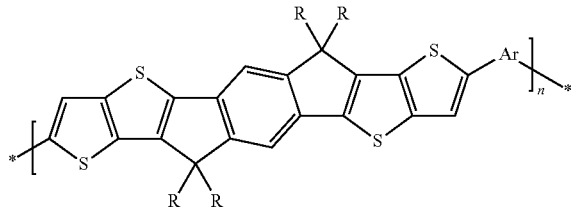

Structures and OFET hole mobilities of the polymer examples

| Polymer | No. | Monomer R | Co-monomer | $M_n/M_w$ (kg/mol) | μ (cm$^2$/Vs) |
|---|---|---|---|---|---|
| P16 | 7 | —⟨phenyl⟩—OC$_{12}$H$_{25}$ | C$_8$H$_{17}$, C$_8$H$_{17}$ phenanthrylene | 24.3/94.4[b] | 0.009 |

GPC measurements were run using polystyrene as standard and
[a]1,2,4-trichlorobenzene (140° C.);
[b]Chlorobenzene (50° C.) as the solvents.

EXAMPLE 4

3,9-Dibromo-5,5,11,11-tetrakis(4-hexadecylphenyl)-dithieno[2,3-d:2',3'-d']-s-indaceno[1,2-b:5,6-b']dithiophene (Monomer 3)

In analogy to the synthesis of monomers 1 and 2,1-bromohexadecylbenzene (11.59 g, 30 mmol) was lithiated with n-BuLi (12 cm$^3$, 30 mmol) in dry THF (300 cm$^3$) at −35° C. The lithiated intermediate reacted with diethyl 2,5-di(thieno[3,2-b]thiophen-2-yl)terephthalate (3.00 g; 6.02 mmol). The resultant crude diol intermediate was ring-closed with p-toluenesulfonic acid monohydrate (2.0 g, 10.51 mmol) in dichloromethane (150 cm$^3$) to yield the crude ring-closed product as a deep yellow solid. The solid was purified by flash column chromatography on silica eluted with cyclohexane to afford the product 5,5,11,11-tetrakis(4-hexadecylphenyl)-dithieno[2,3-d:2',3'-d']-s-indaceno[1,2-b:5,6-b']dithiophene as a canary yellow solid (6.28 g, 65%). $^1$H NMR (300 MHz, CDCl$_3$) δ=ppm 0.83-0.93 (m, 6 H), 1.19-1.39 (m, 52 H), 1.52-1.66 (m, 4 H), 2.50-2.59 (m, 4 H), 7.05 (d, J=8.2 Hz, 4 H), 7.17 (d, J=8.3 Hz, 4 H), 7.21-7.26 (m, 2 H), 7.48 (s, 1 H).

The solid (5.39 g, 3.37 mmol) was brominated with NBS (1.33 g, 7.24 mmol) in a solvent mixture of chloroform (300 cm$^3$) and acetic acid (60 cm$^3$) by stirring at 35° C. for 1 hour. The crude product was purified by column chromatography on silica eluted with cyclohexane, followed by a recrystallisation from cyclohexane petroleum ether (80-100° C.) to yield 3,9-dibromo-5,5,11,11-tetrakis(4-hexadecylphenyl)-dithieno[2,3-d:2',3'-d']-s-indaceno[1,2-b:5,6-b']dithiophene (monomer 3) as a bright yellow solid (5.58 g, 95%). $^1$H NMR (300 MHz, chloroform-d) δ ppm 0.86-0.94 (m, 6H), 1.23-1.34 (m, 52 H), 1.54-1.67 (m, 4 H), 2.7 (t, J=7.9 Hz, 4 H), 7.06-7.16 (m, 8H), 7.26 (s, 1H), 7.47 (s, 1 H).

EXAMPLE 5

Polymer P2

A Schlenk tube was charged with monomer 3 (434.6 mg; 0.25 mmol), 4,7-bis-(4,4,5,5-tetramethyl-[1,3,2]dioxaborolan-2-yl)-benzo[1,2,5]thiadiazole (97.0 mg; 0.25 mmol), Pd$_2$(dba)$_3$ (2.8 mg, 1.24 mol %), tri-o-tolyl phosphine (6.1 mg, 8.00 mol %), Aliquat 336 (0.010 g), toluene (5 cm$^3$) and sodium carbonate (2 M in water) (1.0 cm$^3$; 2.00 mmol). The mixture was degassed by bubbling N$_2$ through for 60 minutes at 22° C. The reaction mixture was placed in an preheated oil-bath and stirred at 120° C. for 20 hours to yield a navy blue mixture. The mixture was cooled naturally for 10 minutes and bromobenzene (0.050 cm$^3$; 0.47 mmol) was added. The mixture was stirred with heating for 50 minutes and was cooled for 10 minutes again. 4-Ethylphenylboronic acid (0.100 g; 0.67 mmol) solution (in 0.5 cm$^3$ dioxane) was added and the vial was lowered into the oil-bath and stirred for an additional 50 minutes.

The mixture was cooled to 22° C. and precipitated into stirred methanol (200 cm$^3$). The dark-blue fibrous precipitate was collected by suction filtration and washed with methanol, water then acetone. The crude polymer was subject to Sohxlet extraction with acetone, petroleum ether (40-60° C.), cyclohexane then dissolved with chloroform. The chlororform extract was concentrated to a smaller volume and precipitated from methanol to yield a dark blue solid of polymer P2 in yield of 0.232 g (54%) after drying in a vacuum oven. The molecular weights were determined with GPC (1,2,4-trichlorobenzene, 140° C.) as: $M_n$=68,400 g/mol, Pd=1.70.

EXAMPLE 6

Polymer P3

In analogy to the synthesis of polymer P1, monomer 2 (2.2710 g, 1.50 mmol) and 9,10-dioctyl-2,7-phenanthrylene-bis(1,3,2-dioxaborolane) (0.8135 g, 1.50 mmol) were polymerised in a solvent mixture of toluene (15 cm$^3$) and 1,4-dioxane (15 cm$^3$) containing HPLC water (15 cm$^3$), potassium phosphate monohydrate (1.554 g, 6.75 mmol), Pd$_2$(dba)$_3$ (17.0 mg, 0.02 mmol) and tri-o-tolylphosphine (36.5 mg, 0.12 mmol). At the end of the polymerisation, the polymer was end-capped by reacting with bromobenzene (0.10 cm$^3$) and phenylboronic acid (0.14 g) sequentially for 1 hour each at 110° C. The deep-yellow polymer solid precipitated from methanol was purified by sequential Sohxlet extraction with acetone, petroleum ether (40-60° C.), cyclohexane and finally dissolved in chlorobenzene and precipitated from methanol. The yield of polymer P3 was 2.38 g (90%). The molecular weights were determined with GPC (1,2,4-trichlorobenzene, 140° C.) as: $M_n$=57,000 g/mol, Pd=2.51.

EXAMPLE 7

Polymer P4

In analogy to the synthesis of polymer P3, monomer 3 (0.6954 g, 0.40 mmol) and 9,10-dioctyl-2,7-phenanthrylene-bis(1,3,2-dioxaborolane) (0.2169 g, 0.40 mmol) were co-polymerised in a solvent mixture of toluene (5 cm$^3$) and 1,4-dioxane (5 cm$^3$) containing water (5 cm$^3$), potassium phosphate monohydrate (0.415 g, 1.8 mmol), Pd$_2$(dba)$_3$ (4.5 mg, 1.20 mol %) and tri-o-tolylphosphine (9.7 mg, 8.0 mol %). The polymer was end-capped by reacting with bromobenzene (0.05 cm$^3$) and phenylboronic acid (0.10 g) sequentially for 1 hour each at 110° C. The deep yellow polymer solid precipitated from methanol was purified by sequential Sohxlet extraction with acetone, petroleum ether (40-60° C.) and finally dissolved in chloroform then precipitated from methanol. The yield of polymer P4 was 0.76 g (96%). The molecular weights were determined with GPC (1,2,4-trichlorobenzene, 140° C.) as: $M_n$=49,200 g/mol, Pd=2.96.

EXAMPLE 8

Polymer P5

A Schlenk tube was charged with monomer 3 (434.6 mg; 0.25 mmol), 4,4'-bis(trimethylstannyl)-2,2'-bithiophene (123.0 mg; 0.25 mmol), Pd$_2$(dba)$_3$ (2.8 mg; 1.59 mol %), tri-o-tolylphosphine (6.1 mg; 8.02 mol %), toluene, anhydrous (4.0 cm$^3$) and DMF (1.0 cm$^3$). The mixture was degassed by bubbling N$_2$ for 1 hour then stirred at 110° C. for 0.5 hour to yield a red viscous solution. The vial was cooled naturally for 5 min and bromobenzene (0.05 cm$^3$; 0.47 mmol) was added. The mixture was stirred at 110° C. for an additional 30 minutes followed by the addition of phenyl tributyltin (0.20 cm$^3$; 0.61 mmol). The mixture was stirred for an additional 50 minutes at 110° C.

The viscous solution was diluted with 5 ml of toluene while it was hot then cooled to rt and precipitated into stirred methanol (200 ml). The rosy-red plastic solid was collected by suction filtration and washed with methanol and acetone. The polymer solid was purified by sequential Sohxlet extraction with acetone, petroleum ether (40-60° C.) and finally dissolved in chloroform and precipitated from methanol. The yield of polymer P5 was 0.375 g (86%). The molecular weights were $M_n$=134,100 g/mol, Pd=2.59 as determined by GPC (1,2,4-trichlorobenzene, 140° C.).

EXAMPLE 9

Polymer P6

In analogy to the synthesis of polymer P5, monomer 2 (0.7570 g, 0.50 mmol) was co-polymerised with 2,5-bis(trimethylstannyl)thieno[3,2-b]thiophene (0.2329 g, 0.50 mmol) in dry toluene (9.0 cm$^3$) and DMF (1.0 cm$^3$) in the presence of Pd(PPh)$_3$Cl$_2$ (11.5 mg; 0.02 mmol). The reaction mixture was degassed and stirred at 100° C. for 15 minutes, then end-capped with 2-iodothiophene. The polymer solid precipitated from methanol was then purified with Soxhlet extraction with acetone, petroleum ether (40-60° C.), cyclohexane and finally dissolved in chloroform and reprecipated to yield polymer P6 as a deep red fibrous. The yield was 0.71 g (95%) and the molecular weights were $M_n$=62,800 g/mol, Pd=2.61 as determined by GPC (chlorobenzene, 50° C.).

EXAMPLE 10

Polymer P7

In analogy to the synthesis of polymer P6, monomer 2 (0.7570 g, 0.50 mmol) was co-polymerised with 4,4'-bis(trimethylstannyl)-2,2'-bithiophene (0.2459 g, 0.50 mmol) in dry toluene (10.0 cm$^3$) in the presence of Pd(PPh)$_3$Cl$_2$ (11.5 mg; 0.02 mmol). The reaction mixture was degassed and stirred at 100° C. for 2 hours, then end-capped with 2-iodothiophene. The crude polymer solid was precipitated from methanol then purified with Soxhlet extraction with acetone, petroleum ether (40-60° C.) and finally dissolved with chloroform and re-precipitated from methanol to yield polymer P7 as a red fibrous solid. The yield was 0.67 g (88%) and the molecular weights were $M_n$=35,600 g/mol, Pd=2.08 as determined by GPC (chlorobenzene, 50° C.).

EXAMPLE 11

Polymer P8

In analogy to the synthesis of polymer P5, monomer 3 (0.8409 g, 0.48 mmol) and 2,5-bistrimethylstannylthieno[3,2-b]thiophene (0.2253 g, 0.48 mmol) were co-polymerised in dry toluene (9.5 cm$^3$) and DMF (2.0 cm$^3$) in the presence of Pd$_2$(dba)$_3$ (5.4 mg; 1.59 mol %), tri-o-tolylphosphine (11.7 mg, 7.95 mol %). The polymer was end-capped with bromobenzene (0.05 cm$^3$, 0.47 mmol) and phenyl tributyltin (0.20 cm$^3$, 0.61 mmol) sequentially before precipitated from methanol. Sohxlet extraction with acetone, petroleum ether (40-60° C.), cyclohexane, acetone was carried out to removed impurities and finally dissolved in chloroform then re-precipitated from methanol and dried. The yield of polymer P8 was 0.80 g (96%) and the molecular weights were $M_n$=71,600 g/mol, Pd=2.62 as determined by GPC (chlorobenzene, 50° C.).

EXAMPLE 12

3,9-Bis(trimethylstannyl)-5,5,11,11-tetrakis(4-dodecylphenyl)-dithieno[2,3-d:2',3'-d']-s-indaceno[1,2-b:5,6-b']dithiophene (Monomer 4)

To the solution of monomer 2 (2.50 g, 1.65 mmol) in dry THF (50 cm$^3$) (dissolved by heating with a warm water-bath then cooled down slowly to −50° C. with acetone and dry-ice) was added n-BuLi (1.90 cm$^3$, 4.75 mmol) over 10 minutes, to yield a deep yellow clear solution. The temperature was lowered to −78° C. and the solution was stirred for 2 hours to yield a yellow suspension. Chlorotrimethylstannane (5.0 cm$^3$, 5.0 mmol) was added through a syringe in one portion and the resultant clear orange solution was stirred at −78° C. for 2 hours prior to the removal of the cooling bath then stirred at 22° C. for 16 hours. The dark orange solution was vacuum evaporated to dryness to yield a pale-brown gum. The crude product was dissolved in petroleum ether (40-60° C.), suction filtered through a fiber glass filter. The filtrate was evaporated to dryness under maximum vacuum to yield a pale-brown sticky solid (2.79 g). The crude titled compound (monomer 4) was used directly for subsequent polymerisations without further purification.

EXAMPLE 13

Polymer P9

The above prepared 3,9-bis(trimethylstannyl)-5,5,11,11-tetrakis(4-dodecylphenyl)-dithieno[2,3-d:2',3'-d']-s-indaceno[1,2-b:5,6-b']dithiophene (monomer 4)(0.4502 g; 0.27 mmol), monomer 2 (0.4053 g; 0.27 mmol), Pd(PPh$_3$)$_2$Cl$_2$ (6.5 mg; 3.45 mol %), dry toluene (5.0 cm$^3$) and dry DMF (1.0 cm$^3$) were charged in a Schlenk tube. The mixture was degassed then stirred at 110° C. for 4 hours to yield a red viscous solution. The polymer was end-capped with bromobenzene and phenyl tributyltin followed by a precipitation from stirred methanol (300 cm$^3$). The red solid was collected by suction filtration and washed with methanol and acetone then purified with Sohxlet extracted with acetone and petroleum ether (40-60° C.) and finally dissolved with chloroform. The chloroform solution was concentrated to a smaller volume and re-precipitated into methanol to yield polymer P9 as a red solid (0.677 g, 92%). The molecular weights were $M_n$=30,700 g/mol, Pd=2.24 as determined by GPC (chlorobenzene, 50° C.).

EXAMPLE 14

Polymer P10

In analogy to the synthesis of polymer P9, the above prepared 3,9-bis(trimethylstannyl)-5,5,11,11-tetrakis(4-dodecylphenyl)-dithieno[2,3-d:2',3'-d']-s-indaceno[1,2-b:5,6-b']dithiophene (monomer 4)(0.4730 g, 0.28 mmol), 3,6-bis(5-bromo-thiophen-2-yl)-N,N'-bis(2-ethyl-1-hexyl)-1,4-dioxopyrrolo[3,4-c]pyrrole (0.1920 g, 0.28 mmol) Pd(PPh$_3$)$_2$Cl$_2$ (6.5 mg; 0.01 mmol; 3.45 mol %), dry toluene, (5.0 cm$^3$) and dry DMF (1.0 cm$^3$) were charged in a Schlenk tube. The mixture was degassed then stirred at 110° C. for 2 hours to yield a dark-green viscous solution. The polymer was end-capped with bromobenzene and phenyl tributyltin followed by a precipitation into stirred methanol. The resultant purple-blue solid was collected by suction filtration and washed with methanol and acetone. The solid was Sohxlet extracted with acetone and petroleum ether (40-60° C.) and finally dissolved in chloroform re-precipitated into methanol to yield polymer P10 as a brown-green solid (0.459 g, 87%). The molecular weights were $M_n$=22,500 g/mol, Pd=2.00 as determined by GPC (chlorobenzene, 50° C.).

EXAMPLE 15

Polymer P11

In analogy to the synthesis of polymer P4, monomer 2 (0.3949 g, 0.261 mmol) and 9,10-didodecyl-2,7-phenanthrylene-bis(1,3,2-dioxaborolane) (0.2000 g, 0.261 mmol) were co-polymerised in toluene (2.6 cm$^3$) in the presence of Pd$_2$(dba)$_3$ (7.2 mg, 3.0 mol %), Aliquat 336 (ca 10 mg) and 2.0M sodium carbonate (1.0 cm$^3$, 2.0 mmol). The reaction mixture was stirred at 120° C. for 2 hours, then end-capped by reacting bromobenzene (0.03 cm$^3$) and phenylboronic acid (0.07 g) sequentially for 40 minutes each at 120° C. The deep yellow polymer solid precipitated from methanol was purified by sequential Sohxlet extraction with acetone, petroleum ether (40-60° C.), cyclohexane and finally dissolved in chloroform and reprecipitated from methanol. The yield of polymer P11 was 0.33 g (68%). The molecular weights were $M_n$=76,500 g/mol, Pd=4.9 as determined by GPC (chlorobenzene, 50° C.).

EXAMPLE 16

3,9-Dibromo-5,5,11,11-tetrakis(5-hexadecylthien-2-yl)-dithieno[2,3-d:2',3'-d']-s-indaceno[1,2-b:5,6-b']dithiophene (Monomer 5)

To the solution of 2-hexadecylthiophene (4.011 g; 13.00 mmol) in dry THF (30 cm$^3$) at −5° C. was added n-BuLi (5.2 cm$^3$; 13.00 mmol) over 10 minutes. The mixture was stirred at −5° C. for 1 hour to yield a clear colourless solution. The solid of diethyl 2,5-di(thieno[3,2-b]thiophen-2-yl)terephthalate (3) (1.297 g, 2.60 mmol) was added in one portion and the mixture (a brown suspension) was stirred at −5° C. for 10 minutes. The cooling bath was removed and the mixture was stirred at 22° C. for 20 hours to yield a pale-red clear solution. The solution was then stirred at 60° C. for an additional 1 hour. Ice-water (50 ml) was added and the mixture was vigorously stirred for 10 minutes followed by the addition of methanol (50 cm$^3$). The yellow precipitated was collected by suction filtration and washed with methanol then air-dried on the filter to yield a sandy yellow solid.

To the solution of the above prepared solid in dry DCM (50 cm$^3$) was added BF$_3$ etherate (1.0 cm$^3$; 8.10 mmol). The purple red solution was stirred at 22° C. for 2 hours. Methanol (ca 50 cm$^3$) was added and the mixture was stirred for 20 minutes. The upper clear solution was decanted and the residue red thick oil was purified by flash column on silica (9:1 cyclohexane-chloroform as the eluent) to yield 5,5,11,11-tetrakis(5-hexadecyl-2-thienyl)-dithieno[2,3-d:2',3'-d']-s-indaceno[1,2-b:5,6-b']dithiophene as a yellow solid (0.598 g, 14%). $^1$H NMR (300 MHz, CDCl$_3$) δ=7.68 (s, 1H), 7.34 (d, J=5.2 Hz, 1H), 7.30 (d, J=5.2 Hz, 1H), 6.79 (d, J=3.6 Hz, 2H), 6.55 (d, J=3.5 Hz, 2H), 2.70 (t, J=7.7 Hz, 4H), 1.61 (m, 4H), 1.34-1.17 (m, 52H), 0.88 (t, J=6.7 Hz, 6H).

The above prepared solid (0.590 g, 0.37 mmol) in chloroform (30 cm$^3$) and acetic acid (10 cm$^3$) was added NBS (0.145 g; 0.81 mmol) in one portion. The mixture was stirred at 22° C. for 2 hours to yield a pale-brown suspension. Methanol (100 cm$^3$) was added and the dark yellow solid was suction filtered off and washed with methanol. The solid was dissolved in hot cyclohexane and the solution was flash columned on silica eluted with 95:5 cyclohexane-chloroform to yield monomer 5 as bright yellow solid (0.41 g, 63%). $^1$H NMR (300 MHz, CDCl$_3$) δ=7.65 (s, 1H), 7.29 (s, 1H), 6.75 (d, J=3.5 Hz, 2H), 6.55 (d, J=3.5 Hz, 2H), 2.70 (t, J=7.7 Hz, 4H), 1.66-1.56 (m, 4H), 1.24 (m, 52H), 0.88 (t, J=6.7 Hz, 6H).

EXAMPLE 17

Polymer P12

In analogy to the synthesis of polymer P3, monomer 5 (0.3525 g, 0.20 mmol) and 9,10-dioctyl-2,7-phenanthrylene-bis(1,3,2-dioxaborolane) (0.1085 g, 0.20 mmol) were co-polymerised in a solvent mixture of toluene (2.0 cm$^3$) and 1,4-dioxane (2.0 cm$^3$) containing water (2.0 cm$^3$), potassium phosphate monohydrate (0.207 g, 0.90 mmol), Pd$_2$(dba)$_3$ (2.3 mg, 1.20 mol %) and tri-o-tolylphosphine (4.9 mg, 8.0 mol %). The polymer was end-capped by reacting with 2-iodothiophene (0.10 cm$^3$) and thiopheneboronic acid (0.14 g) sequentially for 30 minutes each at 120° C.

The yellow polymer solution was precipitated from methanol was the solid was purified by sequential Sohxlet extraction with acetone and petroleum ether (40-60° C.), and finally dissolved in chloroform and reprecipitated in methanol to yield polymer P12 as an orange solid 0.38 g (95%). The molecular weights $M_n$=69,900 g/mol, Pd=3.78 were as determined GPC (1,2,4-trichlorobenzene, 140° C.).

EXAMPLE 18

3,9-Dibromo-5,5,11,11-tetrakis(4-octyloxyphenyl)-dithieno[2,3-d:2',3'-d']-s-indaceno[1,2-b:5,6-b']dithiophene (Monomer 6)

To the solution of 1-bromo-4-octyloxybenzene (11.529 g; 38.4 mmol) in dry THF (100 cm$^3$) at −78° C. was added n-BuLi 2.5M (15.4 cm$^3$; 38.4 mmol) over 30 minutes. The mixture was stirred at −78° C. for 2 hours. The solid of diethyl 2,5-di(thieno[3,2-b]thiophen-2-yl)terephthalate (3.989 g, 8.00 mmol) was added in one portion. The cooling bath was removed and the mixture was stirred at 22° C. for 17 hours to yield a dark-yellow solution. Ice-water (250 cm$^3$) was added and the mixture was vigorously stirred for 10 minutes. The reaction mixture was extracted with diethyl ether (4×70 cm$^3$). The combined ether solution was washed with brine once, dried over MgSO$_4$ then evaporated to dryness to yield a yellow oil. The oil was triturated with methanol (100 cm$^3$) and the precipitate was collected by suction filtration. The solid was dissolved in dry DCM (100 cm$^3$) followed by the addition of BF$_3$ etherate (3.1 cm$^3$; 25.2 mmol). The solution was stirred at 22° C. for 1 hour. Methanol (ca. 10 cm$^3$) was added and the mixture was concentrated to dryness. The residual red thick oil was purified by flash column on silica eluted with 8:2 petroleum ether-diethyl ether to yield 5,5,11,11-tetrakis(4-octyloxyphenyl)-dithieno[2,3-d:2',3'-d']-s-indaceno[1,2-b:5,6-b']dithiophene as a white solid (1.20 g, 12.5%).

The above prepared solid (1.20 g, 0.998 mmol) was dissolved in chloroform (50 cm$^3$) and acetic acid (12.5 cm$^3$), and NBS (0.395 g; 2.20 mmol) as added in one portion. The mixture was stirred at 22° C. for 16 hours. The solvents were removed by vacuum evaporation. The residue was triturated with methanol (100 cm$^3$). The precipitated was collected by suction filtration and dried on the filter then subjected to a flash columned purification on silica eluted with 9:1 cyclohexane-dichloromethane to yield monomer 6 as a pale-brown solid (0.80 g, 59%). $^1$H NMR (300M, CDCl$_3$) δ=7.43 (s, 1H), 7.27 (s, 1H), 7.17-7.10 (m, 4H), 6.83-6.76 (m, 4H), 3.89 (t, J=6.5 Hz, 4H), 1.72 (m, 4H), 1.41 (m, 4H), 1.35-1.20 (m, 16H), 0.87 (m, 6H).

EXAMPLE 19

Polymer P13

In analogy to the synthesis of polymer P3, monomer 6 (0.3993 g, 0.295 mmol) and 9,10-dioctyl-2,7-phenanthrylene-bis(1,3,2-dioxaborolane) (0.160 g, 0.295 mmol) were polymerised in a solvent mixture of toluene (3.0 cm$^3$) and 1,4-dioxane (3.0 cm$^3$) containing water (3.0 cm$^3$), potassium phosphate monohydrate (0.306 g, 0.1.328 mmol), Pd$_2$(dba)$_3$ (3.3 mg, 1.20 mol %) and tri-o-tolylphosphine (7.2 mg, 8.0 mol %). The crude yellow polymer solid precipitated from methanol was purified by sequential Sohxlet extraction with methanol, acetone, petroleum ether (40-60° C.), petroleum ether (80-100° C.), cyclohexane and finally dissolved off with chloroform to yield polymer P13 as a yellow solid 0.30 g (64%). The molecular weights were determined with GPC (1,2,4-trichlorobenzene, 140° C.) as: $M_n$=70,800 g/mol, and Pd=2.83.

EXAMPLE 20

Polymer P14

In analogy to the synthesis of polymer P2, monomer 2 (757.0 mg; 0.50 mmol) and 4,7-bis-(4,4,5,5-tetramethyl-[1,3,2]dioxaborolan-2-yl)-benzo[1,2,5]thiadiazole (194.0 mg; 0.50 mmol) were co-polymerised toluene (15 cm$^3$) in the presence of Pd$_2$(dba)$_3$ (5.7 mg, 1.24 mol %), tri-o-tolyl phosphine (12.2 mg, 8.00 mol %), Aliquat 336 (0.010 g), and sodium carbonate (2 M in water) (1.0 cm$^3$; 2.00 mmol). The crude polymer was purified by Soxhlet extraction with acetone and cyclohexane then dissolved in chloroform and reprecipitated from methanol, to afford polymer P14 as a dark purple solid (0.67 g, 90%). %). The molecular weights were $M_n$=23,600 g/mol; Pd=4.21 as determined by GPC (1,2,4-trichlorobenzene, 140° C.).

EXAMPLE 21

Polymer P15

In analogy to the synthesis of Polymer P2, monomer 1 (644.8 mg, 0.50 mmol) and 7,8-didodecyl-2,5-bis(4,4,5,5-tetramethyl-[1,3,2]dioxaborolan-2-yl)benzo[1,2-b;4,5-b']dithiophene (389.4 mg, 0.50 mmol) were co-polymerized in toluene (12 cm$^3$) in the presence of Pd$_2$(dba)$_3$ (13.7 mg, 3.0 mol %), tri-o-tolyl phosphine (36.5 mg, 24 mol %), Aliquat 336 (0.010 g), and sodium carbonate (2 M in water) (2.0 cm$^3$; 4.00 mmol). The crude polymer was purified by Soxhlet extraction with acetone and petroleum ether (40-60° C.) then dissolved in chloroform and reprecipitated from methanol, to afford polymer P15 as a red solid (0.66 g, 80%). The molecular weights were $M_n$=13,200 g/mol; Pd=2.08 as determined by GPC (1,2,4-trichlorobenzene, 140° C.).

EXAMPLE 22

3,9-Dibromo-5,5,11,11-tetrakis(4-dodecyloxyphenyl)-dithieno[2,3-d:2',3'-d']-s-indaceno[1,2-b:5,6-b']dithiophene (Monomer 7)

In analogy to the synthesis of monomer 6, the solution of 1-bromo-4-dodecyloxybenzene (16.38 g; 48 mmol) in dry THF (100 cm$^3$) at −78° C. was treated with n-BuLi 2.5M (19.2 cm$^3$; 48.0 mmol) then reacted with diethyl 2,5-di(thieno[3,2-b]thiophen-2-yl)terephthalate (4.99 g, 10.0 mmol), to afford the diol. The crude diol intermediate was dissolved in dry DCM (100 cm$^3$) followed by the addition of BF$_3$ etherate (3.1 cm$^3$; 25.2 mmol) to closed the ring to afford 5,5,11,11-tetrakis(4-dodecyloxyphenyl)-dithieno[2,3-d:2',3'-d']-s-indaceno[1,2-b:5,6-b']dithiophene as a yellow solid (2.50 g, 17.6%) after column chromatography purification. $^1$H NMR (300 MHz, CD$_2$Cl$_2$) δ=7.48 (s, 1H), 7.30 (s, 2H), 7.16 (d, J=8.8, 4H), 6.78 (d, J=8.8, 4H), 3.88 (t, J=6.5 Hz, 4H), 1.76-1.65 (m, 4H), 1.40 (br. s., 4H), 1.24 (s, 32H), 0.86 (t, J=6.9 Hz, 6H).

The above prepared solid (1.50 g, 1.06 mmol) was brominated with NBS (0.418 g; 2.32 mmol) in THF (50 cm$^3$). The crude dibromide was flash column chromatographed on silica eluted with 4:1 petroleum ether (40-60° C.)-dichloromethane to yield monomer 7 as a pale-brown solid (1.50 g, 90%). $^1$H NMR (300 MHz, CD$_2$Cl$_2$) δ=7.47 (s, 1H), 7.31 (s, 1H), 7.12 (d, J=8.8 Hz, 4H), 6.78 (d, J=8.8 Hz, 4H), 3.88 (t, J=6.5 Hz, 4H), 1.77-1.66 (m, 4H), 1.40 (br. s., 4H), 1.25 (s, 32H), 0.86 (t, J=6.6 Hz, 6H).

EXAMPLE 23

Polymer P16

In analogy to the synthesis of polymer P13, monomer 7 (0.0.4655 g, 0.295 mmol) and 9,10-dioctyl-2,7-phenanthrylene-bis(1,3,2-dioxaborolane) (0.1600 g, 0.295 mmol) were co-polymerised in a solvent mixture of toluene (3.0 cm$^3$) and 1,4-dioxane (3.0 cm$^3$) containing water (3.0 cm$^3$), potassium phosphate monohydrate (0.306 g, 0.1.328 mmol), Pd$_2$(dba)$_3$ (3.3 mg, 1.20 mol %) and tri-o-tolylphosphine (7.2 mg, 8.0 mol %). The reaction took 3 hours to finish and the polymer mixture was diluted with chlorobenzene (50 cm$^3$) then precipitated from methanol. The brown solid polymer was purified by sequential Sohxlet extraction with methanol, acetone, petroleum ether (40-60° C.), petroleum ether (80-100° C.), cyclohexane and finally dissolved off with chloroform and reprecipitated from methanol to yield polymer P16 as a yellow solid 0.35 g (65%). The molecular weights were M$_n$=24,300 g/mol, and Pd=3.89 as determined by GPC (chlorobenzene, 50° C.).

EXAMPLE 24

Transistor Fabrication and Measurements: a General Procedure

Top-gate thin-film organic field-effect transistors (OFETs) were fabricated on XG glass substrates with thermally evaporated Au source-drain electrodes. The glass substrate was treated with Decon 90 for 30 minutes, rinsed with de-ionised water four times, supersonicated in de-ionised water and methanol sequentially for 1 minute each and finally spin-dried in air. The Au electrodes were deposited under 5×10$^{-6}$ mBar vacuum at a rate of 0.1-0.2 nm/s. A polymer solution in o-dichlorobenenzene at the concentration of 7 mg/cm$^3$ was spin-coated on top followed by a spin-coated fluoropolymer dielectric material (D139). Finally the Au gate electrode was deposited by thermal evaporation. The electrical characterization of the transistor devices was carried out in ambient air atmosphere using a computer controlled Agilent 4155C Semiconductor Parameter Analyser. Charge carrier mobilities for polymers P1-P18 in the saturation regime ($\mu_{sat}$) were calculated and are shown in Table 1. Field-effect mobilities were calculated in the saturation regime ($V_d$>($V_g$-$V_0$)) using equation (1):

$$\left(\frac{dI_d^{sat}}{dV_g}\right)_{V_d} = \frac{WC_i}{L}\mu^{sat}(V_g - V_0) \tag{1}$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

EXAMPLE 25

Bulk heterojunction Organic Photovoltaic Devices (OPVs) for Polymer P14

OPV devices are fabricated on ITO-glass substrates (13Ω/), purchased from Zencatec. Substrates are subjected to a conventional photolithography process to define the bottom electrodes (anodes) before cleaning using common solvents (acetone, IPA, DI water) in an ultrasonic bath. A conducting polymer poly(ethylene dioxythiophene) doped with poly(styrene sulfonic acid) [Clevios VPAI 4083 (H.C. Starck)] is mixed in a 1:1 ratio with DI-water. This solution is sonicated for 20 minutes to ensure proper mixing and filtered using a 0.2 µm filter before spin coating to a thickness of 20 nm. Substrates are exposed to a UV-ozone treatment prior to the spin-coating process to ensure good wetting properties. Films are then annealed at 130° C. for 30 minutes in an inert atmosphere.

Photoactive material solutions are prepared at the concentration of 30 mg/cm$^3$ and at components ratio of 1:3 (polymer P14:PC$_{61}$BM), and stirred overnight. Thin films are blade coated in an inert atmosphere to achieve thicknesses around 200 nm, measured using a profilemeter. A short drying period follows to ensure removal of excess solvent. Typically, blade coated films are dried at 70° C. for 2 minutes on the hotplate. As the last step of the device fabrication, Calcium (30 nm)/Al (200 nm) cathodes are thermally evaporated through a shadow mask to define cells. Samples are measured at 23° C. using a Solar Simulator from Newport Ltd (model 91160) as a light source, calibrated to 1 sun using a Si reference cell.

The average device performance data for blends of polymer P14:PC$_{61}$BM is as follows: open circuit potential ($V_{oc}$)= 890 mV, current density ($J_{SC}$)=5.14 mA/cm$^2$, fill factor (FF)=52.7%, power conversion efficiency (PCE)=2.41%.

The invention claimed is:

1. An oligomer or polymer comprising divalent units of formula I

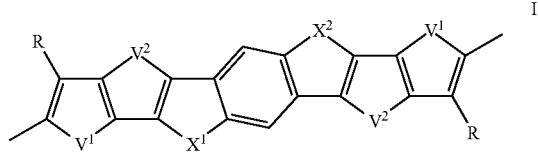

wherein
$V^1$ and $V^2$ are independently of each other O, S, Se or Te,
$X^1$ and $X^2$ are independently of each other $CR^1R^2$, $C=CR^1R^2$, $SiR^1R^2$ or $GeR^1R^2$,
R, $R^1$ and $R^2$ independently of each other, and on each occurrence identically or differently, denote H, F, Cl, Br, CN, straight-chain, branched or cyclic alkyl, with 1 to 30 C atoms, in which one or more non-adjacent C atoms are optionally replaced by —O—, —S—, —C(O)—, —C(O)—O—, —O—C(O)—, —O—C(O)—O—, —C(S)—, —C(S)—O—, —O—C(S)—, —O—C(S)—O—, —C(O)—S—, —S—C(O)—, —O—C(O)—S—, —S—C(O)—O—, —S—C(O)—S—, —S—C(S)—S—, —O—C(S)—S—, —S—C(S)—O—, —C(S)—S—, —S—C(S)—, —NR$^0$—, —SiR$^0$R$^{00}$—, —CY$^1$=CY$^2$— or —C≡C— in such a manner that O and/or S atoms are not linked directly to one another, and in which one or more H atoms are optionally replaced by F, Cl, Br, I or CN, or $R^1$ and $R^2$, independently of each other, and on each occurrence identically or differently, denote aryl, heteroaryl, aryloxy or heteroaryloxy with 4 to 20 ring atoms which is optionally substituted, or $R^1$ and $R^2$ together form an alicyclic group with 1 to 20 C atoms, which is optionally fluorinated or alkylated,
$Y^1$ and $Y^2$ are independently of each other H, F, Cl or CN,
$R^0$ and $R^{00}$ are independently of each other H or optionally substituted $C_{1-40}$ carbyl or hydrocarbyl.

2. The polymer according to claim 1, characterized in that it comprises one or more units of formula II

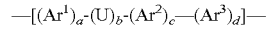

wherein

U is a unit of formula I as defined in claim 1, $Ar^1$, $Ar^2$, $Ar^3$ are, on each occurrence identically or differently, and independently of each other, aryl or heteroaryl that is different from U, preferably has 5 to 30 ring atoms and is optionally substituted, preferably by one or more groups $R^S$, $R^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, $R^0$ and $R^{00}$ are independently of each other H or optionally substituted $C_{1-40}$ carbyl or hydrocarbyl, P is a polymerisable or crosslinkable group, Sp is a spacer group or a single bond, $X^0$ is halogen, preferably F, Cl or Br, a, b, c are on each occurrence identically or differently 0, 1 or 2, d is on each occurrence identically or differently 0 or an integer from 1 to 10, wherein the polymer comprises at least one repeating unit of formula II wherein b is at least 1.

3. The polymer according to claim 1, characterized in that it additionally comprises one or more repeating units selected of formula III

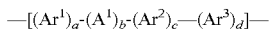  III wherein $Ar^1$, $Ar^2$, $Ar^3$, are, on each occurrence identically or differently, and independently of each other, aryl or heteroaryl that is different from U, preferably has 5 to 30 ring atoms and is optionally substituted, preferably by one or more groups $R^S$, a, b, c are on each occurrence identically or differently 0, 1 or 2, d is on each occurrence identically or differently 0 or an integer from 1 to 10, and $A^1$ is an aryl or heteroaryl group that is different from Formula I and $Ar^{1-3}$, has 5 to 30 ring atoms, is optionally substituted by one or more groups $R^S$, and is selected from aryl or heteroaryl groups having electron donor properties, wherein the polymer comprises at least one repeating unit of formula III wherein b is at least 1, and $R^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-.

4. The polymer according to claim 1, of formula IV:

  IV wherein

A is a unit of formula I as defined in claim 1,

B is a unit that is different from A and comprises one or more aryl or heteroaryl groups that are optionally substituted, x is >0 and ≤1, y is ≥0 and <1, x+y is 1, and n is an integer >1.

5. The polymer according to claim 2, of the following formulae

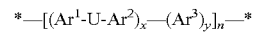  IVa

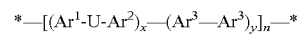  IVb

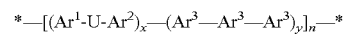  IVc

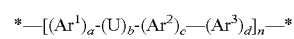  IVd

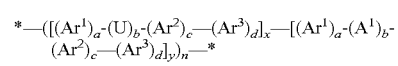  IVe wherein these polymers can be alternating or random copolymers, and wherein in formula IVd and IVe in at least one of the repeating units [(Ar$^1$)$_a$-(U)$_b$- (Ar$^2$)$_c$—(Ar$^3$)$_d$] and in at least one of the repeating units [(Ar$^1$)$_a$-(A$^1$)$_b$-(Ar$^2$)$_c$—(Ar$^3$)$_d$] b is at least 1.

6. The polymer according to claim 1, of the following formulae

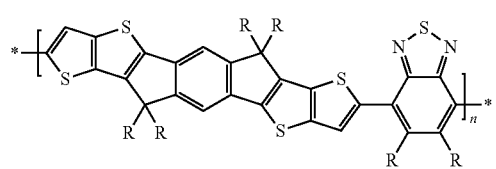  IV1

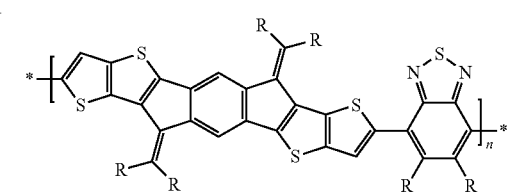  IV2

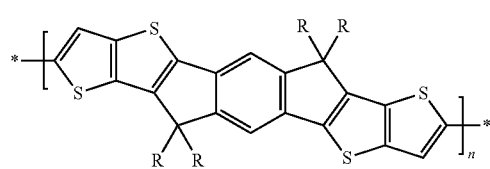  IV3

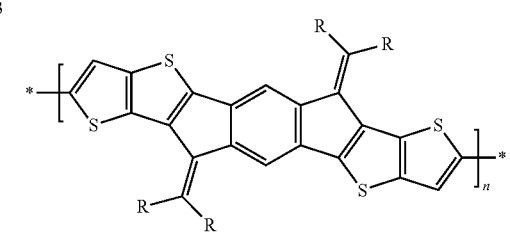  IV4

-continued
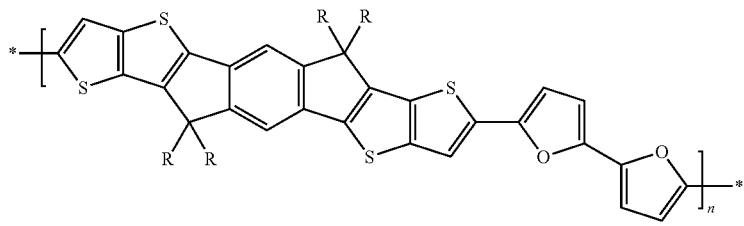
IV5
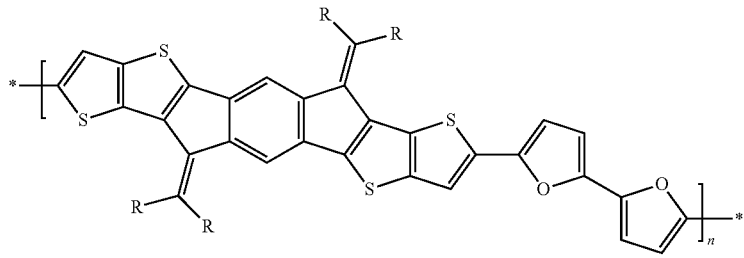
IV6
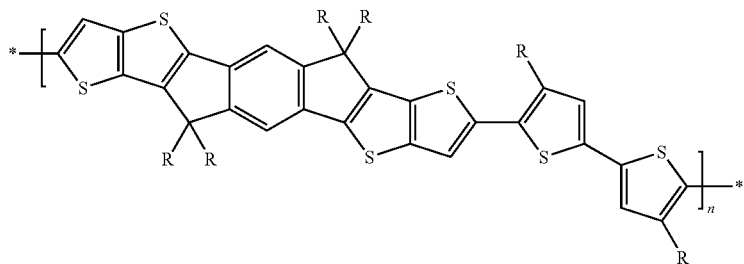
IV7
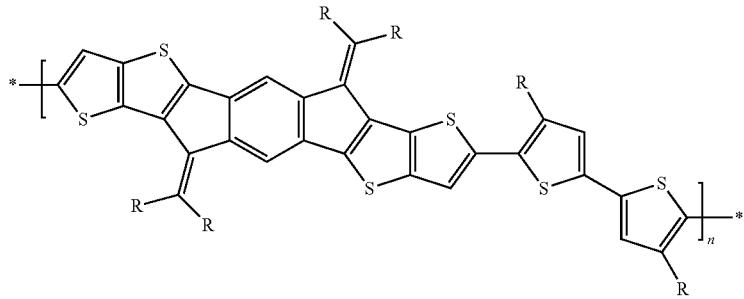
IV8
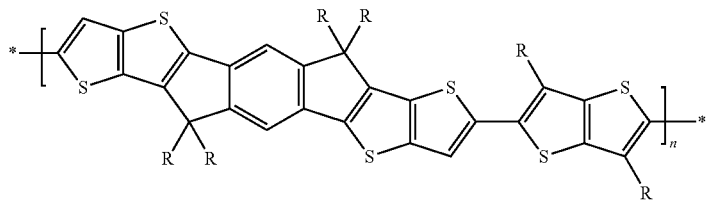
IV9
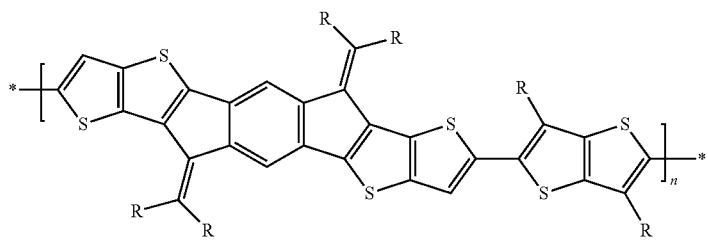
IV10

-continued

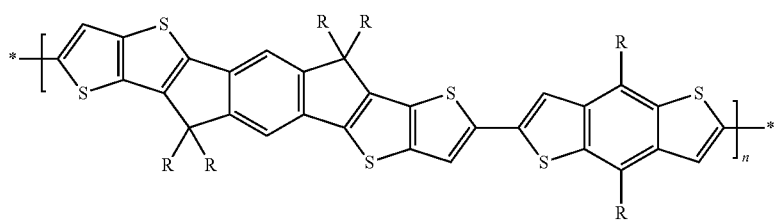

IV11

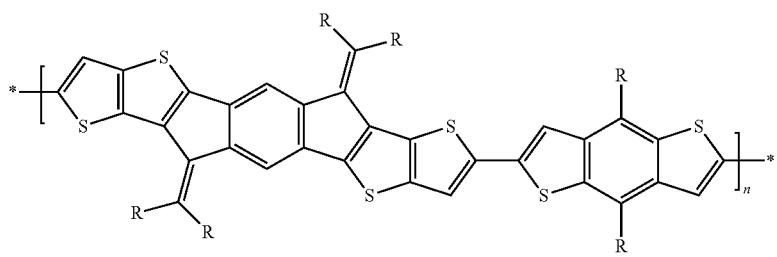

IV12

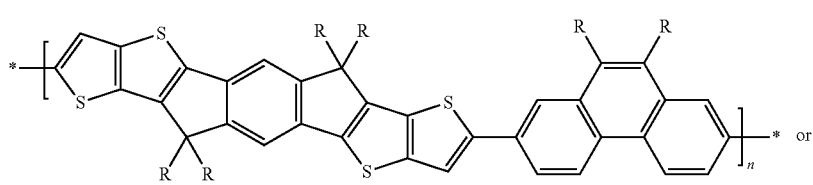

IV13

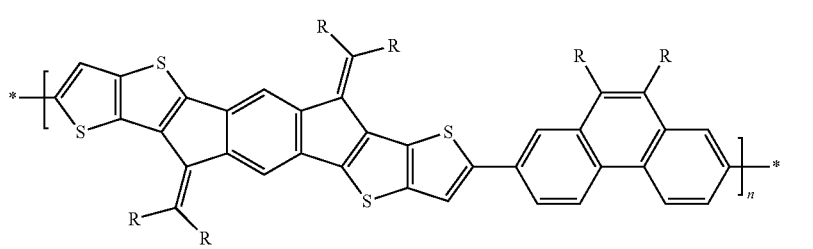

IV14 wherein R has on each occurrence identically or differently one of the meanings of $R^1$ as given in claim 1.

7. The polymer according to claim 4, of formula V $$R^5\text{-chain-}R^6 \qquad V$$

wherein "chain" is a polymer chain selected of formulae IV, and $R^5$ and $R^6$ denote independently of each other F, Br, Cl, H, —CH$_2$Cl, —CHO, —CH=CH$_2$, —SiR'R"R'", —SnR'R"R'", —BR'R", —B(OR')(OR"), —B(OH)$_2$, —ZnCl, —MgCl, —MgBr or P-Sp, R', R" and R'" have independently of each other one of the meanings of $R^0$, and two of R', R" and R'" may also form a ring together with the hetero atom to which they are attached.

8. The polymer according to claim 2, wherein one or more of $Ar^1$, $Ar^2$ and $Ar^3$ denote aryl or heteroaryl of the following formulae

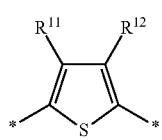
(D1)

-continued

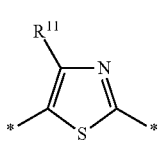
(D2)

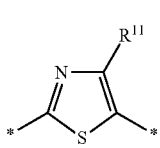
(D3)

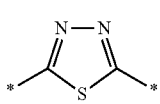
(D4)

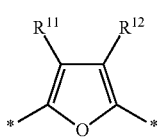
(D5)

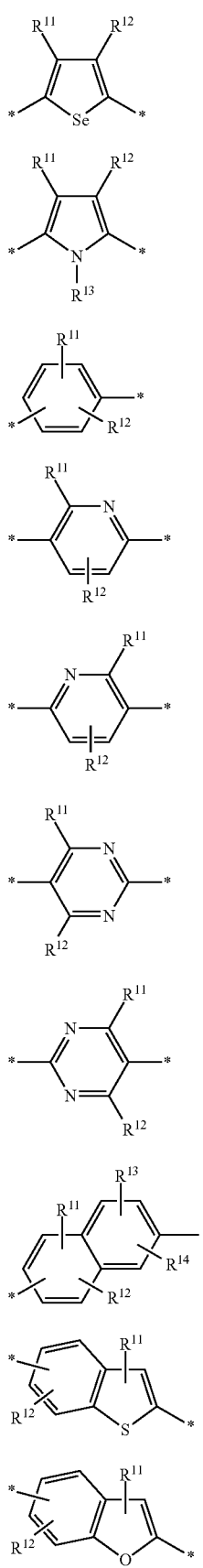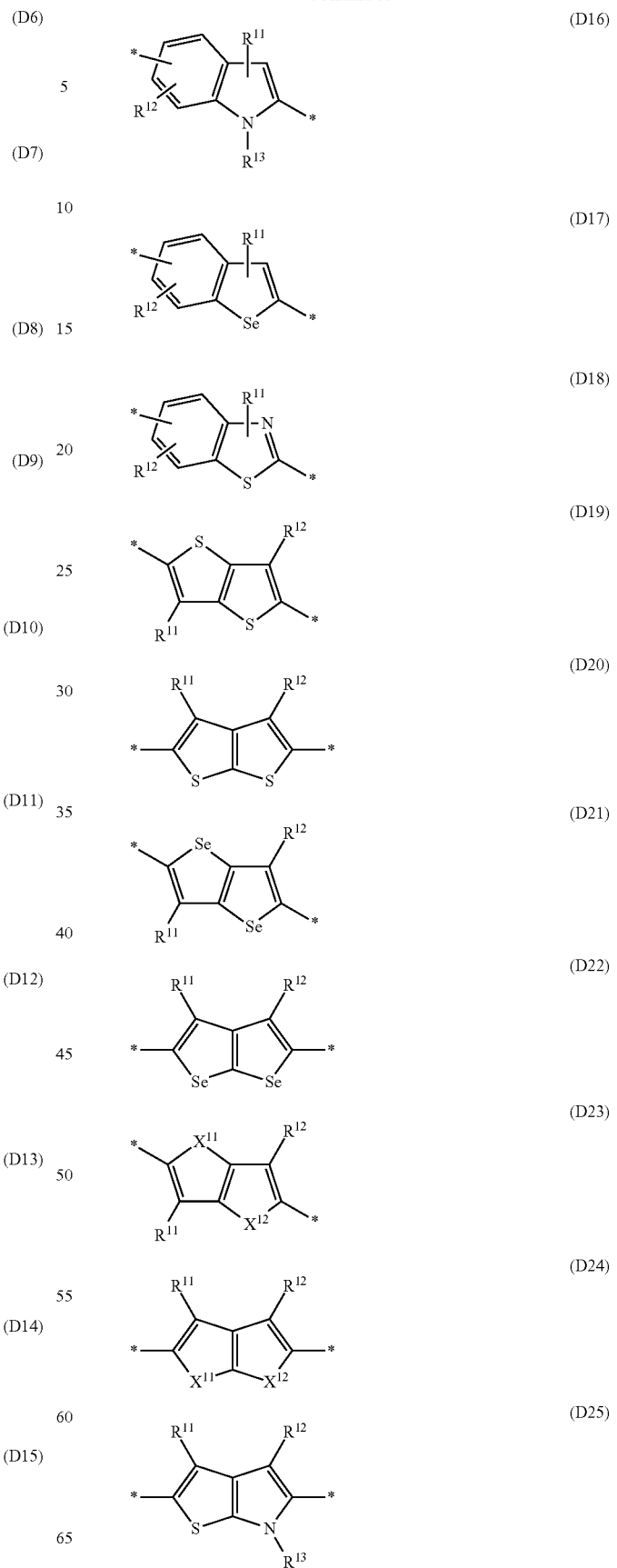

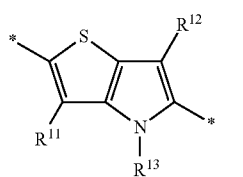
(D26)
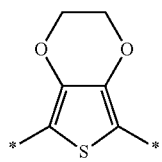
(D27)
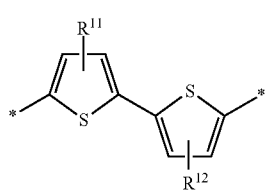
(D28)
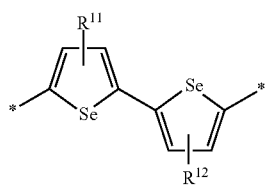
(D29)
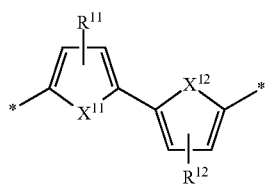
(D30)
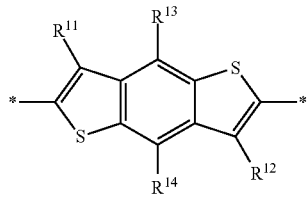
(D31)
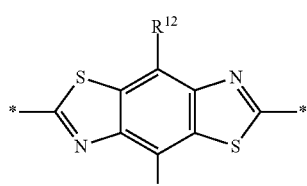
(D32)
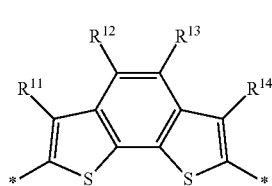
(D33)
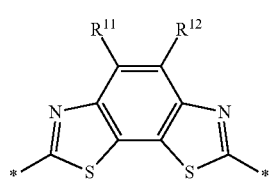
(D34)
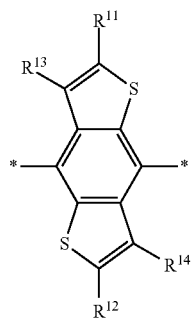
(D35)
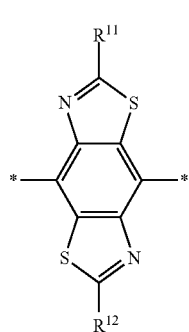
(D36)
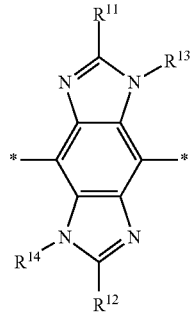
(D37)
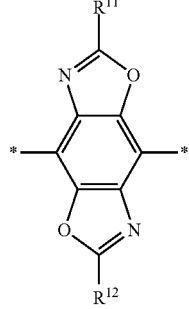
(D38)
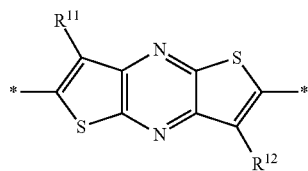
(D39)

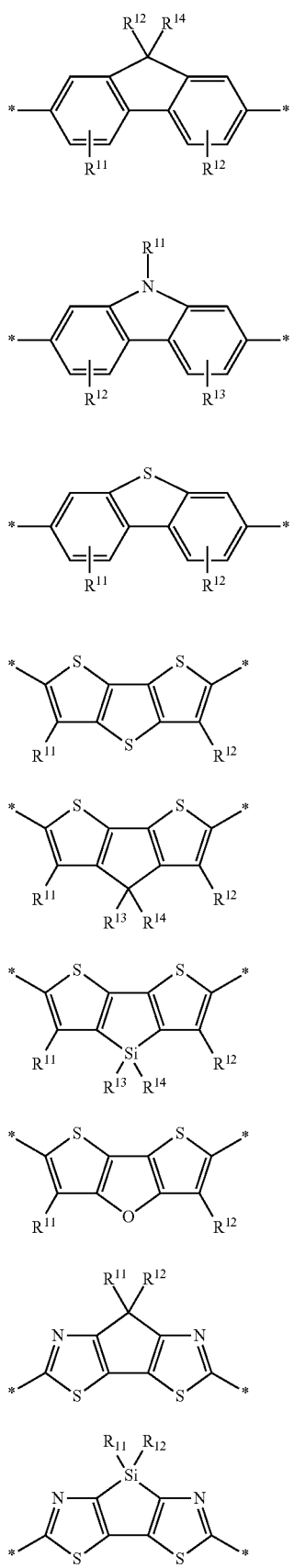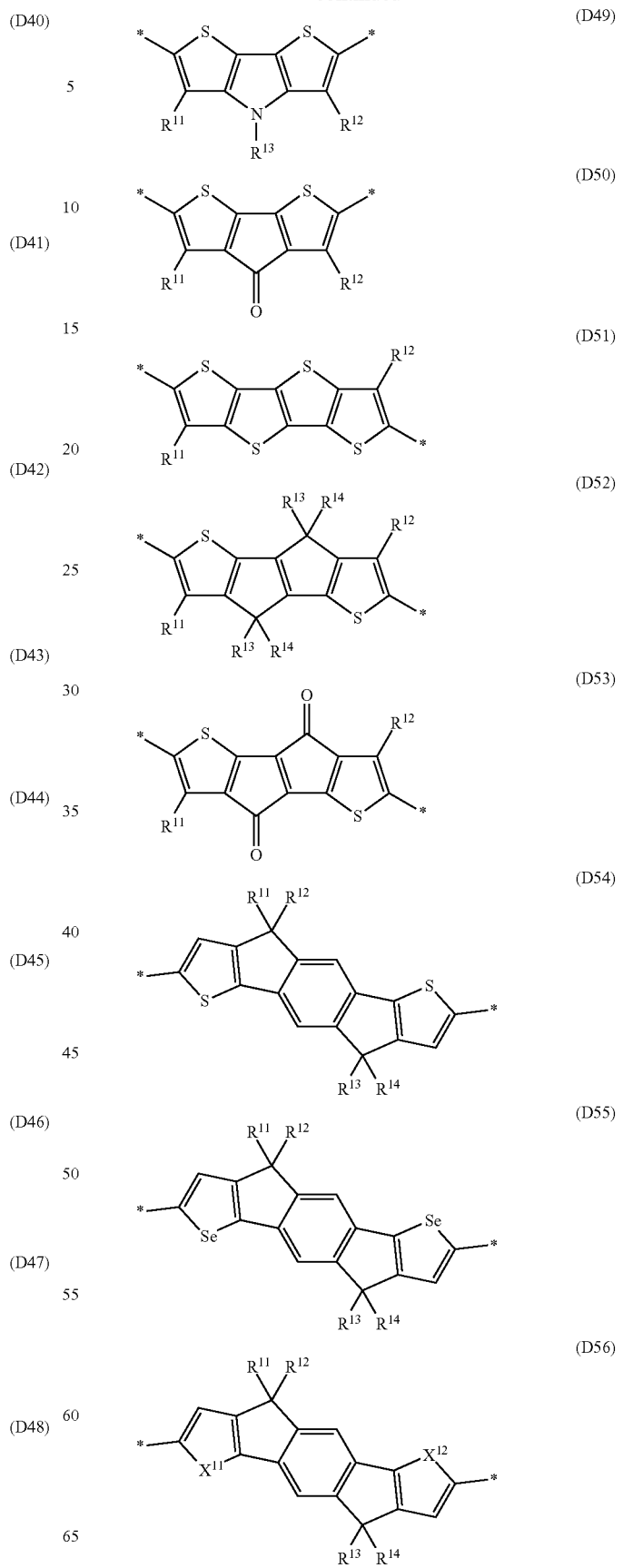

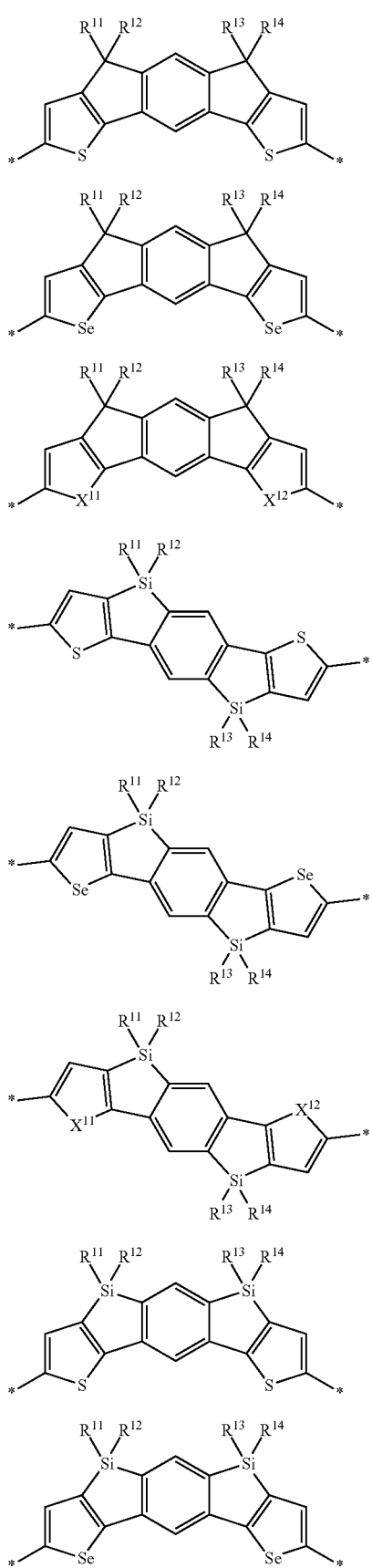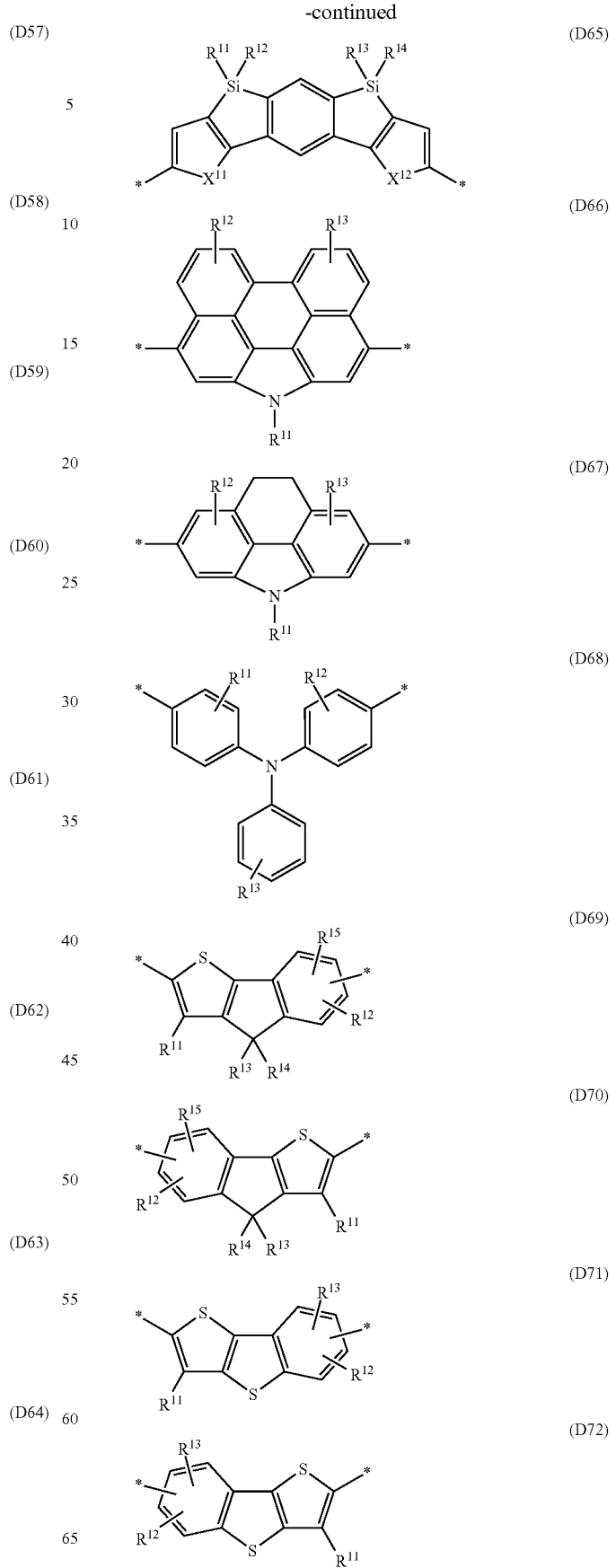

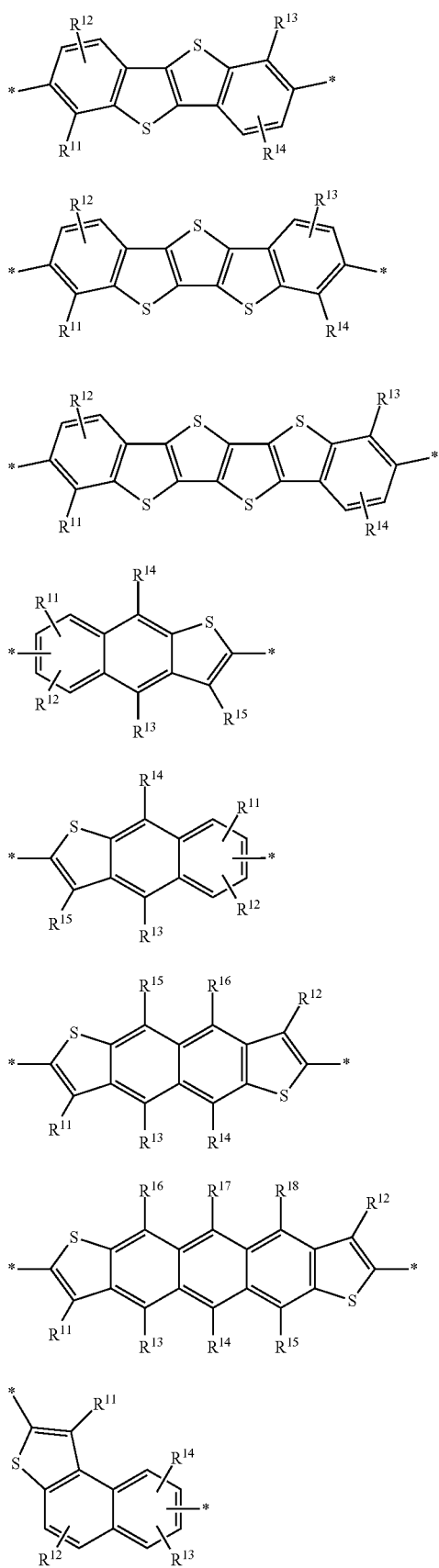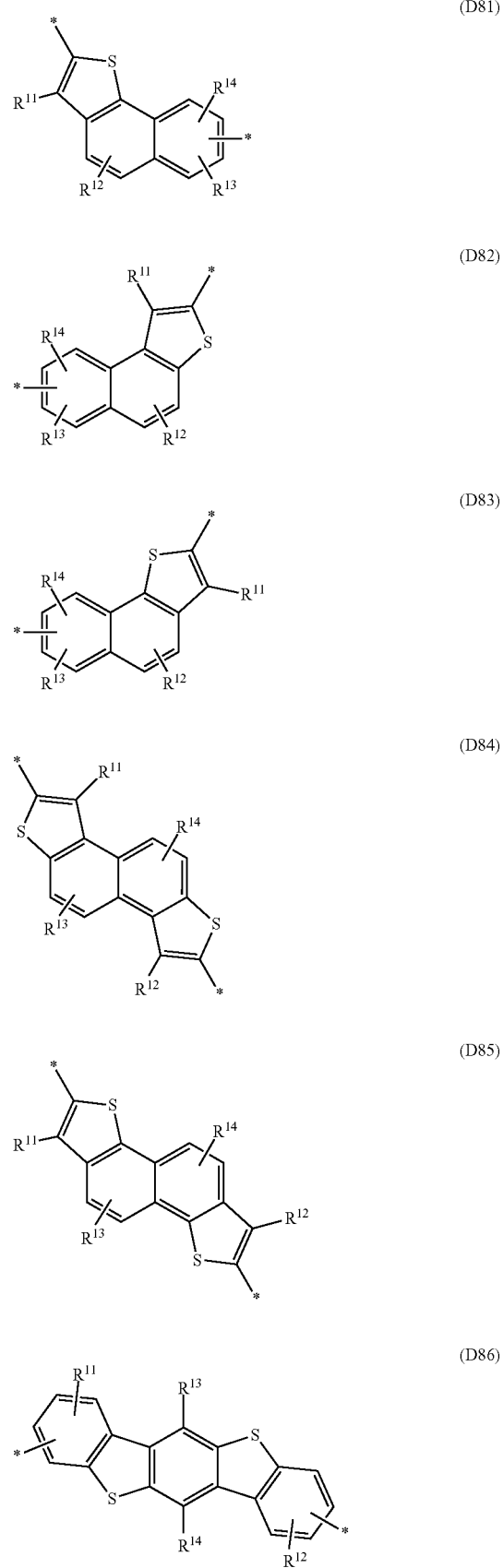

(D87)
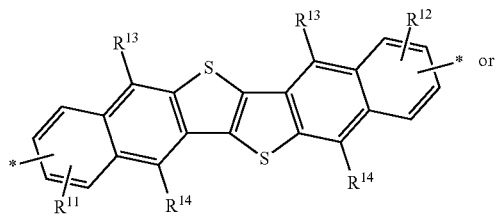
or
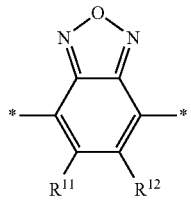
(A4)
(D88)
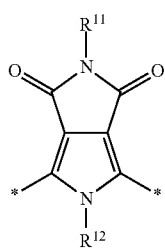
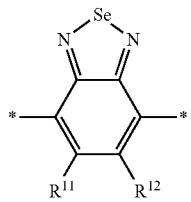
(A5)
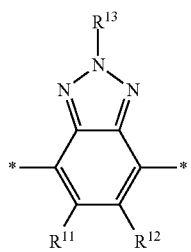
(A6)
wherein one of $X^{11}$ and $X^{12}$ is S and the other is Se, and $R^{11}, R^{12}, R^{13}, R^{14}, R^{15}, R^{16}, R^{17}$ and $R^{18}$ independently of each other denote H or have one of the meanings of $R^1$.
9. The polymer according to claim 3, wherein one or more of the units $Ar^3$ and $A^1$ denote aryl or heteroaryl of the following formulae
(A1)
(A7)
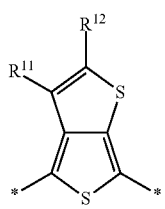
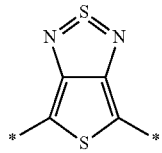
(A2)
(A8)
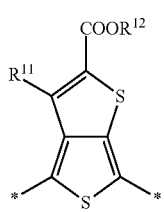
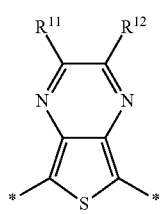
(A3)
(A9)
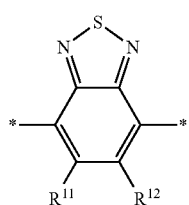
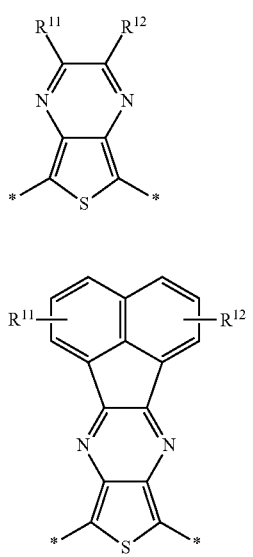

(A10) 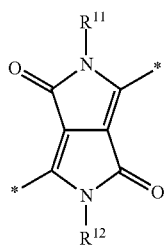
(A11) 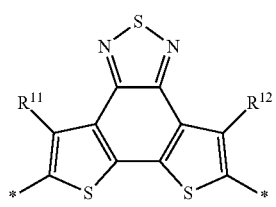
(A12) 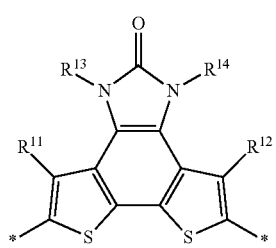
(A13) 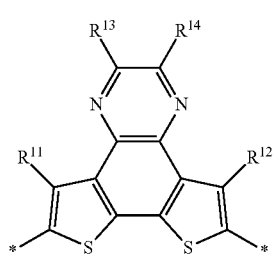
(A14) 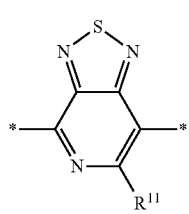
(A15) 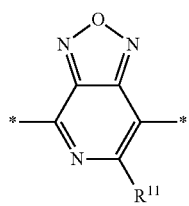
(A16) 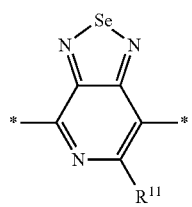
(A17) 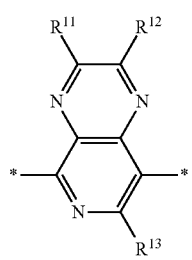
(A18) 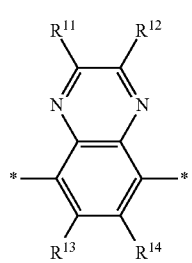
(A19) 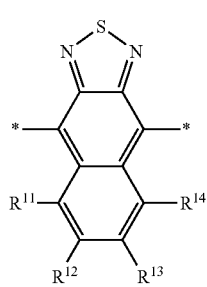
(A20) 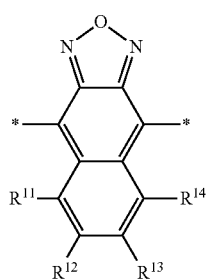

(A21) 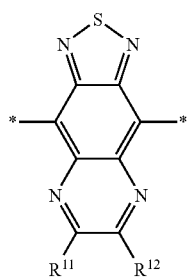
(A22) 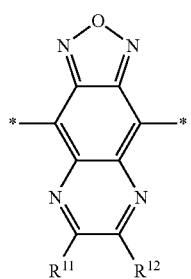
(A23) 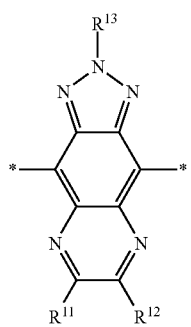
(A24) 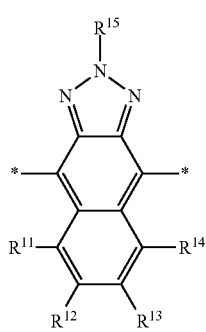
(A25) 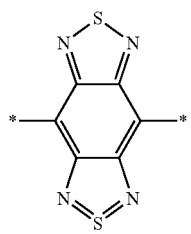
(A26) 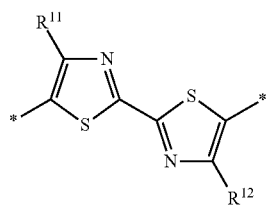
(A27) 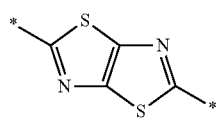
(A28) 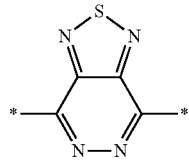
(A29) 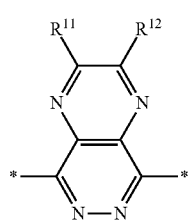
(A30) 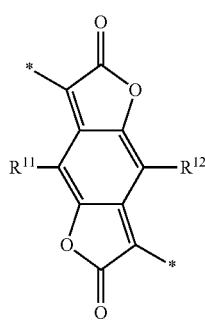
(A31) 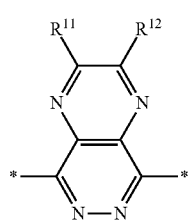
(A32) 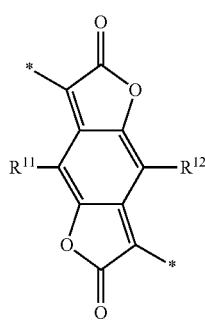

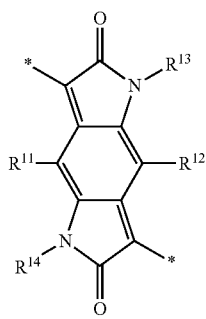
(A33)
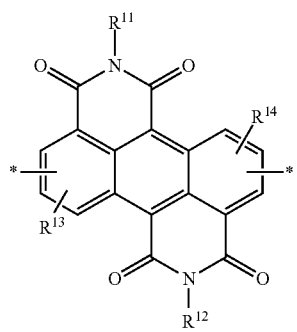
(A39)
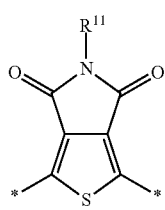
(A34)
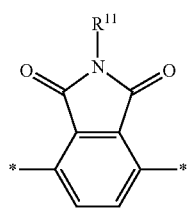
(A35)
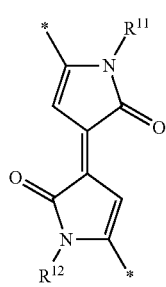
(A40)
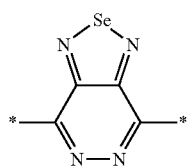
(A36)
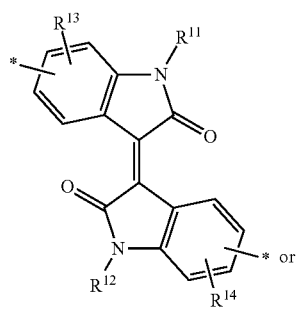
(A41)
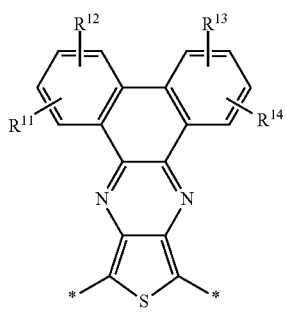
(A37)
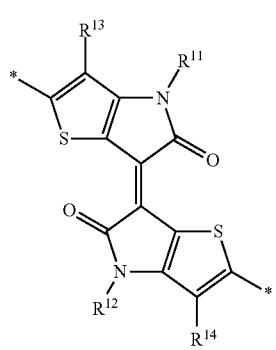
(A42)
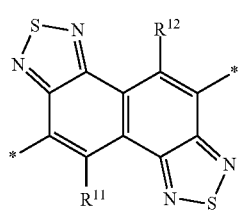
(A38)
wherein one of $X^{11}$ and $X^{12}$ is S and the other is Se, and $R^{11}$, $R^{12}$, $R^{13}$, $R^{14}$ and $R^{15}$ independently of each other denote H or have one of the meanings of $R^1$ as defined in claim 1.

10. The oligomer according to claim 1, of formula VII

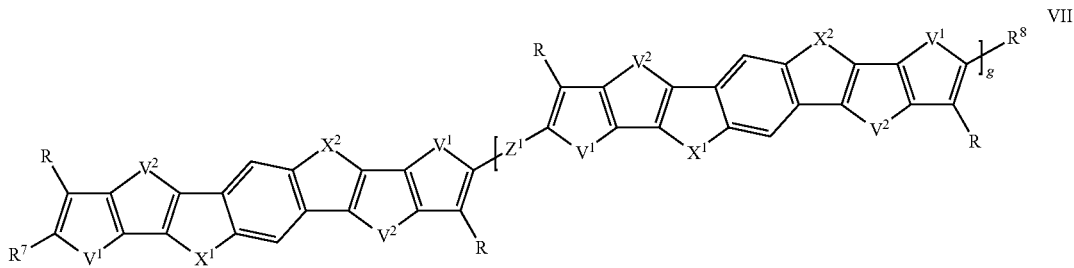

wherein R, $V^1$, $V^2$, $X^1$ and $X^2$ are as defined in claim 1, $Z^1$ denotes a single bond, $(CY^1=CY^2)_h$, $(C\equiv C)_h$, wherein h=1 or 2, or $Ar^5$, wherein $Y^1$, $Y^2$ are as defined in claim 1 and $Ar^5$ is each independently aryl or heteroaryl optionally substituted by $R^S$, $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, $R^7$ and $R^8$ independently of each other denote H, F, Br, Cl, —CN, —NC, —NCO, —NCS, —OCN, —SCN, —C(O)NR°R°°, —C(O)X°, —C(O)R°, —C(O)OR°, —O—C(O)R°, —NH$_2$, —NR°R°°, —SH, —SR°, —SO$_3$H, —SO$_2$R°, —OH, —NO$_2$, —CF$_3$, —SF$_5$, P-Sp-, or optionally substituted silyl, carbyl or hydrocarbyl with 1 to 40 C atoms that is optionally substituted and optionally comprises one or more hetero atoms, and wherein one or more C atoms are optionally replaced by a hetero atom, and R°, R°° are independently of each other H or optionally substituted $C_{1-40}$ carbyl or hydrocarbyl, $X°$ is halogen and g is 1, 2 or 3.

11. The oligomer according to claim 10, which is selected from the following formulae wherein $V^1$, $V^2$, R, $R^7$ and $R^8$ are as defined in claim 10, and Z has one of the meanings of $Z^1$ in claim 10.

12. The oligomer or polymer according to claim 1, wherein $R^1$ and $R^2$ independently of each other denote straight-chain, branched or cyclic alkyl with 1 to 20 C atoms which is unsubstituted or substituted by one or more F atoms, or $R^1$ and $R^2$ independently of each other denote aryl or heteroaryl, each of which is optionally fluorinated, alkylated or alkoxylated and has 4 to 30 ring atoms, or one of $R^1$ and $R^2$ denotes H and the other is selected from the aforementioned alkyl, aryl or heteroaryl groups, or $R^1$ and $R^2$ together form a cyclic alkyl group with 1 to 20 C atoms, which is unsubstituted or substituted by one or more F atoms or by one or more $C_1$-$C_{10}$ alkyl groups.

13. A mixture or blend comprising one or more oligomers or polymers according to claim 1, and one or more compounds or polymers having semiconducting, charge transport, hole/electron transport, hole/electron blocking, electrically conducting, photoconducting or light emitting properties.

14. The mixture or blend according to claim 13, further comprising one or more n-type organic semiconductor compounds.

15. The mixture or blend according to claim 14, characterized in that the n-type organic semiconductor compound is a fullerene or substituted fullerene.

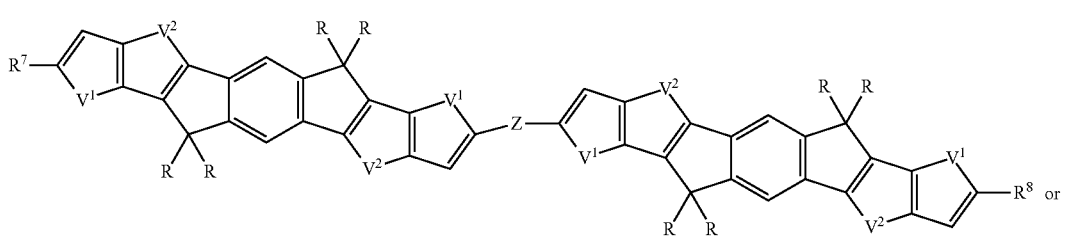

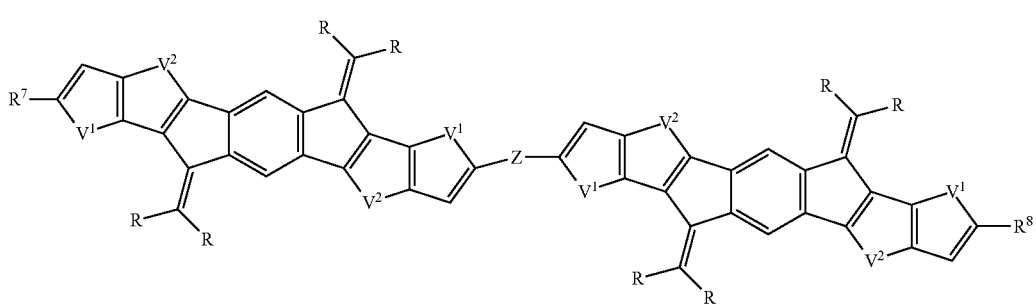

16. A formulation comprising one or more oligomers, polymers, mixtures or blends according to claim 1, and one or more solvents.

17. A charge transport, semiconducting, electrically conducting, photoconducting or light emitting material in optical, electrooptical, electronic, electroluminescent or photoluminescent components or devices, comprising a oligomer or polymer according to claim 1.

18. An optical, electrooptical or electronic component or device comprising one or more oligomers, polymers, mixtures, blends or formulations according to claim 1.

19. The component or device according to claim 18, which is selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (O-SC), photodiodes, laser diodes, photoconductors, photodetectors, electrophotographic devices, electrophotographic recording devices, organic memory devices, sensor devices, charge injection layers, charge transport layers or interlayers in polymer light emitting diodes (PLEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

20. The component or device according to claim 18, which is an OFET, bulk heterojunction (BHJ) OPV device or inverted BHJ OPV device.

21. A Monomer of formula VI

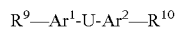

wherein

U is a unit of formula I wherein

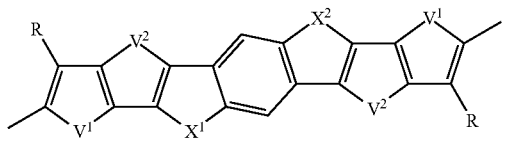

I wherein

V$^1$ and V$^2$ are independently of each other O, S, Se or Te,

X$^1$ and X$^2$ are independently of each other CR$^1$R$^2$, C═CR$^1$R$^2$, SiR$^1$R$^2$ or GeR$^1$R$^2$ R, R$^1$ and R$^2$ independently of each other, and on each occurrence identically or differently, denote H, F, Cl, Br, CN, straight-chain, branched or cyclic alkyl, with 1 to 30 C atoms, in which one or more non-adjacent C atoms are optionally replaced by —O—, —S—, —C(O)—, —C(O)—O—, —O—C(O)—, —O—C(O)—O—, —C(S)—, —C(S)—O—, —O—C(S)—, —O—C(S)—O—, —C(O)—S—, —S—C(O)—, —O—C(O)—S—, —S—C(O)—O—, —S—C(O)—S—, —S—C(S)—S—, —O—C(S)—S—, —S—C(S)—O—, —C(S)—S—, —S—C(S)—, —NR$^0$—, —SiR$^0$R$^{00}$—, —CY$^1$═CY$^2$— or —C≡C— in such a manner that O and/or S atoms are not linked directly to one another, and in which one or more H atoms are optionally replaced by F, Cl, Br, I or CN, or R$^1$ and R$^2$, independently of each other, and on each occurrence identically or differently, denote aryl, heteroaryl, aryloxy or heteroaryloxy with 4 to 20 ring atoms which is optionally substituted, or R$^1$ and R$^2$ together form an alicyclic group with 1 to 20 C atoms, which is optionally fluorinated or alkylated, Y$^1$ and Y$^2$ are independently of each other H, F, Cl or CN, R$^0$ and R$^{00}$ are independently of each other H or optionally substituted C$_{1-40}$ carbyl or hydrocarbyl, Ar$^1$, Ar$^2$ are, on each occurrence identically or differently, and independently of each other, aryl or heteroaryl that is different from U, and is optionally substituted, and R$^9$ and R$^{10}$ independently of each other denote F, Br, Cl, —CH$_2$Cl, —CHO, —CH═CH$_2$, —SiR'R"R'", —SnR'R"R'", —BR'R", —B(OR')(OR"), —B(OH)$_2$, —ZnCl, —MgCl, or —MgBr, wherein R', R"and R'" have independently of each other one of the meanings of R$^0$ as defined above, and two of R', R" and R'" may also form a ring together with the hetero atom to which they are attached.

22. A process of preparing a polymer according to claim 1, by coupling one or more monomers of formula VI R$^9$—Ar$^1$—U—Ar$^2$—R$^{10}$ wherein U is a unit of formula I wherein V$^1$ and V$^2$ are independently of each other O, S, Se or Te, X$^1$ and X$^2$ are independently of each other CR$^1$R$^2$, C═CR$^1$R$^2$, SiR$^1$R$^2$ or GeR$^1$R$^2$, R, R$^1$ and R$^2$ independently of each other, and on each occurrence identically or differently, denote H, F, Cl, Br, CN, straight-chain, branched or cyclic alkyl, with 1 to 30 C atoms, in which one or more non-adjacent C atoms are optionally replaced by —O—, —S—, —C(O)—, —C(O)—O—, —O—C(O)—, —O—C(O)—O—, —C(S)—, —C(S)—O—, —O—C(S)—, —O—C(S)—O—, —C(O)—S—, —S—C(O)—, —O—C(O)—S—, —S—C(O)—O—, —S—C(O)—S—, —S—C(S)—S—, —O—C(S)—S—, —S—C(S)—O—, —C(S)—S—, —S—C(S)—, —NR$^0$—, —SiR$^0$R$^{00}$—, —CY$^1$═CY$^2$— or —C≡C— in such a manner that O and/or S atoms are not linked directly to one another, and in which one or more H atoms are optionally replaced by F, Cl, Br, I or CN, or R$^1$ and R$^2$, independently of each other, and on each occurrence identically or differently, denote aryl, heteroaryl, aryloxy or heteroaryloxy with 4 to 20 ring atoms which is optionally substituted, or R$^1$ and R$^2$ together form an alicyclic group with 1 to 20 C atoms, which is optionally fluorinated or alkylated, Y$^1$ and Y$^2$ are independently of each other H, F, Cl or CN, R$^0$ and R$^{00}$ are independently of each other H or optionally substituted C$_{1-40}$ carbyl or hydrocarbyl, Ar$^1$ and Ar$^2$ are, on each occurrence identically or differently, and independently of each other, aryl or heteroaryl that is different from U, preferably has 5 to 30 ring atoms and is optionally substituted, preferably by one or more groups R$^S$, and wherein R$^9$ and R$^{10}$ are selected from halogen, stannyl and boronate groups SnR'R"R'", —BR'R", —B(OR')(OR"), or —B(OH)2, wherein R', R" and R'" have independently of each other one of the meanings of R$^0$ as defined above, and two of R', R" and R'" may also form a ring together with the hetero atom to which they are attached, with each other and/or with one or more monomers selected from the following formulae

     C1

     C2 wherein $Ar^3$ are, on each occurrence identically or differently, and independently of each other, aryl or heteroaryl that is different from U, preferably has 5 to 30 ring atoms and is optionally substituted, preferably by one or more groups $R^S$, as $A^1$ aryl or heteroaryl that is different from formula I in an aryl-aryl coupling reaction.

* * * * *